(12) United States Patent
Aikawa et al.

(10) Patent No.: US 7,732,465 B2
(45) Date of Patent: Jun. 8, 2010

(54) SUBSTITUTED BENZIMIDAZOLES AND METHODS OF THEIR USE

(75) Inventors: Mina E. Aikawa, Emeryville, CA (US); Payman Amiri, Emeryville, CA (US); Jeffrey H. Dove, Emeryville, CA (US); Barry Haskell Levine, Emeryville, CA (US); Christopher McBride, Emeryville, CA (US); Teresa E. Pick, Emeryville, CA (US); Daniel J. Poon, Emeryville, CA (US); Savithri Ramurthy, Emeryville, CA (US); Paul A. Renhowe, Emeryville, CA (US); Cynthia Shafer, Emeryville, CA (US); Darrin Stuart, Emeryville, CA (US); Sharadha Subramanian, Emeryville, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 12/315,779

(22) Filed: Dec. 5, 2008

(65) Prior Publication Data
US 2009/0170904 A1 Jul. 2, 2009

Related U.S. Application Data

(62) Division of application No. 11/513,959, filed on Aug. 30, 2006, now Pat. No. 7,482,367.

(60) Provisional application No. 60/713,108, filed on Aug. 30, 2005, provisional application No. 60/712,539, filed on Aug. 30, 2005, provisional application No. 60/731,591, filed on Oct. 27, 2005, provisional application No. 60/774,684, filed on Feb. 17, 2006.

(51) Int. Cl.
*A61K 31/4439* (2006.01)
(52) U.S. Cl. ..................................... 514/338
(58) Field of Classification Search .................. 514/338
See application file for complete search history.

(56) References Cited

U.S. PATENT DOCUMENTS

| | | | |
|---|---|---|---|
| 3,894,037 A | 7/1975 | Brenneisen et al. |
| 4,197,307 A | 4/1980 | Gallay et al. |
| 4,231,938 A | 11/1980 | Monaghan et al. |
| 4,294,926 A | 10/1981 | Monaghan et al. |
| 4,319,039 A | 3/1982 | Albers-Schonberg |
| 4,346,227 A | 8/1982 | Terahara et al. |
| 4,410,629 A | 10/1983 | Terahara et al. |
| 4,430,502 A | 2/1984 | Nelson |
| 4,444,784 A | 4/1984 | Hoffman et al. |
| 4,537,859 A | 8/1985 | Terahara et al. |
| 4,563,455 A | 1/1986 | Ueda et al. |
| 4,681,893 A | 7/1987 | Roth |
| 4,782,084 A | 11/1988 | Vyas et al. |
| 4,820,850 A | 4/1989 | Verhoeven et al. |
| 4,885,314 A | 12/1989 | Vyas et al. |
| 4,911,165 A | 3/1990 | Lennard et al. |
| 4,916,239 A | 4/1990 | Treiber |
| 4,929,437 A | 5/1990 | Tobert |
| 5,030,447 A | 7/1991 | Joshi et al. |
| 5,041,453 A | 8/1991 | Huang et al. |
| 5,118,853 A | 6/1992 | Lee et al. |
| 5,134,142 A | 7/1992 | Matsuo et al. |
| 5,141,950 A | 8/1992 | Nakane et al. |
| 5,180,589 A | 1/1993 | Joshi et al. |
| 5,189,164 A | 2/1993 | Kapa et al. |
| 5,273,995 A | 12/1993 | Roth |
| 5,290,946 A | 3/1994 | Lee et al. |
| 5,342,952 A | 8/1994 | Butler et al. |
| 5,344,991 A | 9/1994 | Reitz et al. |
| 5,354,772 A | 10/1994 | Kathawala |
| 5,356,896 A | 10/1994 | Kabadi et al. |
| 5,380,738 A | 1/1995 | Norman et al. |
| 5,393,790 A | 2/1995 | Reitz et al. |
| 5,409,944 A | 4/1995 | Black et al. |
| 5,420,245 A | 5/1995 | Brown et al. |
| 5,436,265 A | 7/1995 | Black et al. |
| 5,446,059 A | 8/1995 | Rocher et al. |
| 5,466,823 A | 11/1995 | Talley et al. |
| 5,474,995 A | 12/1995 | Ducharme et al. |
| 5,489,691 A | 2/1996 | Butler et al. |
| 5,510,510 A | 4/1996 | Patel et al. |
| 5,523,430 A | 6/1996 | Patel et al. |
| 5,532,359 A | 7/1996 | Marsters, Jr. et al. |
| 5,536,752 A | 7/1996 | Ducharme et al. |
| 5,550,142 A | 8/1996 | Ducharme et al. |
| 5,571,792 A | 11/1996 | Bolton et al. |
| 5,589,485 A | 12/1996 | Hochlowski et al. |
| 5,602,098 A | 2/1997 | Sebti et al. |
| 5,604,260 A | 2/1997 | Guay et al. |
| 5,633,272 A | 5/1997 | Talley et al. |
| 5,661,152 A | 8/1997 | Bishop et al. |
| 5,693,633 A | 12/1997 | Boyd et al. |
| 5,698,584 A | 12/1997 | Black et al. |
| 5,710,140 A | 1/1998 | Ducharme et al. |
| 5,717,100 A | 2/1998 | Selnick et al. |

(Continued)

FOREIGN PATENT DOCUMENTS

AU 200039816 A1 11/2000

(Continued)

OTHER PUBLICATIONS

U.S. Appl. No. 60/349,925, filed Jan. 18, 2002, Barrow et al.

(Continued)

*Primary Examiner*—James D Anderson
(74) *Attorney, Agent, or Firm*—Swiss Tanner, P.C.

(57) ABSTRACT

New substituted benzimidazole compounds, compositions, and methods of inhibition of kinase activity associated with tumorigenesis in a human or animal subject are provided. In certain embodiments, the compounds and compositions are effective to inhibit the activity of at least one serine/threonine kinase or receptor tyrosine kinase. The new compounds and compositions may be used either alone or in combination with at least one additional agent for the treatment of a serine/threonine kinase- or receptor tyrosine kinase-mediated disorder, such as cancer.

3 Claims, 15 Drawing Sheets

U.S. PATENT DOCUMENTS

| | | | |
|---|---|---|---|
| 5,852,046 | A | 12/1998 | Lang et al. |
| 5,861,419 | A | 1/1999 | Dube et al. |
| 5,932,598 | A | 8/1999 | Talley et al. |
| 5,932,600 | A | 8/1999 | Saunders et al. |
| 5,972,968 | A | 10/1999 | De Nanteuil et al. |
| 6,001,843 | A | 12/1999 | Dube et al. |
| 6,001,866 | A | 12/1999 | Cornicelli et al. |
| 6,020,343 | A | 2/2000 | Belley et al. |
| 6,037,136 | A | 3/2000 | Beach et al. |
| 6,040,327 | A | 3/2000 | De Nanteuil et al. |
| 6,121,308 | A | 9/2000 | Hauel et al. |
| 6,127,380 | A | 10/2000 | Nelson et al. |
| 6,127,389 | A | 10/2000 | Oku et al. |
| 6,172,073 | B1 | 1/2001 | Audia et al. |
| 6,204,467 | B1 | 3/2001 | Greenholtz, Jr. et al. |
| 6,211,177 | B1 | 4/2001 | Sperl et al. |
| 6,268,391 | B1 | 7/2001 | Dickerson et al. |
| 6,281,193 | B1 | 8/2001 | Strom et al. |
| 6,284,781 | B1 | 9/2001 | Danishefsky et al. |
| 6,288,237 | B1 | 9/2001 | Hoefle et al. |
| 6,352,985 | B1 | 3/2002 | Yamasaki et al. |
| 6,353,108 | B1 | 3/2002 | Bouchet et al. |
| 6,358,932 | B1 | 3/2002 | Monia |
| 6,391,636 | B1 | 5/2002 | Monia |
| 6,458,813 | B1 | 10/2002 | Mantlo et al. |
| 6,509,336 | B1 | 1/2003 | Dong et al. |
| 6,509,357 | B1 | 1/2003 | Zhou et al. |
| 6,515,133 | B1 | 2/2003 | Thurkauf et al. |
| 6,518,291 | B1 | 2/2003 | Saunders et al. |
| 6,548,520 | B1 | 4/2003 | Adams et al. |
| 6,706,738 | B2 | 3/2004 | Clark et al. |
| 6,710,069 | B2 | 3/2004 | Zhou et al. |
| 6,756,410 | B2 | 6/2004 | Mehta |
| 6,855,714 | B2 | 2/2005 | Blume et al. |
| 6,911,446 | B2 | 6/2005 | Tang et al. |
| 6,919,354 | B2 | 7/2005 | Zhou et al. |
| 7,071,216 | B2 | 7/2006 | Renhowe et al. |
| 2001/0006975 | A1 | 7/2001 | Wood et al. |
| 2002/0132842 | A1 | 9/2002 | Hofmeister et al. |
| 2002/0137774 | A1 | 9/2002 | Riedl et al. |
| 2003/0055057 | A1 | 3/2003 | Blume et al. |
| 2003/0078274 | A1 | 4/2003 | Lipton |
| 2003/0119868 | A1 | 6/2003 | Grillot et al. |
| 2003/0144286 | A1 | 7/2003 | Frenkel et al. |
| 2003/0175348 | A1 | 9/2003 | Kofler et al. |
| 2003/0191170 | A1 | 10/2003 | Hofmeister et al. |
| 2003/0199562 | A1 | 10/2003 | Malamas et al. |
| 2004/0087626 | A1 | 5/2004 | Renhowe et al. |
| 2004/0087637 | A1 | 5/2004 | Zhou et al. |
| 2004/0106608 | A1 | 6/2004 | Munchhof et al. |
| 2004/0116387 | A1 | 6/2004 | Malm et al. |
| 2004/0122237 | A1 | 6/2004 | Amiri et al. |
| 2004/0127527 | A1 | 7/2004 | Hongu et al. |
| 2004/0209892 | A1 | 10/2004 | Di Pietro et al. |
| 2005/0038022 | A1 | 2/2005 | Morris et al. |
| 2005/0054705 | A1 | 3/2005 | Heinelt et al. |
| 2005/0136065 | A1 | 6/2005 | Valiante, Jr. |
| 2005/0192287 | A1 | 9/2005 | Costales et al. |
| 2005/0245547 | A1 | 11/2005 | Kim et al. |

FOREIGN PATENT DOCUMENTS

| | | |
|---|---|---|
| AU | 777275 | 10/2004 |
| EP | 0 604 181 | 6/1994 |
| EP | 0 618 221 | 10/1994 |
| EP | 0639573 A1 | 2/1995 |
| EP | 0 675 112 | 10/1995 |
| EP | 0 696 593 | 2/1996 |
| EP | 0 701 907 | 3/1996 |
| EP | 1183254 | 1/2005 |
| JP | 2001-322903 | 11/2001 |
| JP | 2002-141067 | 5/2002 |
| JP | 2003-246704 | 9/2003 |
| WO | WO 84/02131 | 6/1984 |
| WO | WO 94/15932 | 7/1994 |
| WO | WO 94/19357 | 9/1994 |
| WO | WO 95/08542 | 3/1995 |
| WO | WO 95/10514 | 4/1995 |
| WO | WO 95/10515 | 4/1995 |
| WO | WO 95/10516 | 4/1995 |
| WO | WO 95/11917 | 5/1995 |
| WO | WO 95/12572 | 5/1995 |
| WO | WO 95/12612 | 5/1995 |
| WO | WO 95/25086 | 9/1995 |
| WO | WO 95/32987 | 12/1995 |
| WO | WO 95/34535 | 12/1995 |
| WO | WO 96/00736 | 1/1996 |
| WO | WO 96/05168 | 2/1996 |
| WO | WO 96/05169 | 2/1996 |
| WO | WO 96/05529 | 2/1996 |
| WO | WO 96/06138 | 2/1996 |
| WO | WO 96/06193 | 2/1996 |
| WO | WO 96/16443 | 5/1996 |
| WO | WO 96/17861 | 6/1996 |
| WO | WO 96/21456 | 7/1996 |
| WO | WO 96/21701 | 7/1996 |
| WO | WO 96/22278 | 7/1996 |
| WO | WO 96/24611 | 8/1996 |
| WO | WO 96/24612 | 8/1996 |
| WO | WO 96/30017 | 10/1996 |
| WO | WO 96/30018 | 10/1996 |
| WO | WO 96/30343 | 10/1996 |
| WO | WO 96/30362 | 10/1996 |
| WO | WO 96/30363 | 10/1996 |
| WO | WO 96/31111 | 10/1996 |
| WO | WO 96/31477 | 10/1996 |
| WO | WO 96/31478 | 10/1996 |
| WO | WO 96/31501 | 10/1996 |
| WO | WO 96/33159 | 10/1996 |
| WO | WO 96/34850 | 11/1996 |
| WO | WO 96/34851 | 11/1996 |
| WO | WO 97/00252 | 1/1997 |
| WO | WO 97/02920 | 1/1997 |
| WO | WO 97/03047 | 1/1997 |
| WO | WO 97/03050 | 1/1997 |
| WO | WO 97/03069 | 1/1997 |
| WO | WO 97/04785 | 2/1997 |
| WO | WO 97/12613 | 4/1997 |
| WO | WO 97/17070 | 5/1997 |
| WO | WO 97/18813 | 5/1997 |
| WO | WO 97/21701 | 6/1997 |
| WO | WO 97/23478 | 7/1997 |
| WO | WO 97/26246 | 7/1997 |
| WO | WO 97/30053 | 8/1997 |
| WO | WO 97/38665 | 10/1997 |
| WO | WO 97/44350 | 11/1997 |
| WO | WO 98/02436 | 1/1998 |
| WO | WO 98/02438 | 1/1998 |
| WO | WO 98/28980 | 7/1998 |
| WO | WO 98/29119 | 7/1998 |
| WO | WO 00/29404 | 5/2000 |
| WO | WO 00/35917 | 6/2000 |
| WO | WO 00/44777 | 8/2000 |
| WO | WO 00/50032 | 8/2000 |
| WO | WO 00/61186 | 10/2000 |
| WO | WO 00/61580 | 10/2000 |
| WO | WO 01/01986 A1 | 1/2001 |
| WO | WO 01/30768 | 5/2001 |
| WO | WO 01/66539 A1 | 9/2001 |
| WO | WO 01/72708 A2 | 10/2001 |
| WO | WO 01/72712 A1 | 10/2001 |
| WO | WO 01/98278 | 12/2001 |
| WO | WO 02/083064 | 10/2002 |
| WO | WO 02/083111 A2 | 10/2002 |

| | | |
|---|---|---|
| WO | WO 02/083138 | 10/2002 |
| WO | WO 02/083139 | 10/2002 |
| WO | WO 02/083140 | 10/2002 |
| WO | WO 03/013526 | 2/2003 |
| WO | WO 03/024899 A2 | 3/2003 |
| WO | WO 03/039460 | 5/2003 |
| WO | WO 03/042184 A1 | 5/2003 |
| WO | WO 03/043985 A1 | 5/2003 |
| WO | WO 03/049527 | 6/2003 |
| WO | WO 03/049678 | 6/2003 |
| WO | WO 03/049679 | 6/2003 |
| WO | WO 03/050064 | 6/2003 |
| WO | WO 03/050122 | 6/2003 |
| WO | WO 03/079973 | 10/2003 |
| WO | WO 03/082272 A1 | 10/2003 |
| WO | WO 03/087089 | 10/2003 |
| WO | WO 03/091245 A1 | 11/2003 |
| WO | WO 03/099211 | 12/2003 |
| WO | WO 03/105855 | 12/2003 |
| WO | WO 03/106417 | 12/2003 |
| WO | WO 2004/014881 A2 | 2/2004 |
| WO | WO 2004/035056 A1 | 4/2004 |
| WO | WO 2004/035740 A2 | 4/2004 |
| WO | WO 2004/039774 | 5/2004 |
| WO | WO 2004/085425 | 10/2004 |
| WO | WO 2004/085425 A1 | 10/2004 |
| WO | WO 2004/087153 | 10/2004 |
| WO | WO 2004/087153 A2 | 10/2004 |
| WO | WO 2004/103995 A1 | 12/2004 |
| WO | WO 2005/000404 A2 | 1/2005 |
| WO | WO 2005/005421 A1 | 1/2005 |
| WO | WO 2005/016914 A1 | 2/2005 |
| WO | WO 2005/030140 A2 | 4/2005 |
| WO | WO 2005/032548 | 4/2005 |
| WO | WO 2005/032548 A1 * | 4/2005 |
| WO | WO 2005/037273 | 4/2005 |
| WO | WO 2005/037273 A1 | 4/2005 |
| WO | WO 2005/070920 | 8/2005 |
| WO | WO 2005/073224 A2 | 8/2005 |

OTHER PUBLICATIONS

U.S. Appl. No. 60/712,539, filed Aug. 30, 2005, Payman et al.
U.S. Appl. No. 60/713,108, filed Aug. 30, 2005, Novartis AG.
U.S. Appl. No. 60/731,591, filed Oct. 27, 2005, Darrin et al.
U.S. Appl. No. 60/774,684, filed Feb. 17, 2006, Darrin et al.
U.S. Appl. No. 60/832,715, Jul. 21, 2006, Ahmad et al.
"Sex, genes and women's health.", *Nature Genetics* 25: 1-2, 2002.
"Tumor angiogenesis—new drugs on the block." *Nature Biotechnology*, 17:963-968 (Oct. 1999).
Aprelikova, O. et al., "FLT4, a Novel Class III Receptor Tyrosine Kinase in Chromosome 5q33-qter." *Cancer Res.* 52:746-748 (1992).
Avruch, J. et al. "Raf meets Ras: completing the framework of a signal transduction pathway." *Trends Biochem. Sci.* 19(7):279-83 (1994).
Bagshawe K., "Antibody-Directed Enzyme Prodrug Therapy: A Review." *Drug Dev. Res.* 34:220-230 (1995).
Balant et al., "Metabolic Considerations, etc.," in Manfred ed, Burger's Medicinal Chemistry and Drug Discovery, 5th ed, vol. 1:Principles and Practice, John Wiley & Sons, Inc., 1995.
Ben-Av et al., "Induction of vascular endothelial growth factor expression in synovial fibroblasts by prostaglandin E and interleukin-1: a potential mechanism of inflammatory angiogenesis." *FEBS Letters* 372:83-87 (1995).
Benezra, D. et al., "In Vivo Angiogenic Activity of Interleukins." *Arch. Ophthalmol.* 108:573-576 (1990).
Bergsagel, P. et al., "Promiscuous translocations into immunoglobulin heavy chain switch regions in multiple myeloma." *Proc. Nat. Acad. Sci.* 93:13931-13936 (1996).
Bertolini, G. et al. "A new rational hypothesis for the pharmacophore of the active metabolite of leflunomide, a potent immunosuppressive drug." *J. Med. Chem.* 40(13):2011-6 (1997).

Bodor, N., "Novel Approaches to the Design of Safer Drugs: Soft Drugs and Site-Specific Chemical Delivery Systems." *Advances in Drug Res.* 13:254-331 (1984).
Bos. "ras Oncogenes in Human Cancer: A Review." *Cancer Res.* 49, 4682-9 (1989).
Bouma, B. et al., "Thrombin-activatable fibrinolysis inhibitor (TAFI, plasma procarboxypeptidase B, Procarboxypeptidase R, procarboxypeptidase U)." *Thrombosis Res.* 101:329-354 (2001).
Brose, M. S. et al. "BRAF and RAS Mutations in Human Lung Cancer and Melanoma." *Cancer Res.* 62 6997-7000 (2002).
Cappellen, D. et al., "Frequent activating mutations of FGFR3 in human bladder and cervix carcinomas." (Letter) *Nature Genet.* 23:18-20 (1999).
Chakraborty, I. "Developmental expression of the cyclo-oxygenase-1 and cyclo-oxygenase-2 genes in the peri-implantation mouse uterus and their differential regulation by the blastocyst and ovarian steroids." *J. Mol. Endocrinol.* 16:107-122 (1996).
Chemical Abstracts Index Guide-Appendix IV (1987) paragraph 203.
Chesi, M. et al. "Frequent translocation t(4;14)(p16.3;q32.3) in multiple myeloma is associated with increased expression and activating mutations of fibroblast growth factor receptor 3." (*Nature Genet.* 16:260-264, (1997).
Chiarugi, V. et al., "Cox-2, iNOS and p53 as play-makers of tumor angiogenesis (Review)." *Intl. J. Mol. Med.* 2:715-719 (1998).
Cho et al., "Defective lysosomal targeting of activated fibroblast growth factor receptor 3 in achondroplasia." *Proc. Nat. Acad. Sci.* 101:609-614 (2004).
Connolly, D. et al., "Human Vascular Permeability Factor." *J. Biol. Chem.* 264(33):20017-20024, (1989).
Connolly, D. et al., "Tumor Vascular Permeability Factor Stimulates Endothelial Cell Growth and Angiogenesis." *J. Clin. Invest.* 84:1470-1478 (1989).
Crews, C. M. et al. "Extracellular Signals and Reversible Protein Phosphorylation: What to Mek of it All." *Cell*, 74, 215-17 (1993).
Crump, M. "Inhibition of raf kinase in the treatment of acute myeloid leukemia." *Curr. Pharm. Des.* 8:2243-2248 (2002).
Daum, G. et al., "The ins and outs of Raf kinases." *Trends Biochem. Sci*, 19:474-80 (1994).
Davies, H. et al. "Mutations of the BRAF gene in human cancer." *Nature* 417(6892):949-54 (2002).
Devries, C. et al., *Science* 255:989-991 (1992).
Diaz-Flores, L., "Intense Vascular Sprouting From Rat Femoral Vein Induced by Prostaglandins E1 and E2." *Anat. Rec.*, (238):68-76 (1994).
Dionne, C. et al., "BEK, a receptor for multiple members of the fibroblast growth factor (FGF) family, maps to human chromosome 10q25.3→q26." *Cytogenet. Cell Genet.* 60:34-36 (1992).
Donovan et al., "Constitutive MEK/MAPK activation leads to $p27^{Kip1}$ deregulation and antiestrogen resistance in human breast cancer cells." *J. Biol. Chem.* 276:40888-40895 (2001).
Fernandez et al., "Angotensin II and neovascularization." *J. Lab. Clin. Med.* 105:142-143 (1985).
Ferrara, N. et al., "The Biology of Vascular Endothelial Growth Factor." *Endocrinol. Rev.* 18:4-25 (1997).
Fridman, M. et al., "The minimal fragments of c-Raf-1 and NF1 that can suppress v-Ha-Ras-Induced malignant phenotype." *J. Biol. Chem.*, 269:30105-8 (1994).
Gu, W. et al., "Effect of Novel CAAX Peptidomimetic Farnesyltransferase Inhibitor on Angiogenesis In Vitro and In Vivo." *European J. of Cancer* 35(9):1394-1401 (1999).
Harada, S. et al., "Expression and Regulation of Vascular Endothelial Growth Factor in Osteoblasts." *Clin, Orthop.* 313, 76-80 (1995).
Heinrich, M. C. et al., "Inhibition of KIT tyrosine kinase activity: A novel molecular approach to the treatment of KIT-Positive malignancies." *J. Clin. Onc.* 20, 6 1692-1703 (2002).
Hla, T. et al. "Human cyclooxygenase-2 cDNA." *PNAS* 89:7384-7399 (1992).
Hoshino, R. et al. "Constitutive activation of the 41-/43-kDa mitogen-activated protein kinase signaling pathway in human tumors." *Oncogene* 18(3):813-22 (1999).

Hotte, S. et. al., "BAY 43-9006: Early clinical data in patients with advanced solid malignancies." *Current Pharmaceutical Design* 8: 2249-2253, 2002.

Iupac 1974 Recommendations for Section E, Fundamental Stereochemistry, *Pure Appl. Chem. 45*:13-30 (1976).

Jain et al., "Polymorphism in Pharmacy", Indian Drugs, 1986, 23(6), 315-329.

Jang et al., "Mutations in fibroblast growth factor receptor 2 and fibroblast growth factor receptor 3 genes associated with human gastric and colorectal cancers." *Cancer Res*. 61, 3541-3 (2001).

Keegan, K et al., "Isolation of an additional member of the fibroblast growth factor receptor family, FGFR-3." *Proc. Nat. Acad. Sci.* 88:1095-1099 (1991).

Kim, K. et al., Inhibition of vascular endothelial growth factor-induced angiogenesis suppresses tumor growth in vivo. *Nature*, 362:841-844 (1993).

Kolch, W. et al. "Raf-1 protein kinase is required for growth of induced NIH/3T3 cells." *Nature* 349:426-428 (1991).

Kolch, W., Biochem. J. 351: 289-305, 2000 "Meaningful relationships: the regulation of the Ras/Raf/MEK/ERK pathway by protein interactions." *Biochem. J.* 351(Pt 2):289-305 (2000).).

Korte, W. , "Changes of the Coagulation and Fibrinolysis System in Malignancy: Their possible Impact on Future Diagnostic and Therapeutic Procedures." *Clin. Chem. La. Med. 38* (8):679-692 (2000).

Leung, D. et al., "Vascular endothelial growth factor is a secreted angiogenic mitogen." *Science 246*:1306-1309 (1989).

Majima, M. "Significant roles of inducible cyclooxygenase (COX)-2 in angiogenesis in rat sponge implants." *Jpn. J. Pharmacol*. 75:105-114 (1997).

March, "*Advanced Organic Chemistry: Reactions, Mechanisms and Structures*", Fourth Edition, John Wiley & Sons, pp. 69-74 (1992).

Monia, B. P. et al. "Antitumor activity of a phosphorothioate antisense oligodeoxynucleotide targeted against C-*raf* kinase." *Nat. Med.* 2(6):668-75 (1996).

Mustonen, T. et al., "Endothelial receptor tyrosine kinases involved in angiogenesis." *J. Cell Biology*, 129(4):895-898 (1995).

Oh, S. H. et al. "Asymmetric synthesis of bicyclic δ-lactones via the intramolecular, nucleophile-catalyzed aldol lactonization: improved efficiency and expanded scope." *J Org,. Chem*. 70(7):2835-8 (2005).

Partanen, J et al., "FGFR-4, a novel acidic fibroblast growth factor receptor with a distinct expression pattern." *EMBO J*. 10:1347-1354 (1991).

Plouet, J. et al., "Isolation and characterization of a newly identified endothelial cell mitogen produced by AtT-20 cells." *EMBO J* 8:(12) 3801-3806 (1989).

Prescott, D., *Methods in Cell Biology*, vol. XIV, Academic Press, New York, N. W., p. 33-71 et seq. (1976).

Pritchard, C. A. et al. "Conditionally oncogenic forms of the A-Raf and B-Raf protein kinases display different biological and biochemical properties in NIH 3T3 cells." *Mol. Cell. Biol.* 15(11):6430-42 (1995).

Quinn, T. et al., " Fetal liver kinase 1 is a receptor for vascular endothelial growth factor and is selectively expressed in vascular endothelium." *Proc. Natl. Acad. Sci. 90*:7533-7537 (1993).

Rasmussen, T. et al., "FGFR3 dysregulation in multiple myeloma: frequency and prognostic relevance." *Br. J. Haematol*. 117:626-628 (2002).

Rockwell, P. et al., "Role of Protein Tyrosine Kinase Receptors in Cancer: Possibilities for Therapeutic Intervention." *Mol. Cell Differ.* 3(4):315 (1995).

Ruta, M et al, "A novel protein tyrosine kinase gene whose expression is modulated during endothelial cell differentiation." *Oncogene* 3:9-15 (1988).

Sapi, E., "The role of CSF-1 in normal physiology of mammary gland and breast cancer: an update." *Exp. Biol. Med 229*:1-11 (2004).

Sawyer, J. S. et al. "Synthesis of Diaryl Ethers, Diaryl Thioethers, and Diarylamines Mediated by Potassium Flouride—Alumina and 18-Crown-6: Expansion of Scope and Utility." *J. Org. Chem.* 63(18):6338-43 (1998).

Seed, M. et al., "The Inhibition of colon-26 Adenocarcinoma Development and Angiogenesis by Topical Diclofenac in 2.5% Hyaluronan." *Cancer Res. 57*:1625-1629 (1997).

Shan, D. et al. "Prodrug strategies based on intramolecular cyclization reactions." *J. Pharm. Sci*. 86(7):765-7 (1997).

Shibuya, M. et al. "Nucleotide sequence and expression of a novel human receptor-type tyrosine kinase gene (*flt*) closely related to the *fms* family." *Oncogene*, 5:519-524 (1990).

Smolich et al., "The antiangiogenic protein kinase inhibitors SU5416 and SU6668 inhibit the SCF receptor (c-kit) in a human myeloid leukemia cell line and in acute myeloid leukemia blasts." *Blood*, 97, 5; 1413-1421, (2001).

Terman, B. et al., "Identification of a new endothelial cell growth factor receptor tyrosine kinase." *Oncogene* 6:1677-1683 (1991).

Tordeux, M. et al., "Reactions of Trifluoromethyl Bromide and Related Halides: Part 10. Perfluoroalkylation of Aromatic Compounds induced by Sulphur Dioxide Radical Anion Precursors." *J. Chem Soc. Perkin Trans 1*, 2293-2299 (1990).

Tsujii, M. et al., "Cyclooxygenase Regulates Angiogenesis Induced by Colon Cancer Cells." *Cell 93*:705- 716 (1998).

Ullrich, A. et al., "Signal Transduction by Receptors with Tyrosine Kinase Activity.", *Cell*, 61 203-212 (1990).

Van Der Geer, P. et al. "Receptor Protein-Tyrosine Kinases and their Signal Transduction Pathways.", *Annu. Rev. Cell Biol.*, 10:251-337,(1994).

Veikkola et al., "Regulation of angiogenesis via vascular endothelial growth factor receptors." *Cancer Res 60*:203-212 (2000).

Vippagunta et al., "Crystalline solids", Advanced Drug Delivery Reviews 48 (2001) 3-26.

Weber, C. K. et al. "Mitogenic signaling of Ras is regulated by differential interaction with Raf isozymes." *Oncogene* 19(2):169-76 (2000).

Wey S. et al., "Vascular Endothelial Growth Factor Receptors: Expression and Function in Solid Tumors.", *Clinical Advances in Hematology and Oncology*, 2:37-45 (2004).

Xin, X. " Peroxisome Proliferator-activated Receptor ɣ Ligands are potent inhibitors of angiogenesis in Vitro and in Vivo." *J. Biol. Chem. 274*(13):9116-9121 (1999).

Yalpani, M., "Cholesterol Lowering Drugs.", *Chemistry & Industry*, pp. 85-89 (Feb. 5, 1996).

Yuen, S. T. et al. "Similarity of the Phenotypic Patterns Associated with BRAF and KRAS Mutations in Colorectal Neoplasia." *Cancer Res*. 62(22):6451-55 (2002).

Zacharski, L. et al., "Heparin and cancer." *Thromb. Haemost. 80*:10-23 (1998).

Ziche, M. "Role of prostaglandin $E_1$ and copper in angiogenesis." *JNCI* 69:475-482 (1982).

\* cited by examiner

SUBSTITUTED BENZIMIDAZOLES AND METHODS OF THEIR USE

CROSS REFERENCE TO RELATED APPLICATIONS

This application is a divisional and claims the benefit under 35 U.S.C. §120 and 121 of U.S. patent application Ser. No. 11/513,959, filed Aug. 30, 2006, now U.S. Pat. No. 7,482, 367, which in turn claims the benefit under 35 U.S.C. 119(e) to provisional applications U.S. Ser. No. 60/712,539 filed on Aug. 30, 2005, U.S. Ser. No. 60/713,108 filed on Aug. 30, 2005, U.S. Ser. No. 60/731,591 filed on Oct. 27, 2005, and U.S. Ser. No. 60/774,684 filed on Feb. 17, 2006. The entire contents of each of these prior applications are incorporated herein by reference in their entirety.

FIELD OF THE INVENTION

The present invention relates to new substituted benzimidazole compounds, their tautomers, stereoisomers, polymorphs, esters, metabolites, and prodrugs, to the pharmaceutically acceptable salts of the compounds, tautomers, stereoisomers, polymorphs, esters, metabolites, and prodrugs, to compositions of any of the aforementioned embodiments together with pharmaceutically acceptable carriers, and to uses of any of the aforementioned embodiments, either alone or in combination with at least one additional therapeutic agent, in the prophylaxis or treatment of cancer.

BACKGROUND OF THE INVENTION

Kinases known to be associated with tumorigenesis include the Raf serine/threonine kinases and the receptor tyrosine kinases (RTKs).

The Raf serine/threonine kinases are essential components of the Ras/Mitogen-Activated Protein Kinase (MAPK) signaling module that controls a complex transcriptional program in response to external cellular stimuli. Raf genes code for highly conserved serine-threonine-specific protein kinases which are known to bind to the ras oncogene. They are part of a signal transduction pathway believed to consist of receptor tyrosine kinases, p21 ras, Raf protein kinases, Mek1 (ERK activator or MAPKK) kinases and ERK (MAPK) kinases, which ultimately phosphorylate transcription factors. In this pathway Raf kinases are activated by Ras and phosphorylate and activate two isoforms of Mitogen-Activated Protein Kinase Kinase (called Mek1 and Mek2), that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates including transcription factors and in so doing set up their transcriptional program. Raf kinase participation in the Ras/MAPK pathway influences and regulates many cellular functions such as proliferation, differentiation, survival, oncogenic transformation and apoptosis.

Both the essential role and the position of Raf in many signaling pathways have been demonstrated from studies using deregulated and dominant inhibitory Raf mutants in mammalian cells as well as from studies employing biochemical and genetic techniques of model organisms. In many cases, the activation of Raf by receptors that stimulate cellular tyrosine phosphorylation is dependent on the activity of Ras, indicating that Ras functions upstream of Raf. Upon activation, Raf-1 then phosphorylates and activates Mek1, resulting in the propagation of the signal to downstream effectors, such as MAPK (mitogen-activated protein kinase; Crews et al., 1993, Cell 74:215). The Raf serine/threonine kinases are considered to be the primary Ras effectors involved in the proliferation of animal cells (Avruch et al., 1994, *Trends Biochem. Sci.* 19:279).

Raf kinase has three distinct isoforms, Raf-1 (c-Raf), A-Raf, and B-Raf, distinguished by their ability to interact with Ras, to activate MAPK kinase pathway, tissue distribution and sub-cellular localization (Marias et al., *Biochem. J.* 351:289-305, 2000; Weber et al., *Oncogene* 19:169-176, 2000; Pritchard et al., *Mol. Cell. Biol.* 15:6430-6442, 1995). Activating mutation of one of the Ras genes can be seen in about 20% of all tumors and the Ras/Raf/MEK/ERK pathway is activated in about 30% of all tumors (Bos et al., *Cancer Res.* 49:4682-4689, 1989; Hoshino et al., *Oncogene* 18:813-822, 1999). Recent studies have shown that B-Raf mutation in the skin nevi is a critical step in the initiation of melanocytic neoplasia (Pollock et al., *Nature Genetics* 25: 1-2, 2002). Furthermore, most recent studies have disclosed that activating mutation in the kinase domain of B-Raf occurs in about 66% of melanomas, 12% of colon carcinoma and 14% of liver cancer (Davies et al., *Nature* 417:949-954, 2002; Yuen et al., *Cancer Research* 62:6451-6455, 2002; Brose et al., *Cancer Research* 62:6997-7000, 2002).

Melanoma, which continues to represent a significant unmet medical need, is a complex multigenic disease with a poor prognosis, especially in the advanced metastatic state. Activating somatic mutations in the B-Raf proto-oncogene have recently been discovered in a variety of malignancies, and most frequently in melanoma. Approximately 70% of melanoma express a mutated and activated form of B-Raf (V600E), making it an excellent target for drug development. Furthermore, another 10-15% of melanomas express mutant N-Ras, further demonstrating the importance of the MAPK pathway in the growth and survival of melanoma cells.

Inhibitors of the Ras/Raf/MEK/ERK pathway at the level of Raf kinases can potentially be effective as therapeutic agents against tumors with over-expressed or mutated receptor tyrosine kinases, activated intracellular tyrosine kinases, tumors with aberrantly expressed Grb2 (an adapter protein that allows stimulation of Ras by the Sos exchange factor) as well as tumors harboring activating mutations of Raf itself. In the early clinical trials inhibitors of Raf-1 kinase that also inhibit B-Raf have shown promise as therapeutic agents in cancer therapy (Crump, *Current Pharmaceutical Design* 8:2243-2248, 2002; Sebastien et al., *Current Pharmaceutical Design* 8: 2249-2253, 2002).

Disruption of Raf expression in cell lines through the application of RNA antisense technology has been shown to suppress both Ras and Raf-mediated tumorigenicity (Kolch et al., *Nature* 349:416-428, 1991; Monia et al., *Nature Medicine* 2(6):668-675, 1996). It has also been shown that the administration of deactivating antibodies against Raf kinase or the co-expression of dominant negative Raf kinase or dominant negative MEK, the substrate of Raf kinase, leads to the reversion of transformed cells to the normal growth phenotype (see Daum et al., *Trends Biochem. Sci* 1994, 19:474-80; Fridman et al. *J. Biol. Chem.* 1994, 269:30105-8).

Several Raf kinase inhibitors have been described as exhibiting efficacy in inhibiting tumor cell proliferation in vitro and/or in vivo assays (see, e.g., U.S. Pat. Nos. 6,391,636, 6,358,932, 6,037,136, 5,717,100, 6,458,813, 6,204,467, and 6,268,391). Other patents and patent applications suggest the use of Raf kinase inhibitors for treating leukemia (see, e.g., U.S. Pat. Nos. 6,268,391, and 6,204,467, and published U.S. Patent Application Nos. 20020137774; 20020082192; 20010016194; and 20010006975), or for treating breast cancer (see, e.g., U.S. Pat. Nos. 6,358,932, 5,717,100, 6,458,813, 6,268,391, and 6,204,467, and published U.S. Patent Application No. 20010014679).

Angiogenesis also plays an important role in the growth of cancer cells. It is known that once a nest of cancer cells reaches a certain size, roughly 1 to 2 mm in diameter, the cancer cells must develop a blood supply in order for the tumor to grow larger as diffusion will not be sufficient to supply the cancer cells with enough oxygen and nutrients. Thus, inhibition of angiogenesis is expected to inhibit the growth of cancer cells.

Receptor tyrosine kinases (RTKs) are transmembrane polypeptides that regulate developmental cell growth and differentiation, remodeling and regeneration of adult tissues (Mustonen, T. et al., *J. Cell Biology* 129:895-898, 1995; van der Geer, P. et al., *Ann Rev. Cell Biol.* 10:251-337, 1994). Polypeptide ligands, known as growth factors or cytokines, are known to activate RTKs. Signaling RTKs involves ligand binding and a shift in conformation in the external domain of the receptor resulting in its dimerization (Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, 1999; Ullrich, A. et al., *Cell* 61:203-212, 1990). Binding of the ligand to the RTK results in receptor trans-phosphorylation at specific tyrosine residues and subsequent activation of the catalytic domains for the phosphorylation of cytoplasmic substrates (Id).

Two subfamilies of RTKs are specific to the vascular endothelium. These include the vascular endothelial growth factor (VEGF) subfamily and the Tie receptor subfamily. Class V RTKs include VEGFR1 (FLT-1), VEGFR2 (KDR (human), Flk-1 (mouse)), and VEGFR3 (FLT-4) (Shibuya, M. et al., *Oncogene* 5:519-525, 1990; Terman, B. et al., *Oncogene* 6:1677-1683, 1991; Aprelikova, O. et al., *Cancer Res.* 52:746-748, 1992). Members of the VEGF subfamily have been described as being able to induce vascular permeability and endothelial cell proliferation and further identified as a major inducer of angiogenesis and vasculogenesis (Ferrara, N. et al., *Endocrinol. Rev.* 18:4-25, 1997).

VEGF is known to specifically bind to RTKs including FLT-1 and Flk-1 (DeVries, C. et al., *Science* 255:989-991, 1992; Quinn, T. et al., *Proc. Natl. Acad. Sci.* 90:7533-7537, 1993). VEGF stimulates the migration and proliferation of endothelial cells and induces angiogenesis both in vitro and in vivo (Connolly, D. et al., *J. Biol. Chem.* 264:20017-20024, 1989; Connolly, D. et al., *J. Clin. Invest* 84:1470-1478, 1989; Ferrara, N. et al., *Endocrinol. Rev.* 18:4-25, 1997; Leung, D. et al., *Science* 246:1306-1309, 1989; Plouet, J. et al., *EMBO J* 8:3801-3806, 1989).

Studies in various cultured endothelial cell systems have established that VEGFR2 mediates the majority of downstream effects of VEGF in angiogenesis (Wey S. et al., *Clinical Advances in Hematology and Oncology*, 2:37-45, 2004). VEGFR2 mediated proliferation of endothelial cells is believed to involve activation of the Ras/Raf/Mek/Erk pathway (Veikkola T. et al., *Cancer Res* 60:203-212, 2000). VEGFR2 expression has been observed in melanoma, breast cancer, bladder cancer, lung cancer, thyroid cancer, prostate cancer, and ovarian cancer (see Wey et al., supra). Neutralizing monoclonal antibodies to VEGFR2 (KDR) have been shown to be efficacious in blocking tumor angiogenesis (see Kim et al., *Nature* 362:841, 1993; Rockwell et al., *Mol. Cell.* *Differ.* 3:315, 1995). Because angiogenesis is known to be critical to the growth of cancer and to be controlled by VEGF and VEGF-RTK, substantial efforts have been undertaken to develop compounds which inhibit or retard angiogenesis and inhibit VEGF-RTK.

Platelet derived growth factor receptor kinase (PDGFR) is another type of RTK. PDGF expression has been shown in a number of different solid tumors, from glioblastomas and osteosarcoma to prostate carcinomas. In these various tumor types, the biological role of PDGF signaling can vary from autocrine stimulation of cancer cell growth to more subtle paracrine interactions involving adjacent stroma and angiogenesis. PDGF interacts with tyrosine kinases receptors PDGFRα and PDGFRβ. Therefore, inhibiting the PDGFR kinase activity with small molecules is expected to interfere with tumor growth and angiogenesis.

The fibroblast growth factor receptor kinases (FGFRs) represent another type of RTKs. The fibroblast growth factors are a family of polypeptide growth factors involved in a variety of activities, including mitogenesis, angiogenesis, and wound healing. They comprise a family of related but individually distinct tyrosine kinase receptors containing an extracellular domain with either 2 or 3 immunoglobulin (Ig)-like domains, a transmembrane domain, and a cytoplasmic tyrosine kinase domain. The fibroblast growth factor receptors that have been identified include FGFR1 (Ruta, M et al, *Oncogene* 3:9-15, 1988); FGFR2 (Dionne, C et al., *Cytogenet. Cell Genet.* 60:34-36, 1992); FGFR3 (Keegan, K et al., *Proc. Nat. Acad. Sci.* 88:1095-1099, 1991); and FGFR4 (Partanen, J et al., *EMBO J.* 10:1347-1354, 1991).

The role of the fibroblast growth factor receptors, particularly FGFR3, in cancer has been illuminated. Dysregulation of oncogenes by translocation to the immunoglobulin heavy chain (IgH) locus on 14q32 is a seminal event in the pathogenesis of B-cell tumors. In multiple myeloma, translocations to the IgH locus occur in 20 to 60% of cases. For most translocations, the partner chromosome is unknown; for the others, a diverse array of chromosomal partners have been identified, with 11q13, the only chromosome that is frequently involved. Bergsagel et al. identified illegitimate switch recombination fragments (defined as containing sequences from only 1 switch region) as potential markers of translocation events into IgH switch regions in 15 of 21 myeloma cell lines, including 7 of 8 karyotyped lines that had no detectable 14q32 translocation. These translocation breakpoints involved 6 chromosomal loci: 4p16.3; 6; 8q24.13; 11q13.3; 16q23.1; and 21q22.1 (Bergsagel et al., *Proc. Nat. Acad. Sci.* 93:13931-13936, 1996). Chesi et al. (*Nature Genet.* 16:260-264 1997) found the karyotypically silent translocation t(4; 14)(p16.3; q32.3) in 5 myeloma cells lines and in at least 3 of 10 primary tumors associated with multiple myeloma to exhibit increased expression and activation of mutations of FGFR3. The chromosome-4 breakpoints were clustered in a 70-kb region centromeric to FGFR3, which was thought to be the dysregulated oncogene. Two lines and 1 primary tumor with this translocation selectively expressed an FGFR3 allele containing activating mutations identified previously in thanatophoric dwarfism: tyr373 to cys, lys650 to glu, and lys650 to met. For K650E, the constitutive activation of FGFR3 in the absence of ligand had been proved by transfection experiments. Chesi et al. (1997) proposed that after the t(4; 14) translocation, somatic mutation during tumor progression frequently generates an FGFR3 protein that is active in the absence of ligand.

Rasmussen, T et al. cited a frequency of 3 to 24% for the t(4; 14) translocation in multiple myeloma (Rasmussen, T et al., *Br. J. Haematol.* 117:626-628, 2002). The translocation was observed at a significantly lower frequency in patients with monoclonal gammopathy of undetermined significance (MGUS), suggesting a role in the transition from MGUS to multiple myeloma. The t(4; 14) translocation affects 2 potential oncogenes: FGFR3 and multiple myeloma set domain (MMSET). Rasmussen et al. (2002) investigated the frequency of FGFR3 dysregulation and its prognostic value in multiple myeloma. In 16 of 110 (14.5%) multiple myeloma bone marrow samples, they found dysregulated FGFR3 expression.

In addition, further evidence has been presented indicating an oncogenic role for FGFR3 in carcinomas (Cappellen, D. et al., (Letter) *Nature Genet.* 23:18-20, 1999). Cappellen et al. found expression of a constitutively activated FGFR3 in a large proportion of 2 common epithelial cancers, bladder and cervix. FGFR3 appeared to be the most frequently mutated oncogene in bladder cancer, being mutated in more than 30% of cases. FGFR3 seems to mediate opposite signals, acting as a negative regulator of growth in bone and as an oncogene in several tumor types. All FGFR3 missense somatic mutations identified in these cancers were identical to the germinal activating mutations that cause thanatophoric dysplasia (the authors noted that in 2 mutations, this equivalency occurred because the FGFR3b isoform expressed in epithelial cells contains 2 more amino acids than the FGFR3c isoform expressed in bone). Of the FGFR3 alterations in epithelial tumors, the S249C mutation was the most common, affecting 5 of 9 bladder cancers and 3 of 3 cervical cancers.

Evidence has also been presented indicating that activated FGFR3 is targeted for lysosomal degradation by c-Cbl-mediated ubiquitination, and that activating mutations found in patients with achondroplasia and related chondrodysplasias disturb this process, leading to recycling of activated receptors and amplification of FGFR3 signals (Cho et al., *Proc. Nat. Acad. Sci.* 101:609-614, 2004). Cho et al. suggested that this mechanism contributes to the molecular pathogenesis of achondroplasia and represents a potential target for therapeutic intervention. The lysosomal targeting defect is additive to other mechanisms proposed to explain the pathogenesis of achondroplasia.

Other results indicate that FGFR2 and FGFR3 are significant factors in tumorigenesis (Jang J H et al., "Mutations in fibroblast growth factor receptor 2 and fibroblast growth factor receptor 3 genes associated with human gastric and colorectal cancers" *Cancer Res.* 61(9):354 1-3, 2001). Due to their role in multiple myeloma, bladder cancer, and tumorigenesis, development of inhibitors of fibroblast growth factor receptor kinases, particularly inhibitors of FGFR2 and FGFR3, will play an import role in the treatment of cancers.

c-Kit is another receptor tyrosine kinase belonging to PDGF Receptor family and is normally expressed in hematopoietic progenitor, mast and germ cells. C-kit expression has been implicated in a number of cancers including mast cell leukemia, germ cell tumors, small-cell lung carcinoma, gastrointestinal stromal tumors, acute myelogenous leukemia (AML), erythroleukemia, neuroblastoma, melanoma, ovarian carcinoma, breast carcinoma (Heinrich, M. C. et al; *J.*

*Clin. One.* 20, 6 1692-1703, 2002 (review article); Smolich, B. D. et al., *Blood,* 97, 5; 1413-1421).

Overexpression of CSF-1R, the receptor for colony stimulating factor-1 (CSF-1) has been implicated in a number of human carcinomas, including carcinomas of the breast, ovary, endometrium, lung, kidney, pancreas and prostate (Sapi, E., *Exp. Biol. Med.* 229: 1-11, 2004). CSF-1R is tyrosine kinase receptor which, when activated by its ligand CSF-1, triggers signal transduction pathways controlling cell proliferation and differentiation. CSF-1R is expressed in the mammary gland during pregnancy and lactation. Abnormal CSF-1R expression has been correlated with 58% of all breast cancers, and with 85% of invasive breast carcinoma (see Sapi, supra).

A continuing need exists for compounds that inhibit the proliferation of capillaries, inhibit the growth of tumors, treat cancer, modulate cell cycle arrest, and/or inhibit molecules such as one or more of Ras, Raf, mutant B-Raf, VEGFR2 (KDR, Flk-1), FGFR2/3, c-Kit, PDGFRβ, CSF-1R, and pharmaceutical formulations and medicaments that contain such compounds. A need also exists for methods of administering such compounds, pharmaceutical formulations, and medicaments to patients or subjects in need thereof.

SUMMARY OF THE INVENTION

New substituted benzimidazole compounds are provided of the formula (I):

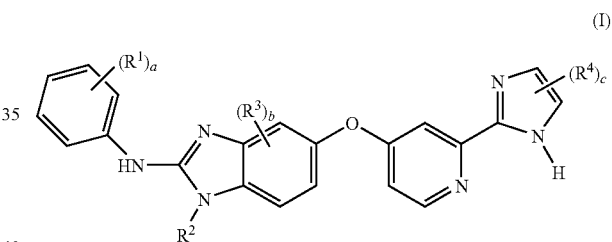

wherein, each $R^1$ is independently selected from hydroxy, halo, $C_{1-6}$ alkyl, $C_{1-6}$ alkoxy, $(C_{1-6}$ alkyl)sulfanyl, $(C_{1-6}$ alkyl)sulfonyl, cycloalkyl, heterocycloalkyl, phenyl, and heteroaryl;

$R^2$ is $C_{1-6}$ alkyl or halo($C_{1-6}$ alkyl);

each $R^3$ is independently selected from halo, $C_{1-6}$ alkyl, and $C_{1-6}$ alkoxy;

each $R^4$ is independently selected from hydroxy, $C_{1-6}$ alkyl, $C_{1-6}$ alkoxy, halo, heterocycloalkylcarbonyl, carboxyl, $(C_{1-6}$ alkoxy)carbonyl, aminocarbonyl, $C_{1-6}$ alkylaminocarbonyl, carbonitrile, cycloalkyl, heterocycloalkyl, phenyl, and heteroaryl;

wherein $R^1$, $R^2$, $R^3$, and $R^4$ may be optionally substituted with one or more substituents independently selected from hydroxy, halo, $C_{1-6}$ alkyl, halo($C_{1-6}$ alkyl), $C_{1-6}$ alkoxy, and halo($C_{1-6}$ alkoxy);

a is 1, 2, 3, 4, or 5;

b is 0, 1, 2, or 3; and c is 1 or 2;

or a tautomer, stereoisomer, polymorph, ester, metabolite, or prodrug thereof or a pharmaceutically acceptable salt of the compound, tautomer, stereoisomer, polymorph, ester, metabolite, or prodrug.

In other embodiments, new substituted benzimidazole compounds are provided of the formula (II):

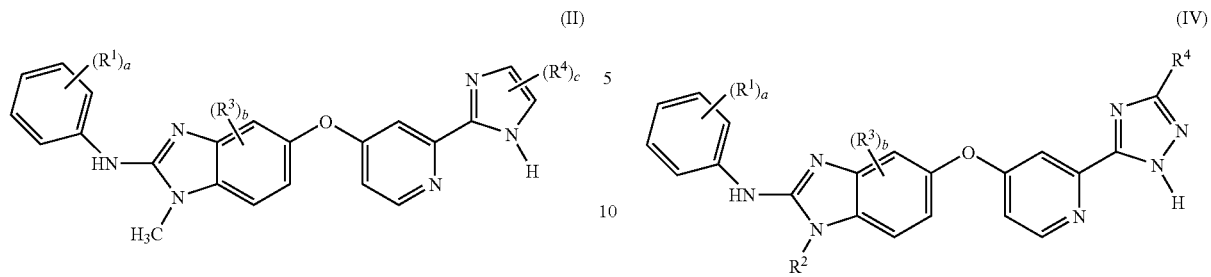

wherein, each $R^1$ is independently selected from $C_{1-6}$ alkyl, $C_{1-6}$ alkoxy, hydroxy, halo, ($C_{1-6}$ alkyl)sulfanyl, ($C_{1-6}$ alkyl)sulfonyl, cycloalkyl, heterocycloalkyl, phenyl, and heteroaryl;

each $R^3$ is independently selected from halo, $C_{1-6}$ alkyl, and $C_{1-6}$ alkoxy;

each $R^4$ is independently selected from hydroxy, $C_{1-6}$ alkyl, $C_{1-6}$ alkoxy, halo, carboxyl, ($C_{1-6}$ alkoxy)carbonyl, aminocarbonyl, carbonitrile, cycloalkyl, heterocycloalkyl, heterocycloalkylcarbonyl, phenyl, and heteroaryl;

wherein $R^1$, $R^2$, $R^3$, and $R^4$ may be optionally substituted with one or more substituents independently selected from hydroxy, halo, $C_{1-6}$ alkyl, and $C_{1-6}$ alkoxy;

a is 1, 2, 3, 4, or 5;
b is 0, 1, 2, or 3; and
c is 1 or 2;

or a tautomer, stereoisomer, polymorph, ester, metabolite, or prodrug thereof or a pharmaceutically acceptable salt of the compound, tautomer, stereoisomer, polymorph, ester, metabolite, or prodrug.

In other embodiments, new substituted benzimidazole compounds are provided of the formula (III):

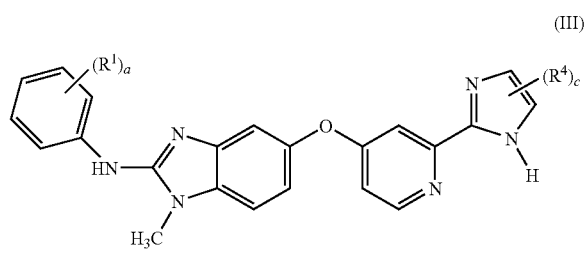

wherein, each $R^1$ is independently selected from $C_{1-6}$ alkyl, $C_{1-6}$ alkoxy, hydroxy, halo, ($C_{1-6}$ alkyl)sulfanyl, ($C_{1-6}$ alkyl)sulfonyl, cycloalkyl, heterocycloalkyl, phenyl, and heteroaryl;

each $R^4$ is independently selected from hydroxy, $C_{1-6}$ alkyl, $C_{1-6}$ alkoxy, halo, carboxyl, ($C_{1-6}$ alkoxy)carbonyl, aminocarbonyl, carbonitrile, cycloalkyl, heterocycloalkyl, heterocycloalkylcarbonyl, phenyl, and heteroaryl;

wherein $R^1$ and $R^4$ may be optionally substituted with one or more substituents independently selected from hydroxy, halo, $C_{1-6}$ alkyl, and $C_{1-6}$ alkoxy;

a is 1, 2, 3, 4, or 5; and
c is 1 or 2;

or a tautomer, stereoisomer, polymorph, ester, metabolite, or prodrug thereof or a pharmaceutically acceptable salt of the compound, tautomer, stereoisomer, polymorph, ester, metabolite, or prodrug.

Also disclosed are compounds of the following formula (IV):

wherein, each $R^1$ is independently selected from $C_{1-6}$ alkyl, $C_{1-6}$ alkoxy, hydroxy, halo, ($C_{1-6}$ alkyl)sulfanyl, ($C_{1-6}$ alkyl)sulfonyl, cycloalkyl, heterocycloalkyl, phenyl, and heteroaryl;

$R^2$ is $C_{1-6}$ alkyl or halo($C_{1-6}$ alkyl);

each $R^3$ is independently selected from halo, $C_{1-6}$ alkyl, and $C_{1-6}$ alkoxy;

each $R^4$ is independently selected from hydroxy, $C_{1-6}$ alkyl, $C_{1-6}$ alkoxy, halo, carboxyl, ($C_{1-6}$ alkoxy)carbonyl, aminocarbonyl, $C_{1-6}$ alkylaminocarbonyl, carbonitrile, carbonitrile ($C_{1-6}$ alkyl), cycloalkyl, heterocycloalkyl, heterocycloalkyl ($C_{1-6}$ alkyl), heterocycloalkylcarbonyl, phenyl; and heteroaryl;

wherein $R^1$, $R^2$, $R^3$, and $R^4$ may be optionally substituted with one or more substituents independently selected from hydroxy, halo, $C_{1-6}$ alkyl, and $C_{1-6}$ alkoxy;

a is 1, 2, 3, 4, or 5; and
b is 0, 1, 2, or 3;

or a tautomer, stereoisomer, polymorph, ester, metabolite, or prodrug thereof or a pharmaceutically acceptable salt of the compound, tautomer, stereoisomer, polymorph, ester, metabolite, or prodrug.

In other embodiments, new substituted benzimidazole compounds are provided of formulas (I)-(IV), wherein each $R^1$ is independently selected from the group consisting of hydroxy, chloro, fluoro, bromo, methyl, ethyl, propyl, butyl, methoxy, ethoxy, propoxy, butoxy, trifluoromethyl, trifluoroethyl, trifluoromethoxy, trifluoroethoxy, trifluoromethylsulfanyl, piperidinyl, $C_{1-6}$ alkylpiperidinyl, piperazinyl, $C_{1-6}$ alkylpiperazinyl, tetrahydrofuranyl, pyridinyl, and pyrimidinyl. In other embodiments, new substituted benzimidazole compounds are provided of formulas (I)-(IV), wherein a is 1 or 2, and at least one $R^1$ is halo($C_{1-6}$ alkyl), such as trifluoromethyl. In other embodiments, new substituted benzimidazole compounds are provided of formulas (I) and (IV), wherein $R^2$ is $C_{1-6}$ alkyl, such as, for example, methyl or ethyl. In further embodiments, new substituted benzimidazole compounds are provided of formulas (I), (II), and (IV), wherein b is 0, and thus $R^3$ is not present. In alternate embodiments, new substituted benzimidazole compounds are provided of formulas (I)-(IV), wherein b is 1, and $R^3$ is $C_{1-6}$ alkoxy, such as, for example, methoxy. In yet further embodiments, new substituted benzimidazole compounds are provided of formulas (I)-(III), wherein c is 1 or 2, and at least one $R^4$ is halo($C_{1-6}$ alkyl), such as, for example, trifluoromethyl.

In other aspects, the present invention provides methods for treating Raf related disorders in a human or animal subject in need of such treatment comprising administering to said subject an amount of any of the embodiments of a compound or a pharmaceutically acceptable salt thereof of formula (I), (II), (III), or (IV) effective to reduce or prevent tumor growth in the subject.

In yet other aspects, the present invention provides methods for treating Raf related disorders in a human or animal subject in need of such treatment comprising administering to said subject an amount of any of the embodiments of a compound or a pharmaceutically acceptable salt thereof of formula (I), (II), (III), or (IV) effective to reduce or prevent tumor growth in the subject in combination with at least one additional agent for the treatment of cancer.

In yet other aspects, the present invention provides therapeutic compositions comprising at least one compound or a pharmaceutically acceptable salt thereof of formula (I), (II), (III), or (IV) in combination with one or more additional agents for the treatment of cancer, as are commonly employed in cancer therapy.

The compounds of the invention are useful in the treatment of cancers, including carcinomas (e.g., of the lungs, pancreas, ovaries, thyroid, bladder or colon), melanoma, myeloid disorders (e.g., myeloid leukemia, multiple myeloma, and erythroleukemia), adenomas (e.g., villous colon adenoma), and sarcomas (e.g., osteosarcoma).

In another aspect, the present invention relates to methods of inhibiting at least one serine/threonine kinase in the MAPK signaling pathway in a subject, or treating a biological condition mediated by a serine/threonine kinase in the MAPK signaling pathway in a subject, comprising administering a therapeutic composition comprising at least one compound or a pharmaceutically acceptable salt thereof of formula (I), (II), (III), or (IV) effective to inhibit the MAPK signaling pathway in the subject. The therapeutic compositions are useful for treating patients with a need for such inhibitors (e.g., those suffering from cancer mediated by abnormal MAPK signaling). In one embodiment, the invention relates to methods of inhibiting Raf kinase in a subject, comprising administering a therapeutic composition comprising {1-Methyl-5-[2-(5-trifluoromethyl-1H-imidazol-2-yl)-pyridin-4-yloxy]-1H-benzoimidazol-2-yl}-(4-trifluoromethyl-phenyl)-amine, and the tautomer, stereoisomer, polymorph, ester, metabolite, or prodrug thereof or a pharmaceutically acceptable salt of the compound, tautomer, stereoisomer, polymorph, ester, metabolite, or prodrug.

In another aspect, the present invention relates to methods of inhibiting at least one tyrosine kinase receptor selected from the group consisting of VEGFR-2, PDGFR-β, pERK, bFGF, FGFR1, FGFR2, FGFR3, c-Kit, and CSF-1R in a subject, or treating a biological condition mediated by at least one of VEGFR-2, PDGFR-β, pERK, bFGF, FGFR1, FGFR2, FGFR3, c-Kit, and CSF-1R comprising administering a therapeutic composition comprising at least one compound or a pharmaceutically acceptable salt thereof of formula (I), (II), (III), or (IV) effective to inhibit the tyrosine kinase receptor in the subject. The therapeutic compounds are useful for treating patients with a need for such inhibitors (e.g., those suffering from cancer mediated by abnormal tyrosine kinase receptor signaling). In one embodiment, the invention relates to methods of inhibiting a tyrosine kinase selected from the group consisting of VEGFR-2, PDGFR-β, pERK, bFGF, FGFR1, FGFR2, FGFR3, c-Kit, and CSF-1R in a subject, comprising administering a therapeutic composition comprising {1-Methyl-5-[2-(5-trifluoromethyl-1H-imidazol-2-yl)-pyridin-4-yloxy]-1H-benzoimidazol-2-yl}-(4-trifluoromethyl-phenyl)-amine or a tautomer, stereoisomer, polymorph, ester, metabolite, or prodrug thereof or a pharmaceutically acceptable salt of the compound, tautomer, stereoisomer, polymorph, ester, metabolite, or prodrug.

The invention further provides compositions, methods of use, and methods of manufacture as described in the detailed description of the invention.

BRIEF DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION OF THE PREFERRED EMBODIMENT

Figure 1:
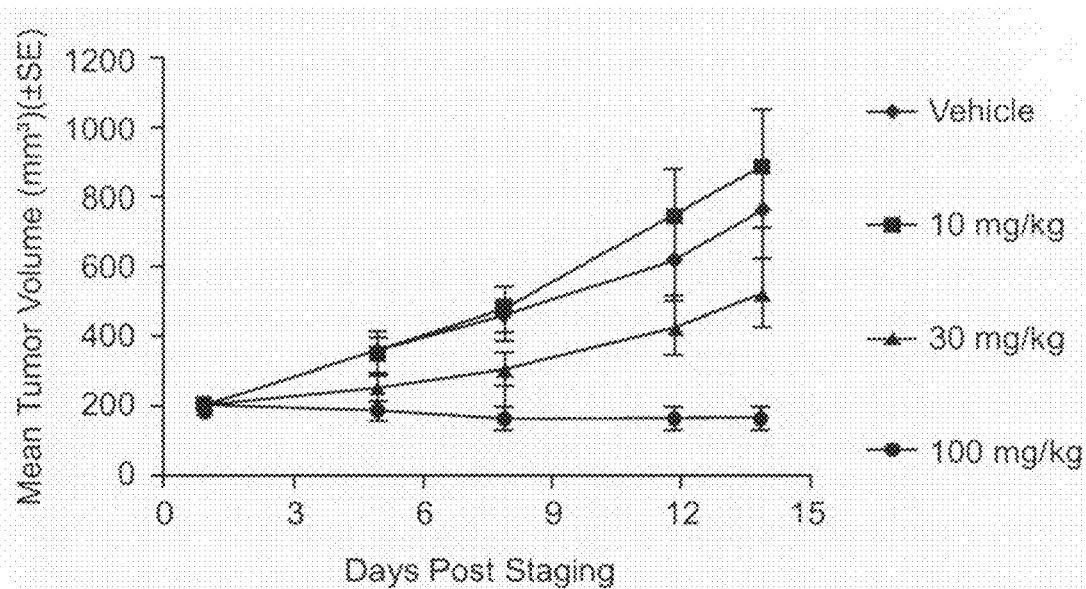
FIG. 1 is a graph showing the mean reduction in tumor volume of A375M human melanoma tumors in mice when treated with a compound of the invention, as described in Example 78.

In accordance with one aspect of the present invention, substituted benzimidazole compounds, are provided of the formula (I):

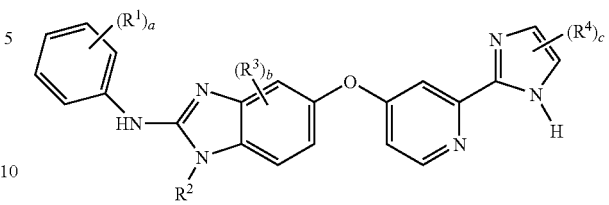

wherein,
each $R^1$ is independently selected from hydroxy, halo, $C_{1-6}$ alkyl, $C_{1-6}$ alkoxy, $(C_{1-6}$ alkyl)sulfanyl, $(C_{1-6}$ alkyl)sulfonyl, cycloalkyl, heterocycloalkyl, phenyl, and heteroaryl;
$R^2$ is $C_{1-6}$ alkyl or halo($C_{1-6}$ alkyl);
each $R^3$ is independently selected from halo, $C_{1-6}$ alkyl, and $C_{1-6}$ alkoxy;
each $R^4$ is independently selected from hydroxy, $C_{1-6}$ alkyl, $C_{1-6}$ alkoxy, halo, carboxyl, $(C_{1-6}$ alkoxy)carbonyl, aminocarbonyl, $C_{1-6}$ alkylaminocarbonyl, carbonitrile, cycloalkyl, heterocycloalkyl, heterocycloalkylcarbonyl, phenyl, and heteroaryl;
wherein $R^1$, $R^2$, $R^3$, and $R^4$ may be optionally substituted with one or more substituents independently selected from hydroxy, halo, $C_{1-6}$ alkyl, halo($C_{1-6}$ alkyl), $C_{1-6}$ alkoxy, and halo($C_{1-6}$ alkoxy);
a is 1, 2, 3, 4, or 5;
b is 0, 1, 2, or 3; and
c is 1 or 2;
or a tautomer, stereoisomer, polymorph, ester, metabolite, or prodrug thereof or a pharmaceutically acceptable salt of the compound, tautomer, stereoisomer, polymorph, ester, metabolite, or prodrug.

In other embodiments, new substituted benzimidazole compounds are provided of the formula (II):

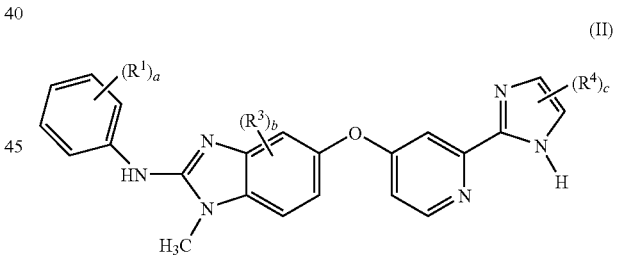

wherein,
each $R^1$ is independently selected from $C_{1-6}$ alkyl, $C_{1-6}$ alkoxy, hydroxy, halo, $(C_{1-6}$ alkyl)sulfanyl, $(C_{1-6}$ alkyl)sulfonyl, cycloalkyl, heterocycloalkyl, phenyl, and heteroaryl;
each $R^3$ is independently selected from halo, $C_{1-6}$ alkyl, and $C_{1-6}$ alkoxy;
each $R^4$ is independently selected from hydroxy, $C_{1-6}$ alkyl, $C_{1-6}$ alkoxy, halo, carboxyl, $(C_{1-6}$ alkoxy)carbonyl, aminocarbonyl, carbonitrile, cycloalkyl, heterocycloalkyl, heterocycloalkylcarbonyl, phenyl, and heteroaryl;
wherein $R^1$, $R^2$, $R^3$, and $R^4$ may be optionally substituted with one or more substituents independently selected from hydroxy, halo, $C_{1-6}$ alkyl, and $C_{1-6}$ alkoxy;
a is 1, 2, 3, 4, or 5;
b is 0, 1, 2, or 3; and
c is 1 or 2;

or a tautomer, stereoisomer, polymorph, ester, metabolite, or prodrug thereof or a pharmaceutically acceptable salt of the compound, tautomer, stereoisomer, polymorph, ester, metabolite, or prodrug.

In other embodiments, new substituted benzimidazole compounds are provided of the formula (III):

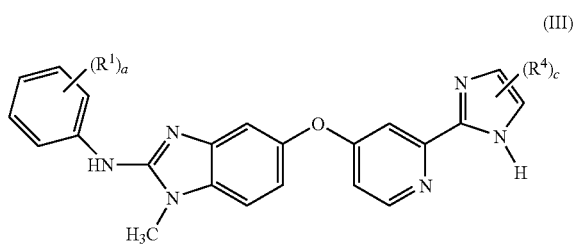

(III)

wherein, each $R^1$ is independently selected from $C_{1-6}$ alkyl, $C_{1-6}$ alkoxy, hydroxy, halo, $(C_{1-6}$ alkyl)sulfanyl, $(C_{1-6}$ alkyl)sulfonyl, cycloalkyl, heterocycloalkyl, phenyl, and heteroaryl;

each $R^4$ is independently selected from hydroxy, $C_{1-6}$ alkyl, $C_{1-6}$ alkoxy, halo, carboxyl, $(C_{1-6}$ alkoxy)carbonyl, aminocarbonyl, carbonitrile, cycloalkyl, heterocycloalkyl, heterocycloalkylcarbonyl, phenyl, and heteroaryl;

wherein $R^1$ and $R^4$ may be optionally substituted with one or more substituents independently selected from hydroxy, halo, $C_{1-6}$ alkyl, and $C_{1-6}$ alkoxy;

a is 1, 2, 3, or 5; and c is 1 or 2;

or a tautomer, stereoisomer, polymorph, ester, metabolite, or prodrug thereof or a pharmaceutically acceptable salt of the compound, tautomer, stereoisomer, polymorph, ester, metabolite, or prodrug.

Also disclosed are compounds of the following formula (IV):

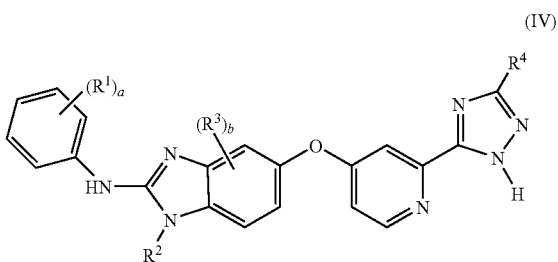

(IV)

wherein, each $R^1$ is independently selected from $C_{1-6}$ alkyl, $C_{1-6}$ alkoxy, hydroxy, halo, $(C_{1-6}$ alkyl)sulfanyl, $(C_{1-6}$ alkyl)sulfonyl, cycloalkyl, heterocycloalkyl, phenyl, and heteroaryl;

$R^2$ is $C_{1-6}$ alkyl or halo($C_{1-6}$ alkyl);

each $R^3$ is independently selected from halo, $C_{1-6}$ alkyl, and $C_{1-6}$ alkoxy;

each $R^4$ is independently selected from hydroxy, $C_{1-6}$ alkyl, $C_{1-6}$ alkoxy, halo, carboxyl, $(C_{1-6}$ alkoxy)carbonyl, aminocarbonyl, $C_{1-6}$ alkylaminocarbonyl, carbonitrile, carbonitrile $(C_{1-6}$ alkyl), cycloalkyl, heterocycloalkyl, heterocycloalkyl $(C_{1-6}$ alkyl), heterocycloalkylcarbonyl, phenyl, and heteroaryl;

wherein $R^1$, $R^2$, $R^3$, and $R^4$ may be optionally substituted with one or more substituents independently selected from hydroxy, halo, $C_{1-6}$ alkyl, and $C_{1-6}$ alkoxy;

a is 1, 2, 3, 4, or 5; and b is 0, 1, 2, or 3;

or a tautomer, stereoisomer, polymorph, ester, metabolite, or prodrug thereof or a pharmaceutically acceptable salt of the compound, tautomer, stereoisomer, polymorph, ester, metabolite, or prodrug.

In other embodiments, new substituted benzimidazole compounds are provided of formulas (I)-(IV), wherein each $R^1$ is independently selected from the group consisting of hydroxy, chloro, fluoro, bromo, methyl, ethyl, propyl, butyl, methoxy, ethoxy, propoxy, butoxy, trifluoromethyl, trifluoroethyl, trifluoromethoxy, trifluoroethoxy, trifluoromethylsulfanyl, piperidinyl, $C_{1-6}$ alkylpiperidinyl, piperazinyl, $C_{1-6}$ alkylpiperazinyl, tetrahydrofuranyl, pyridinyl, and pyrimidinyl. In other embodiments, new substituted benzimidazole compounds are provided of formulas (I)-(IV), wherein a is 1 or 2, and at least one $R^1$ is halo($C_{1-6}$ alkyl), such as trifluoromethyl. In other embodiments, new substituted benzimidazole compounds are provided of formulas (I) and (IV), wherein $R^2$ is $C_{1-6}$ alkyl, such as, for example, methyl or ethyl. In further embodiments, new substituted benzimidazole compounds are provided of formulas (I), (II), and (IV), wherein b is 0, and thus $R^3$ is not present. In alternate embodiments, new substituted benzimidazole compounds are provided of formulas (I)-(IV) wherein b is 1, and $R^3$ is $C_{1-6}$ alkoxy, such as, for example, methoxy. In yet further embodiments, new substituted benzimidazole compounds are provided of formulas (I)-(III), wherein c is 1 or 2, and at least one $R^4$ is halo($C_{1-6}$ alkyl), such as, for example, trifluoromethyl.

In some embodiments, $R^1$, $R^2$, $R^3$, and $R^4$ may be optionally substituted with one to five substituents independently selected from hydroxy, halo, $C_{1-6}$ alkyl, halo($C_{1-6}$ alkyl), $C_{1-6}$ alkoxy, and halo($C_{1-6}$ alkoxy).

In some embodiments, $R^1$, $R^2$, $R^3$, and $R^4$ may be optionally substituted with one to three substituents independently selected from hydroxy, halo, $C_{1-6}$ alkyl, halo($C_{1-6}$ alkyl), $C_{1-6}$ alkoxy, and halo($C_{1-6}$ alkoxy).

In some embodiments, $R^1$ is independently selected from the group consisting of halo, $C_{1-6}$ alkoxy, halo($C_{1-6}$ alkyl), hydroxy, halo($C_{1-6}$ alkoxy), halo($C_{1-6}$ alkyl)sulfonyl, heteroaryl, halo($C_{1-6}$ alkyl)sulfanyl, heterocycloalkyl, and $(C_{1-6}$ alkyl)heterocycloalkyl. In some such embodiments, a is 1 and $R^1$ is independently selected from the group consisting of 2-chloro, 2-ethyl, 2-trifluoromethyl, 3-trifluoromethyl, 4-trifluoromethyl, 3-tert-butyl, 4-tert-butyl, 3-ethyl, 4-ethyl, 4-chloro, 4-bromo, 4-trifluoromethoxy, 4-trifluoromethylsulfanyl, 4-trifluoromethylsulfonyl, and 4-(4-methylpiperazinyl). In still other embodiments, a is 2 and each $R^1$ is independently selected from the group consisting of 2-fluoro, 2-chloro, 2-hydroxy, 2-methoxy, 3-methoxy, 5-methoxy, 4-chloro, 4-fluoro, 3-trifluoromethyl, 4-trifluoromethyl, 5-trifluoromethyl, 5-pyridinyl, 5-pyridinyl-3-yl, 5-pyridinyl-4-yl, 3-tetrahydrofuran-3-yl, 3-isopropyl, 5-isopropyl, and 5-tert-butyl.

In some embodiments, $R^4$ is selected from the group consisting of $C_{1-6}$ alkyl, hydroxy($C_{1-6}$ alkyl), halo($C_{1-6}$ alkyl), halo($C_{1-6}$ alkyl)sulfanyl, $(C_{1-6}$ alkoxy)carbonyl, $(C_{1-6}$ alkyl)heterocycloalkyl, carbonitrile, phenyl, halo($C_{1-6}$ alkyl)phenyl, $(C_{1-6}$ alkyl)heterocycloalkylcarbonyl, and hydroxy($C_{1-6}$ alkylaminocarbonyl). In some such embodiments, c is 1 and $R^4$ is selected from the group consisting of trifluoromethyl, carbonitrile, phenyl, trifluoromethylsulfanyl, methoxycarbonyl, 4-ethylpiperazinyl, 4-ethylpiperazinyl-1-carbonyl, or 2-hydroxyethylaminocarbonyl. In still other embodiments, c is 2 and each $R^4$ is independently selected from the group consisting of methyl, 3-trifluoromethylphenyl, 4-trifluoromethylphenyl, trifluoromethyl, ethoxycarbonyl, hydroxymethyl, and phenyl.

In other embodiments provided is a compound or pharmaceutical acceptable salt thereof wherein the compound has the formula:

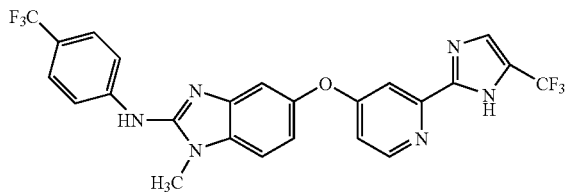

or a tautomer of the compound or a pharmaceutically acceptable salt of the tautomer having the formula:

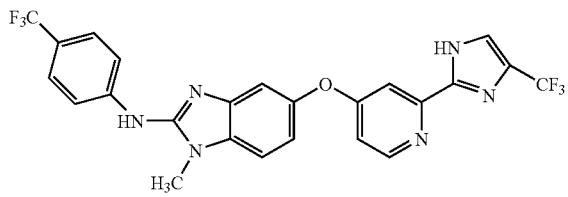

In other aspects, the present invention provides methods for treating Raf related disorders in a human or animal subject in need of such treatment comprising administering to said subject an amount of a compound of formula (I), (II), (III), or (IV) effective to reduce or prevent tumor growth in the subject.

In yet other aspects, the present invention provides methods for treating Raf related disorders in a human or animal subject in need of such treatment comprising administering to said subject an amount of a compound of formula (I), (II), (III), or (IV) effective to reduce or prevent tumor growth in the subject in combination with at least one additional agent for the treatment of cancer.

In yet other aspects, the present invention provides methods for treating Raf related disorders in a human or animal subject in need of such treatment comprising administering to said subject an amount of a compound of formula (I), (II), (III), or (IV) effective to reduce or prevent tumor growth in the subject in combination with at least one additional agent for the treatment of cancer. A number of suitable anticancer agents to be used as combination therapeutics are contemplated for use in the methods of the present invention. Indeed, the present invention contemplates, but is not limited to, administration of numerous anticancer agents such as: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons [e.g. IFN-a, etc.] and interleukins [e.g. IL-2, etc.], etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other examples of chemotherapeutic compounds and anticancer therapies suitable for coadministration with the disclosed compounds of formula (I), (II), (III), or (IV) are known to those skilled in the art.

In preferred embodiments, anticancer agents to be used in combination with compounds of the present invention comprise agents that induce or stimulate apoptosis. Agents that induce apoptosis include, but are not limited to, radiation; kinase inhibitors (e.g., Epidermal Growth Factor Receptor [EGFR] kinase inhibitor, Vascular Growth Factor Receptor [VGFR] kinase inhibitor, Fibroblast Growth Factor Receptor [FGFR] kinase inhibitor, Platelet-derived Growth Factor Receptor [PGFR] I kinase inhibitor, and Bcr-Abl kinase inhibitors such as STI-571, Gleevec, and Glivec]); antisense molecules; antibodies [e.g., Herceptin and Rituxan]; anti-estrogens [e.g., raloxifene and tamoxifen]; anti-androgens [e.g., flutamide, bicalutamide, finasteride, amino-glutethamide, ketoconazole, and corticosteroids]; cyclooxygenase 2 (COX-2) inhibitors [e.g., Celecoxib, meloxicam, NS-398, and non-steroidal antiinflammatory drugs (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP-16, cisplatinum, 5-FU, Doxrubicin, Taxotere or taxol]; cellular signaling molecules; ceramides and cytokines; and staurosprine, and the like.

In other aspects, the present invention provides pharmaceutical compositions comprising at least one compound or a pharmaceutically acceptable salt thereof of formula (I), (II), (III), or (IV) together with a pharmaceutically acceptable carrier suitable for administration to a human or animal subject, either alone or together with other anticancer agents.

In other aspects, the present invention provides methods of manufacture of compounds of formula (I), (II), (III), or (IV) as described herein.

In yet other aspects, the present invention provides compounds which are inhibitors of the enzyme Raf kinase. Since the enzyme is a downstream effector of $p21^{ras}$, the instant inhibitors are useful in pharmaceutical compositions for human or veterinary use where inhibition of the raf kinase pathway is indicated, e.g., in the treatment of tumors and/or cancerous cell growth mediated by Raf kinase. In particular, the compounds are useful in the treatment of human or animal, e.g., murine cancer, since the progression of these cancers is dependent upon the Ras protein signal transduction cascade and therefore is susceptible to treatment by interruption of the cascade by inhibiting Raf kinase activity. Accordingly, the compounds of the invention are useful in treating solid cancers, such as, for example, carcinomas (e.g., of the lungs, pancreas, thyroid, bladder or colon), myeloid disorders (e.g., myeloid leukemia, multiple myeloma, and erythroleukemia), adenomas (e.g., villous colon adenoma), or sarcomas (e.g., osteosarcoma).

"Raf inhibitor" is used herein to refer to a compound that exhibits an $IC_{50}$ with respect to Raf Kinase activity of no more than about 100 μM and more typically not more than about 50 μM, as measured in the Raf/Mek Filtration Assay described generally hereinbelow. Preferred isoforms of Raf Kinase in which the compounds of the present invention will be shown to inhibit, include A-Raf, B-Raf, and C-Raf (Raf-1). "$IC_{50}$" is that concentration of inhibitor which reduces the activity of an enzyme (e.g., Raf kinase) to half-maximal level. Representative compounds of the present invention have been discovered to exhibit inhibitory activity against Raf. Compounds of the present invention preferably exhibit an $IC_{50}$ with respect to Raf of no more than about 10 μM, more preferably, no more than about 5 μM, even more preferably not more than about 1 μM, and most preferably, not more than about 200 nM, as measured in the Raf kinase assays described herein.

As used herein, the phrase "MAPK signal transduction pathway" is an abbreviation that stands for Mitogen activated protein kinase signal transduction pathway in a module that is formed of the Ras-Raf-MEK1-ERK signaling molecules.

"Alkyl" refers to saturated hydrocarbyl groups that do not contain heteroatoms and includes straight chain alkyl groups such as methyl, ethyl, propyl, butyl, pentyl, hexyl, heptyl, octyl, nonyl, decyl, undecyl, dodecyl, and the like. Alkyl also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)—CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. Thus alkyl groups include primary alkyl groups, secondary alkyl groups, and tertiary alkyl groups. The phrase "$C_{1-12}$ alkyl" refers to alkyl groups having from one to twelve carbon atoms. The phrase "$C_{1-6}$ alkyl" refers to alkyl groups having from one to six carbon atoms.

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkoxy" refers to RO— wherein R is an alkyl group. The phrase "$C_{1-6}$ alkoxy" as used herein refers to RO— wherein R is a $C_{1-6}$ alkyl group. Representative examples of $C_{1-6}$ alkoxy groups include methoxy, ethoxy, t-butoxy, and the like.

"($C_{1-6}$ alkoxy)carbonyl" refers to ester —C(=O)—OR wherein R is $C_{1-6}$ alkyl.

"Amidino" refers to the group —C(=NH)NH$_2$. "Amidine" refers to a compound containing such a group.

"Aminocarbonyl" refers herein to the group —C(O)—NH$_2$.

"$C_{1-6}$ alkylaminocarbonyl" refers to the group —C(O)—NRR' where R is $C_{1-6}$ alkyl and R' is selected from hydrogen and $C_{1-6}$ alkyl.

"Carbonyl" refers to the divalent group —C(O)—.

"Carboxyl" refers to —C(=O)—OH.

"Cyano", "carbonitrile", or "nitrile" refers to —CN.

"Carbonitrile($C_{1-6}$ alkyl)" refers to $C_{1-6}$ alkyl substituted with —CN.

"Cycloalkyl" refers to a mono- or polycyclic alkyl substituent. Typical cycloalkyl groups have from 3 to 8 carbon ring atoms. Representative cycloalkyl groups include cyclopropyl, cyclobutyl, cyclopentyl, cyclohexyl, cycloheptyl, and cyclooctyl.

"Halogen" or "halo" refers to chloro, bromo, fluoro, and iodo groups.

"Halo($C_{1-6}$ alkyl)" refers to a $C_{1-6}$ alkyl radical substituted with one or more halogen atoms, preferably one to five halogen atoms. A more preferred halo($C_{1-6}$ alkyl) group is trifluoromethyl.

"Halo($C_{1-6}$ alkyl)phenyl" refers to a phenyl group substituted with a halo($C_{1-6}$ alkyl) group.

"Halo($C_{1-6}$ alkoxy)" refers to an alkoxy radical substituted with one or more halogen atoms, preferably one to five halogen atoms. A more preferred halo($C_{1-6}$ alkoxy) group is trifluoromethoxy.

"Halo($C_{1-6}$ alkyl)sulfonyl" and "halo($C_{1-6}$ alkyl)sulfanyl" refer to substitution of sulfonyl and sulfanyl groups with halo($C_{1-6}$ alkyl) groups wherein sulfonyl and sulfanyl are as defined herein.

"Heteroaryl" refers to an aromatic group having from 1 to 4 heteroatoms as ring atoms in an aromatic ring with the remainder of the ring atoms being carbon atoms. Suitable heteroatoms employed in compounds of the present invention are nitrogen, oxygen, and sulfur, wherein the nitrogen and sulfur atoms may be optionally oxidized. Exemplary heteroaryl groups have 5 to 14 ring atoms and include, for example, benzimidazolyl, benzothiazolyl, benzoxazolyl, diazapinyl, furanyl, pyrazinyl, pyrazolyl, pyridyl, pyridazinyl, pyrimidinyl, pyrroyl, oxazolyl, isoxazolyl, imidazolyl, indolyl, indazolyl, quinolinyl, isoquinolinyl, quinazolinyl, quinoxalinyl, thiazolyl, thienyl, and triazolyl.

"Heterocycloalkyl" refers herein to cycloalkyl substituents that have from 1 to 5, and more typically from 1 to 2 heteroatoms in the ring structure. Suitable heteroatoms employed in compounds of the present invention are nitrogen, oxygen, and sulfur, wherein the nitrogen and sulfur atoms may be optionally oxidized. Representative heterocycloalkyl moieties include, for example, morpholino, piperazinyl, piperidinyl, and the like.

"($C_{1-6}$ alkyl)heterocycloalkyl" refers to a heterocycloalkyl group substituted with a $C_{1-6}$ alkyl group.

"Heterocycloalkyl($C_{1-6}$ alkyl)" refers to $C_{1-6}$ alkyl substituted with heterocycloalkyl.

"Heterocycloalkylcarbonyl" refers herein to the group —C(O)—R$^{10}$ where R$^{10}$ is heterocycloalkyl.

"($C_{1-6}$ alkyl)heterocycloalkylcarbonyl" refers to the group —(O)—R$^{11}$ where R$^{11}$ is ($C_{1-6}$ alkyl)heterocycloalkyl.

"Hydroxy" refers to —OH.

"Hydroxy($C_{1-6}$ alkyl)" refers to a $C_{1-6}$ alkyl group substituted with hydroxy.

"Hydroxy($C_{1-6}$ alkylaminocarbonyl)" refers to a $C_{1-6}$ alkylaminocarbonyl group substituted with hydroxy.

"Imidate" or "imidate ester" refers to the group —C(=NH)O— or to a compound containing such a group. Imidate esters include, for example, the methyl ester imidate —C(=NH)OCH$_3$.

"Nitro" refers to —NO$_2$.

"Sulfonyl" refers herein to the group —SO$_2$—.

"Sulfanyl" refers herein to the group —S—. "Alkylsulfonyl" refers to a substituted sulfonyl of the structure —SO$_2$R$^{12}$ in which R$^{12}$ is alkyl. "Alkylsulfanyl" refers to a substituted sulfanyl of the structure —SR$^{12}$ in which R$^{12}$ is alkyl. Alkylsulfonyl and alkylsulfanyl groups employed in compounds of the present invention include ($C_{1-6}$ alkyl)sulfonyl and ($C_{1-6}$ alkyl)sulfanyl. Thus, typical groups include, for example, methylsulfonyl and methylsulfanyl (i.e., where R$^{12}$ is methyl), ethylsulfonyl, and ethylsulfanyl (i.e., where R$^{12}$ is ethyl), propylsulfonyl, and propylsulfanyl (i.e., where R$^{12}$ is propyl), and the like.

"Hydroxy protecting group" refers to protecting groups for an OH group. The term as used herein also refers to protection of the OH group of an acid COOH. Suitable hydroxy protecting groups as well as suitable conditions for protecting and deprotecting particular functional groups are well known in the art. For example, numerous such protecting groups are described in T. W. Greene and P. G. M. Wuts, Protecting Groups in Organic Synthesis, Third Edition, Wiley, New York, 1999. Such hydroxy protecting groups include $C_{1-6}$ alkyl ethers, benzyl ethers, p-methoxybenzyl ethers, silyl ethers, and the like.

The term "polymorph" refers to the different crystal forms of a compound. Polymorphs can differ from one another in various physical properties such as, for example, differences in their X-ray diffraction patterns, infrared absorption spectroscopy patterns, melting points, stability, or solubility.

"Metabolite" refers to any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. Metabolites corresponding to such derivatives may also be produced by in vitro methods or through synthetic methods. In some embodiments, the metabolite of a compound of Formula (I)-(IV) is an oxide. In some aspects, the oxide is an N-oxide that is formed synthetically by treating a compound of Formula (I)-(IV) with an oxidizing agent. In some aspects the oxidizing agent is N-methylmorpholine N-oxide or a hydroperoxide such as hydrogen peroxide. In some embodiments, a compound of Formula (I)-(IV) is conjugated to glucuronic acid to form a metabolite. In another aspect, provided is a metabolite, tautomer, or stereiosomer thereof having the structure:

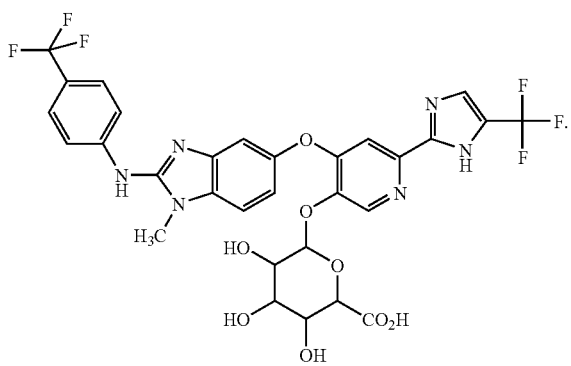

"Optionally substituted" or "substituted" refers to the replacement of one or more hydrogen atoms with a monovalent or divalent radical.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

It is understood that the above definitions are not intended to include impermissible substitution patterns (e.g., methyl substituted with five fluoro groups or a halogen atom substituted with another halogen atom). Such impermissible substitution patterns are well known to the skilled artisan.

It will also be apparent to those skilled in the art that the compounds of the invention, including the compounds of formulas (I), (II), (III), or (IV) or their stereoisomers and polymorphs, as well as the pharmaceutically acceptable salts, esters, metabolites and prodrugs of any of them, may be subject to tautomerization and may therefore exist in various tautomeric forms wherein a proton of one atom of a molecule shifts to another atom and the chemical bonds between the atoms of the molecules are consequently rearranged. See, e.g., March, *Advanced Organic Chemistry: Reactions, Mechanisms and Structures*, Fourth Edition, John Wiley & Sons, pages 69-74 (1992). As used herein, the term "tautomer" refers to the compounds produced by the proton shift, and it should be understood that the all tautomeric forms, insofar as they may exist, are included within the invention.

For instance, the tautomer of a compound of formula (Ia), below which is a compound of formula (I) where c is 1, is a compound of formula (Ib). Similarly, the tautomer of a compound of formula (IVc) is a compound of formula (IVd) or (IVe).

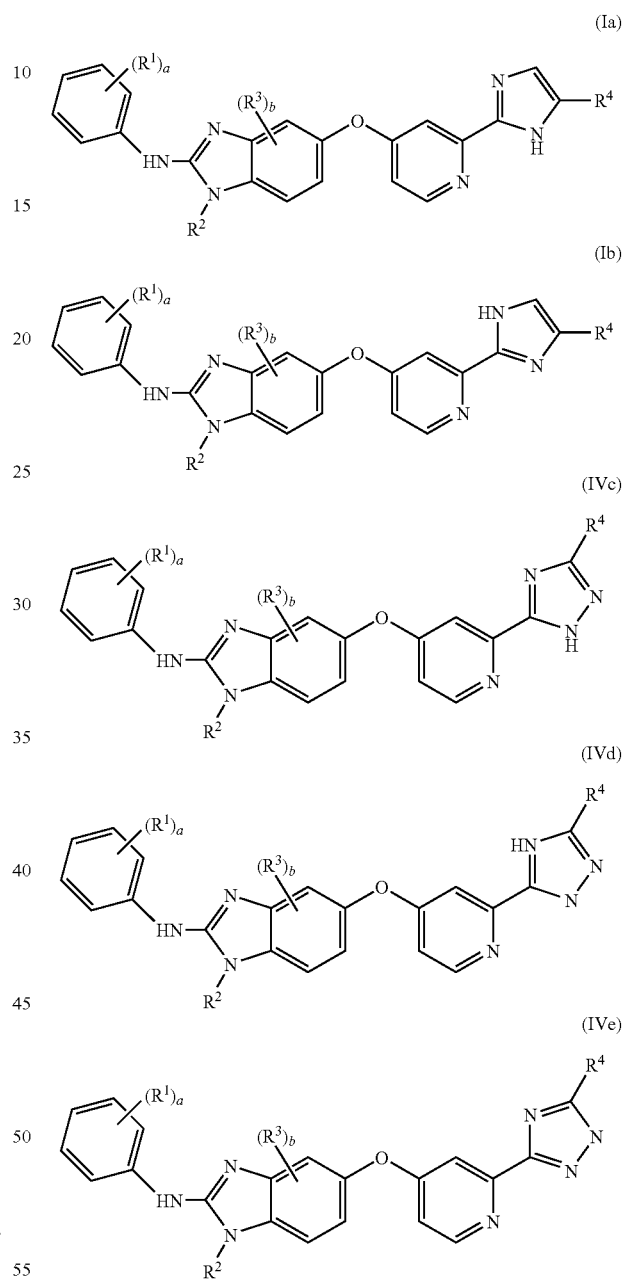

The compounds of the invention, including the compounds of formulas (I), (II), (III), or (IV) or their tautomers and polymorphs, as well as the pharmaceutically acceptable salts, esters, metabolites and prodrugs of any of them, may comprise asymmetrically substituted carbon atoms. Such asymmetrically substituted carbon atoms can result in the compounds of the invention existing in enantiomers, diastereomers, and other stereoisomeric forms that may be defined, in terms of absolute stereochemistry, such as in (R)- or (S)-forms. As a result, all such possible isomers, individual stereoisomers in their optically pure forms, mixtures thereof, racemic mixtures (or "racemates"), mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, Pure Appl. Chem. 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

It will also be apparent to those skilled in the art that the compounds of the invention, including the compounds of formulas (I), (II), (III), or (IV) or their stereoisomers and tautomers, as well as the pharmaceutically acceptable salts, esters, metabolites, and prodrugs of any of them, may exist in various crystalline forms (or "polymorphs") having distinguishing physical properties. It should be understood that the all polymorphs of the compounds of the invention, including their metabolites, prodrugs, stereoisomers, and tautomers, as well as the pharmaceutically acceptable salts of any of them, insofar as they may exist, either in isolated form or as mixtures thereof, are included within the invention.

As used herein, the term "pharmaceutically acceptable salts" refers to the nontoxic acid or alkaline earth metal salts of the compound, tautomer, stereoiosmer, polymorph, ester, metabolite, or prodrug of Formulas (I), (II), (III), or (IV). These salts can be prepared in situ during the final isolation and purification of the compounds of Formulas (I), (II), (III), or (IV), or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, phenyl alkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Salts and formulations of the compounds of the invention are also disclosed in provisional applications titled "Formulations For Benzimidazole Pyridyl Ethers" (U.S. Ser. No. 60/832,715; attorney docket number PP028237.0001) filed on 21 Jul. 2006 and "Salts of Benzimidazolyl Pyridyl Ethers and Formulations Thereof" (attorney docket number PP028258.0001) filed on 30 Aug. 2006 each of which is herein incorporated by reference in its entirety.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of the invention, including the compounds of formulas (I), (II), (III), or (IV) or their tautomers, prodrugs, stereoisomers, and polymorphs, as well as the pharmaceutically acceptable salts, esters and prodrugs of any of them, may be processed in vivo through metabolism in a human or animal body or cell to produce pharmacologically active metabolites that retain activity as inhibitors. The active metabolites of a compound of the invention may be identified using routine techniques known in the art. See, e.g., Bertolini, G. et al., J. Med. Chem. 40:2011-2016 (1997); Shan, D. et al., J. Pharm. Sci. 86(7):765-767; Bagshawe K., Drug Dev. Res. 34:220-230 (1995); Bodor, N., Advances in Drug Res. 13:224-331 (1984); Bundgaard, H., Design of Prodrugs (Elsevier Press 1985); and Larsen, I. K., Design and Application of Prodrugs, Drug Design and Development (Krogsgaard-Larsen et al., eds., Harwood Academic Publishers, 1991). It should be understood that individual chemical compounds that are active metabolites of a compound of the invention are included within the invention.

The term "cancer" refers to cancer diseases that can be beneficially treated by the inhibition of a kinase, particularly Raf kinase, including, for example, solid cancers, such as carcinomas (e.g., of the lungs, pancreas, thyroid, ovarian, bladder, breast, prostate, or colon), melanomas, myeloid disorders (e.g., myeloid leukemia, multiple myeloma, and erythroleukemia), adenomas (e.g., villous colon adenoma), and sarcomas (e.g., osteosarcoma).

In representative embodiments of the invention, the compounds of the invention include, for example, {1-Methyl-5-[2-(5-trifluoromethyl-1H-imidazol-2-yl)-pyridin-4-yloxy]-1H-benzoimidazol-2-yl}-(4-trifluoromethylphenyl)-amine, (2-Fluoro-5-pyridin-3-yl-phenyl)-{1-methyl-5-[2-(5-trifluoromethyl-1H-imidazol-2-yl)-pyridin-4-yloxy]-1H-benzoimidazol-2-yl}-amine, (2-Fluoro-5-pyridin-4-yl-phenyl)-{1-methyl-5-[2-(5-trifluoromethyl-1H-imidazol-2-yl)-pyridin-4-yloxy]-1H-benzoimidazol-2-yl}-amine, (4-tert-Butyl-phenyl)-{1-methyl-5-[2-(5-trifluoromethyl-1H-imidazol-2-yl)-pyridin-4-yloxy]-1H-benzoimidazol-2-yl}-amine, {1-Methyl-5-[2-(5-trifluoromethyl-1H-imidazol-2-yl)-pyridin-4-yloxy]-1H-benzoimidazol-2-yl}-(3-trifluoromethyl-phenyl)-amine, (3-Ethyl-phenyl)-{1-methyl-5-[2-(5-trifluoromethyl-1H-imidazol-2-yl)-pyridin-4-yloxy]-1H-benzoimidazol-2-yl}-amine, (4-Chloro-phenyl)-{1-methyl-5-[2-(5-trifluoromethyl-1H-imidazol-2-yl)-pyridin-4-yloxy]-1H-benzoimidazol-2-yl}-amine, (4-Ethyl-phenyl)-{(1-methyl-5-[2-(5-trifluoromethyl-1H-imidazol-2-yl)-pyridin-4-yloxy-]-1H-benzoimidazol-2-yl}-amine, (4-Chloro-3-trifluoromethyl-phenyl)-{1-methyl-5-[2-(5-trifluoromethyl-1H-imidazol-2-yl)-pyridin-4-yloxy]-1H-benzoimidazol-2-yl}-amine, (4-Fluoro-3-trifluoromethyl-phenyl)-{1-methyl-5-[2-(5-trifluoromethyl-1H-imidazol-2-yl)-pyridin-4-yloxy]-1H-benzoimidazol-2-yl}-amine, {1-Methyl-5-[2-(5-trifluoromethyl-1H-imidazol-2-yl)-pyridin-4-yloxy]-1H-benzoimidazol-2-yl}-(4-trifluoromethoxy-phenyl)-amine, (2-Fluoro-5-trifluoromethyl-phenyl)-(1-methyl-5-(2-[5-methyl-4-(3-trifluoromethyl-phenyl)-1H-imidazol-2-yl]-pyridin-4-yloxy)-1H-benzoimidazol-2-yl)-amine, (2-Fluoro-5-trifluoromethyl-phenyl)-(1-methyl-5-{2-[5-methyl-4-(4-trifluoromethyl-phenyl)-1H-imidazol-2-yl]-pyridin-4-yloxy}-1H-benzoimidazol-2-yl)-amine, 2-{4-[2-(2-Fluoro-5-trifluoromethyl-phenylamino)-1-methyl-1H-benzoimidazol-5-yloxy]-pyridin-2-yl}-5-trifluoromethyl-1H-imidazole-4-carboxylic acid ethyl ester, (2-{4-[2-(2-Fluoro-5-trifluoromethyl-phenylamino)-1-methyl-1H-benzoimidazol-5-yloxy]-pyridin-2-yl}-5-trifluoromethyl-1H-imidazol-4-yl)-methanol, 2-{4-[1-Methyl-2-(4-trifluoromethyl-phenylamino)-1H-benzoimidazol-5-yloxy]-pyridin-2-yl}-3H-imidazole-4-carbonitrile, (3-tert-Butyl-phenyl)-{1-methyl-5-[2-(5-phenyl-1H-imidazol-2-yl)-pyridin-4-yloxy]-1H-benzoimidazol-2-yl}-amine, {1-Methyl-5-[2-(5-phenyl-1H-imidazol-2-yl)-pyridin-4-yloxy]-1H-benzoimidazol-2-yl}-(4-trifluoromethylsulfanyl-phenyl)-amine, (3-tert-Butyl-phenyl)-{1-methyl-5-[2-(5-trifluoromethyl-1H-imidazol-2-yl)-pyridin-4-yloxy]-1H-benzoimidazol-2-yl}-amine,

[4-Fluoro-3-(tetrahydro-furan-3-yl)-phenyl]-{1-methyl-5-[2-(5-trifluoromethyl-1H-imidazol-2-yl)-pyridin-4-yloxy]-1H-benzoimidazol-2-yl}-amine, (4-Bromo-phenyl)-{1-methyl-5-[2-(5-trifluoromethyl-1H-imidazol-2-yl)-pyridin-4-yloxy]-1H-benzoimidazol-2-yl}-amine, (4-Fluoro-3-isopropyl-phenyl)-{1-methyl-5-[2-(5-trifluoromethyl-1H-imidazol-2-yl)-pyridin-4-yloxy]-1H-benzoimidazol-2-yl}-amine, {1-Methyl-5-[2-(5-trifluoromethyl-1H-imidazol-2-yl)-pyridin-4-yloxy]-1H-benzoimidazol-2-yl}-(4-trifluoromethylsulfanyl-phenyl)-amine, (2-Fluoro-5-isopropyl-phenyl)-{1-methyl-5-[2-(5-trifluoromethyl-1H-imidazol-2-yl)-pyridin-4-yloxy]-1H-benzoimidazol-2-yl}-amine, (2-Fluoro-5-trifluoromethyl-phenyl)-{1-methyl-5-[2-(5-trifluoromethyl-1H-imidazol-2-yl)-pyridin-4-yloxy]-1H-benzoimidazol-2-yl}-amine, (5-tert-Butyl-2-fluoro-phenyl)-(1-methyl-5-[2-(5-trifluoromethyl-1H-imidazol-2-yl)-pyridin-4-yloxy]-1H-benzoimidazol-2-yl)-amine, (2-Fluoro-5-trifluoromethyl-phenyl)-{1-methyl-5-[2-(5-methyl-1H-imidazol-2-yl)-pyridin-4-yloxy]-1H-benzoimidazol-2-yl}-amine, (2-Chloro-4-trifluoromethyl-phenyl)-{1-methyl-5-[2-(5-trifluoromethyl-1H-imidazol-2-yl)-pyridin-4-yloxy]-1H-benzoimidazol-2-yl}-amine, 2-{4-[2-(2-Fluoro-5-trifluoromethyl-phenylamino)-1-methyl-1H-benzoimidazol-5-yloxy]-pyridin-2-yl}-3H-imidazole-4-carbonitrile, (5-tert-Butyl-2-chloro-phenyl)-{1-methyl-5-[2-(5-trifluoromethyl-1H-imidazol-2-yl)-pyridin-4-yloxy]-1H-benzoimidazol-2-yl}-amine, (2-Fluoro-5-trifluoromethyl-phenyl)-{1-methyl-5-[2-(4-phenyl-5-trifluoromethyl-1H-imidazol-2-yl)-pyridin-4-yloxy]-1H-benzoimidazol-2-yl}-amine, (2-Chloro-5-trifluoromethyl-phenyl)-{1-methyl-5-[2-(4-phenyl-5-trifluoromethyl-1H-imidazol-2-yl)-pyridin-4-yloxy]-1H-benzoimidazol-2-yl}-amine, {1-Methyl-5-[2-(4-phenyl-5-trifluoromethyl-1H-imidazol-2-yl)-pyridin-4-yloxy]-1H-benzo-imidazol-2-yl}-(3-trifluoromethyl-phenyl)-amine, (3-Ethyl-phenyl)-{1-methyl-5-[2-(4-phenyl-5-trifluoromethyl-1H-imidazol-2-yl)-pyridin-4-yloxy]-1H-benzoimidazol-2-yl}-amine, (4-tert-Butyl-phenyl)-{1-methyl-5-[2-(4-phenyl-5-trifluoromethyl-1H-imidazol-2-yl)-pyridin-4-yloxy]-1H-benzoimidazol-2-yl}-amine, (2-Chloro-5-trifluoromethyl-phenyl)-{1-methyl-5-[2-(5-trifluoromethyl-1H-imidazol-2-yl)-pyridin-4-yloxy]-1H-benzoimidazol-2-yl}-amine, (2-Fluoro-5-trifluoromethyl-phenyl)-{1-methyl-5-[2-(5-methyl-4-phenyl-1H-imidazol-2-yl)-pyridin-4-yloxy]-1H-benzoimidazol-2-yl}-amine, (2-Chloro-5-trifluoromethyl-phenyl)-{1-methyl-5-[2-(5-methyl-4-phenyl-1H-imidazol-2-yl)-pyridin-4-yloxy]-1H-benzoimidazol-2-yl}-amine, (4-tert-Butyl-phenyl)-{1-methyl-5-[2-(5-methyl-4-phenyl-1H-imidazol-2-yl)-pyridin-4-yl-oxy]-1H-benzoimidazol-2-yl}-amine, {1-Methyl-5-[2-(5-methyl-4-phenyl-1H-imidazol-2-yl)-pyridin-4-yloxy]-1H-benzoimidazol-2-yl}-(3-trifluoromethyl-phenyl)-amine,
(5-tert-Butyl-2-fluoro-phenyl)-{1-methyl-5-[2-(5-methyl-4-phenyl-1H-imidazol-2-yl)-pyridin-4-yloxy]-1H-benzoimidazol-2yl}-amine,
[4-(4-Methyl-piperazin-1-yl)-phenyl]-(1-methyl-5-[2-(5-trifluoromethyl-1H-imidazol-2-yl)-pyridin-4-yloxy]-1H-benzoimidazol-2-yl)-amine,
2-{4-[2-(2-Fluoro-5-trifluoromethyl-phenylamino)-1-methyl-1H-benzoimidazol-5-yloxy]-pyridin-2-yl}-3H-imidazole-4-carboxylic, acid methyl ester,
2-{4-[2-(2-Chloro-5-trifluoromethyl-phenylamino)-1-methyl-1H-benzoimidazol-5-yloxy]-pyridin-2-yl}-5-trifluoromethyl-1H-imidazole-4-carboxylic acid ethyl ester,
(2-Fluoro-4-trifluoromethyl-phenyl)-{1-methyl-5-[2-(5-trifluoromethyl-1H-imidazol-2-yl)-pyridin-4-yloxy]-1H-benzoimidazol-2-yl}-amine,
(2-Chloro-phenyl)-{1-methyl-5-[2-(5-trifluoromethyl-1H-imidazol-2-yl)-pyridin-4-yloxy]-1H-benzoimidazol-2-yl}-amine,
(2,5-Dimethoxy-phenyl)-{1-methyl-5-[2-(5-trifluoromethyl-1H-imidazol-2-yl)-pyridin-4-yl-oxy]-1H-benzoimidazol-2-yl}-amine,
(3,5-Dimethoxy-phenyl)-{1-methyl-5-[2-(5-trifluoromethyl-1H-imidazol-2-yl)-pyridin-4-yl-oxy]-1H-benzoimidazol-2-yl}-amine,
{1-Methyl-5-[2-(5-trifluoromethyl-1H-imidazol-2-yl)-pyridin-4-yloxy]-1H-benzoimidazol-2-yl}-(2-trifluoromethyl-phenyl)-amine,
(2-Ethyl-phenyl)-(1-methyl-5-[2-(5-trifluoromethyl-1H-imidazol-2-yl)-pyridin-4-yloxy]-1H-benzoimidazol-2-yl)-amine,
(4-Ethyl-piperazin-1-yl)-(2-{4-[2-(2-fluoro-5-trifluoromethyl-phenylamino)-1-methyl-1H-benzoimidazol-5-yloxy]-pyridin-2-yl}-3H-imidazol-4-yl)-methanone,
2-{4-[2-(2-Fluoro-5-trifluoromethyl-phenylamino)-1-methyl-1H-benzoimidazol-5-yloxy]-pyridin-2-yl}-3H-imidazole-4-carboxylic acid (2-hydroxy-ethyl)-amide,
{1-Ethyl-5-[2-(5-trifluoromethyl-1H-imidazol-2-yl)-pyridin-4-yloxy]-1H-benzoimidazol-2-yl}-(2-fluoro-5-trifluoromethyl-phenyl)-amine,
(2-Fluoro-5-trifluoromethyl-phenyl)-{6-methoxy-1-methyl-5-[2-(5-trifluoromethyl-1H-imidazol-2-yl)-pyridin-4-yloxy]-1H-benzoimidazol-2-yl}-amine,
{6-Methoxy-1-methyl-5-[2-(5-trifluoromethyl-1H-imidazol-2-yl)-pyridin-4-yloxy]-1H-benzoimidazol-2-yl}-(4-trifluoromethyl-phenyl)-amine,
(4-Ethyl-piperazin-1-yl)-(2-{4-[1-methyl-2-(4-trifluoromethyl-phenylamino)-1H-benzo-imidazol-5-yloxy]-pyridin-2-yl}-3H-imidazol-4-yl)-methanone,
{1-Ethyl-5-[2-(5-trifluoromethyl-1H-imidazol-2-yl)-pyridin-4-yloxy]-1H-benzoimidazol-2-yl}-(4-trifluoromethyl-phenyl)-amine,
2-{4-[1-Methyl-2-(4-trifluoromethyl-phenylamino)-1H-benzoimidazol-5-yloxy]-pyridin-2-yl}-3H-imidazole-4-carboxylic acid (2-hydroxy-ethyl)-amide,
2-{1-Methyl-5-[2-(5-trifluoromethyl-1H-imidazol-2-yl)-pyridin-4-yloxy]-1H-benzoimidazol-2-ylamino}-5-trifluoromethyl-phenol,
and 3-{1-Methyl-5-[2-(5-trifluoromethyl-1H-imidazol-2-yl)-pyridin-4-yloxy]-1H-benzo-imidazol-2-ylamino}-6-trifluoromethyl-phenol;

or a tautomer, stereoisomer, polymorph, ester, metabolite, or prodrug thereof or a pharmaceutically acceptable salt of the compound, tautomer, stereoisomer, polymorph, ester, metabolite, or prodrug.

In other aspects, the present invention relates to the processes for preparing the compounds of Formulas (I), (II), (III), or (IV) and to the synthetic intermediates useful in such processes.

The present invention also relates to the processes for preparing the compounds of the invention and to the synthetic intermediates useful in such processes, as described in detail below.

Synthetic Methods

Scheme 1 illustrates construction of the central biaryl ether moiety of the compounds of the invention. Compound 1.1 is reacted with compound 1.2 wherein one of $L^1$ or $L^2$ is halo and the other of $L^1$ or $L^2$ is OH to form ether 1.3. The coupling may be carried out in an organic solvent such as acetonitrile or dimethylsulfoxide in the presence of a base and may also be conducted at elevated or refluxing temperatures. Suitable bases include $K_2CO_3$, $CaCO_3$, KOH, NaOH, or $KF.Al_2O_3$ (*Journal of Organic Chemistry*, Vol. 63, No. 18, 1998 pgs. 6338-6343). The group Q in compound 1.1 may be $NH_2$ or an amino precursor such as $NO_2$ or a protected amino group that can later be converted to the amine by respectively reducing or deprotecting the amino precursors. The Z group in compound 1.2 may be an imidazolyl group substituted with one or two $R^4$ groups or a functional group that can be used to form such an imidazoyl group. Suitable functional groups include an aldehyde, or any aldehyde precursor such as an ester or carbonitrile that can later be converted to the aldehyde. The ester and carbonitrile groups may be reduced to the aldehyde with a reducing agent such as diisobutylaluminum hydride. Z may also be —$CH_2OR^5$, where $R^5$ is a hydroxy protecting group. The aldehyde may be unmasked at a later stage by deprotection of the $R^5$ group and oxidation of the resulting alcohol to the aldehyde. The conversion of the aldehyde to a substituted imidazoyl group is shown in Scheme 3. Other methods for forming the substituted imidazoyl group is shown in Scheme 6.

Scheme 1:

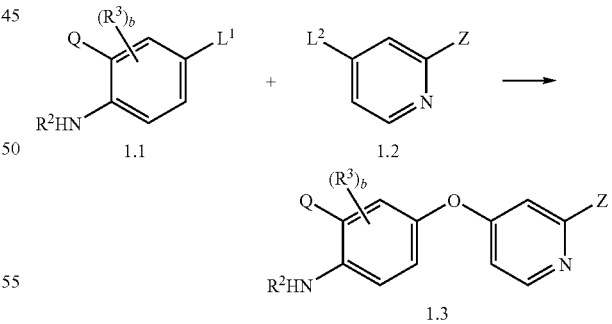

Scheme 2 shows an example of a synthesis of certain biaryl ethers. It is understood that for illustrative purposes, Scheme 2 employs the following substitution patterns: Q is $NO_2$, $L^1$ is OH, $L^2$ is Cl, and Z is a t-butyl ester. An example of the synthesis of aldehyde 2.7 wherein $R^2$ is methyl and b is 0 is shown in Example 1. Amine 2.1 may be converted to alkylamine 2.2 via a number of known methods. In one aspect, amine 2.1 is treated with acetic anhydride and formic acid to form the corresponding formamide that may be reduced to alkyl amine 2.2. Suitable reducing agents include NaBH$_4$ in the presence of BF$_3$(OCH$_2$CH$_3$)$_2$. Alternatively, alkyl amine 2.2 may be synthesized by reacting amine 2.1 with trifluoroacetic anhydride, alkylating the corresponding amide with an alkylating agent such as an alkyl halide, and removing the trifluoroacetamide protecting group by treatment with base such as NaOH.

Chloride 2.5 may be prepared by treating picolinic acid 2.3 with excess thionyl chloride to form acid chloride 2.4 that is then exposed to di-t-butyl dicarbonate and pyridine to give chloride 2.5. Coupling of the alcohol of the alkyl amine 2.2 with chloride 2.5 under basic conditions gives ether 2.6 than can be converted directly to aldehyde 2.7 by reduction with diisobutylaluminum hydride or in two steps by reduction of ester 2.6 to the alcohol followed by oxidation to the aldehyde.

Scheme 2:

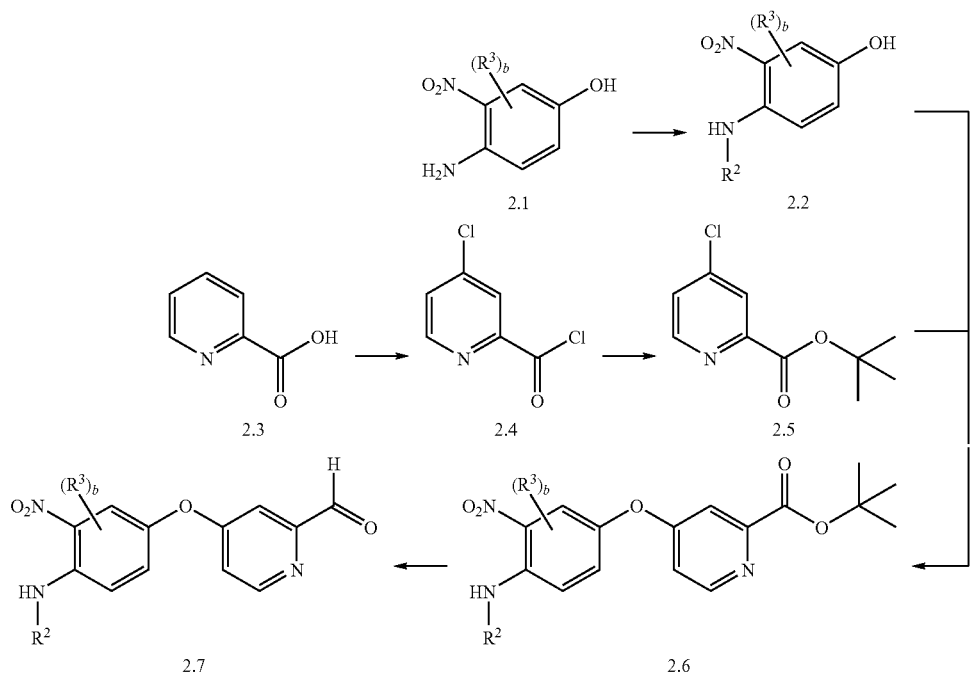

Scheme 3 illustrates the formation of the imidazole ring. Aldehyde 2.7 can be reacted with compound 3.1 wherein $X^b$ is =O or =NHOH and $R^{4p}$ and $R^{4q}$ are independently H or $R^4$, wherein $R^4$ is as previously defined, provided that at least one of $R^{4p}$ and $R^{4q}$ is $R^4$. The reaction may be carried out in a polar solvent such as an ethyl acetate/ethanol mixture and in the presence of NH$_4$OH to provide compound 3.2. The nitro group of compound 3.2 can be reduced to amine 3.3 by treatment with a reducing agent such as sodium dithionite (Na$_2$S$_2$O$_4$).

Scheme 3:

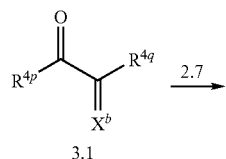

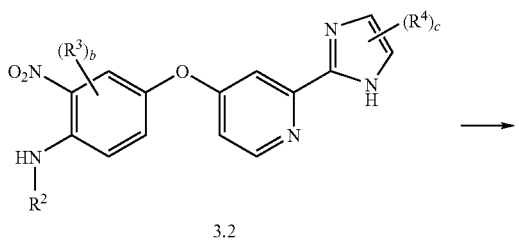

3.2

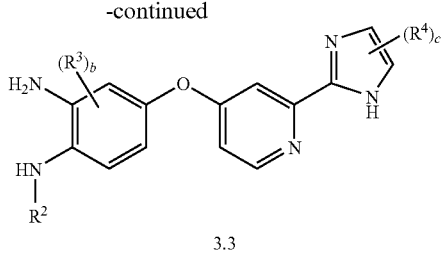

3.3

Schemes 4 illustrates formation of the benzimidazole ring. Diamine 3.3 is reacted with thioisocyanate 4.1 to provide thiourea 4.2. Treatment of 4.2 with a desulfurizing agent gives a compound of Formula (I), The term "desulfurizing agent" refers to agents suitable for effecting ring closure such as FeCl$_3$, 2-chloro-1-methylpyridinium iodide (Mukaiyama reagent), 2-chloro-1,3-dimethylimidazolium chloride, POCl$_3$, or an alkyl halide such as methyl iodide. Modified Mukaiyama reagents may also be used (Journal of Organic Chemistry, Vol. 70, No. 7, 2005 pgs. 2835-2838).

Scheme 4:

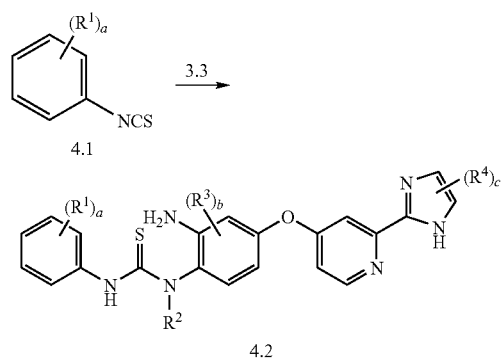

Compounds of the invention may alternatively be synthesized by modifying the sequence of the coupling reactions. Scheme 5 illustrates coupling of 5.1 with 5.2 to form the ether linkage and the coupling of 5.3 with 3.1 to form the imidazole ring as the penultimate step to forming the fully coupled pentacyclic core. For intermediates 5.1 and 5.2, one of $L^3$ or $L^4$ is halo and the other of $L^3$ or $L^4$ is OH. These intermediates may be prepared as shown in the previous schemes by employing suitable starting materials and/or protecting groups in the proper reaction sequences. Such factors are within the skill in the art. Aldehyde 5.3, for example, may be prepared by reduction of the corresponding carbonitrile, the synthesis of which is shown in Example 60, with diisobutylaluminum hydride. Reaction of aldehyde 5.3 according to Scheme 3 above with ketone 3.1 affords compounds of Formula (I).

Compounds of the invention having a triazole terminal group may be prepared as shown in Scheme 6 by reacting compound 6.1 wherein Z is a carbonitrile with hydrazide 6.2. An example of the synthesis of compound 6.3 is described in Example 60.

Scheme 6:

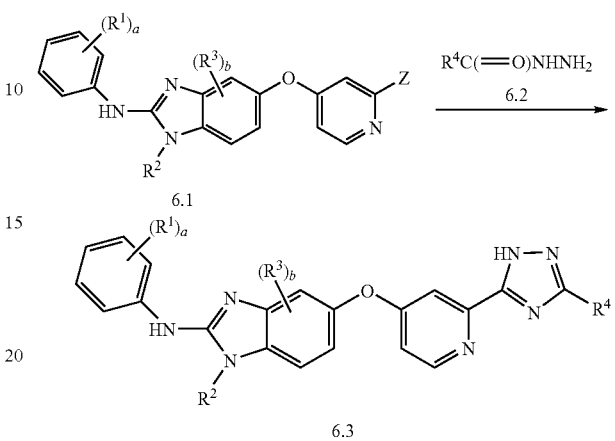

It will be appreciated that the imidazole intermediates used in the coupling reactions can be prepared using other synthetic routes. One such method is shown in Scheme 7. Compound 1.3, where Z is CN, is converted to a compound where Z is an amidino group. This transformation can be effected by reacting 1.3 with an alkoxide, such as methoxide, to convert the carbonitrile to an imidate ester that is next reacted with an ammonium reagent such as ammonium acetate or ammonium benzoate to form the amidine. Reaction of the amidine with compound (Va), wherein $X^a$ is a leaving group, provides the alkylated and cyclized compound 7.2 or a tautomer thereof. Heating compound 7.2 leads to the elimination of water (dehydration) and the formation of intermediate 7.3. Other dehydration conditions include treatment of 7.2 with organic acids such as acetic acid, methanesulfonic acid, camphorsulfonic Scheme 5:

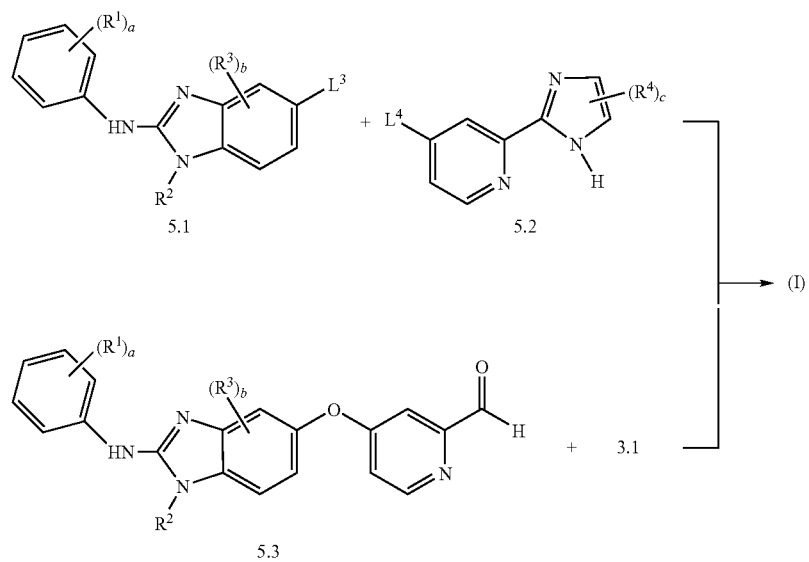

acid, trifluoromethanesulfonic acid, and trifluoroacetic acid, as well as with inorganic acids such as hydrochloric acid and sulfuric acid. The four reactions-formation of imidate ester, formation of amidine, alkylation/cyclization, and dehydration- are typically performed in a one pot sequence.

Scheme 7:

1.3 ⟶

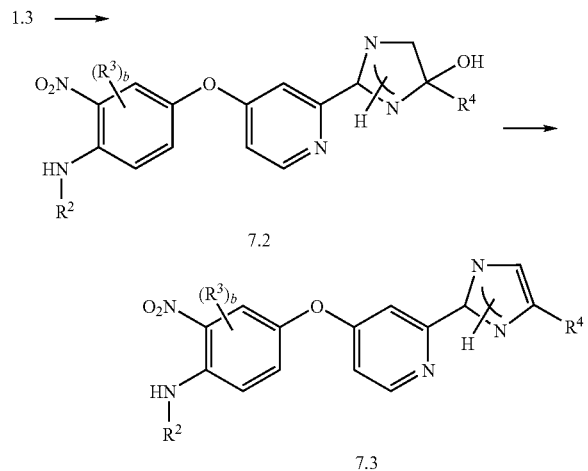

7.2

7.3

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Effective amounts of the compounds of the invention generally include any amount sufficient to detectably inhibit Raf activity by any of the assays described herein, by other Raf kinase activity assays known to or readily ascertained by those having ordinary skill in the art or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

While the compounds of the invention can be administered as the sole active pharmaceutical agent, they can also be used in combination with one or more other agents used in the treatment of cancer. The compounds of the present invention are also useful in combination with known therapeutic agents and anti-cancer agents, and combinations of the presently disclosed compounds with other anti-cancer or chemotherapeutic agents are within the scope of the invention. Examples of such agents can be found in *Cancer Principles and Practice of Oncology*, V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, and agents that interfere with cell cycle checkpoints. The compounds of the invention are also useful when co-administered with radiation therapy.

Therefore, in one embodiment of the invention, the compounds of the invention are also used in combination with known anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Estrogen receptor modulators are compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

Androgen receptor modulators are compounds which interfere with or inhibit the binding of androgens to an androgen receptor. Representative examples of androgen receptor modulators include finasteride and other 5α-reductase inhibitors, nilutamide, flutamide, bicalutamide, liarozole, and abiraterone acetate. Retinoid receptor modulators are compounds which interfere or inhibit the binding of retinoids to a retinoid receptor. Examples of retinoid receptor modulators include bexarotene, tretinoin, 13-cis-retinoic acid, 9-cis-retinoic acid, α-difluoromethylornithine, LX23-7553, trans-N-(4'-hydroxyphenyl) retinamide, and N4-carboxyphenyl retinamide.

Cytotoxic and/or cytostatic agents are compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors, and ubiquitin ligase inhibitors. Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine (chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxy-caminomycin, annamycin, galarubicin, elinafide, MEN10755, and 4-demethoxy-3-deamino-3-aziridinyl-4-methylsulphonyl-daunorubicin (see WO 00/50032). A representative example of a hypoxia activatable compound is tirapazamine. Proteasome inhibitors include, but are not limited to, lactacystin and bortezomib. Examples of microtubule inhibitors/microtubule-stabilizing agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butyl-amide, TDX258, the epothilones (see for example U.S. Pat. Nos. 6,284,781 and 6,288,237) and BMS188797. Representative examples of topoisomerase inhibitors include topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H, 12H-benzo[de]pyrano[3',4':b,7]-indolizino[1,2b]quinoline-10,13 (9H,15H)dione, lurtotecan, 7-[2-(N-isopropylamino)ethyl]-(20S)camptothecin, BNP1350, BNP11100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa, 9b)-9-[2-[N-[2-(dimethylamino)ethyl]-N-methylamino]ethyl]-5-[4-hydroOxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1'-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna. Examples of inhibitors of mitotic kinesins, such as the human mitotic kinesin KSP, are described in PCT Publications WO 01/30768 and WO 01/98278, WO 03/050,064 (Jun. 19, 2003), WO 03/050,122 (Jun. 19, 2003), WO 03/049,527 (Jun. 19, 2003), WO 03/049,679 (Jun. 19, 2003), WO 03/049,678 (Jun. 19, 2003) and WO 03/39460 (May 15, 2003) and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1, and inhibitors of Rab6-KIFL.

Inhibitors of kinases involved in mitotic progression include, but are not limited to, inhibitors of aurora kinase, inhibitors of Polo-like kinases (PLK) (e.g., inhibitors of PLK- 1), inhibitors of bub-1 and inhibitors of bub-R1. Antiproliferative agents include antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofirin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1-diazatetracyclo (7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. Examples of monoclonal antibody targeted therapeutic agents include those therapeutic agents which have cytotoxic agents or radioisotopes attached to a cancer cell specific or target cell specific monoclonal antibody. Examples include, for example, Bexxar. HMG-CoA reductase inhibitors are inhibitors of 3-hydroxy-3-methylglutaryl-CoA reductase. Compounds which have inhibitory activity for HMG-CoA reductase can be readily identified by using assays well-known in the art such as those described or cited in U.S. Pat. No. 4,231,938 and WO 84/02131. Examples of HMG-CoA reductase inhibitors that may be used include, but are not limited to, lovastatin (MEVACOR®; see U.S. Pat. Nos. 4,231,938, 4,294,926, and 4,319,039), simvastatin (ZOCOR®; see U.S. Pat. Nos. 4,444,784, 4,820,850, and 4,916, 239), pravastatin (PRAVACHOL®; see U.S. Pat. Nos. 4,346, 227, 4,537,859, 4,410,629, 5,030,447, and 5,180,589), fluvastatin (LESCOL®; see U.S. Pat. Nos. 5,354,772, 4,911, 165, 4,929,437, 5,189,164, 5,118,853, 5,290,946, and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. In an embodiment, the HMG-CoA reductase inhibitor is selected from lovastatin and simvastatin.

Prenyl-protein transferase inhibitors are compounds which inhibit any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)quinolinone, (−)-6-[amino(4-chlorophenyl)(1-methyl-1H-imidazol-5-yl) methyl]-4-(3-chlorophenyl)-1-methyl-2(1H)-quinolinone, (±)-6-[amino(4-chlorophenyl)(1-methyl-1H-imidazol-5-yl) methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{-[4-hydroxymethyl-4-(4-chloropyridin-2-ylmethyl)-piperidine-1-ylmethyl]-2-methylimidazol-1-ylmethyl}benzonitrile, 4-{-5-[4-hydroxymethyl-4-(3-chlorobenzyl)-piperidine-1-ylmethyl]-2-methylimidazol-1-ylmethyl}benzonitrile, 4-(3-[4-(2-oxo-2H-pyridin-1-yl)benzyl]-3H-imidazol-4-ylmethyl) benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-{3-(2-oxo-1-phenyl-1,2-dihydropyridin-4-ylmethyl)-3H-midazol-4-ylmethyl}benzonitrile, 18,19-dihydro-19-oxo-5H,17H-6,10: 12,16-dimetheno-1H-imidazo[4,3-c][1,11,4]dioxaazacyclononadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H,17H-18,21-ethano-6, 10:12,16-dimetheno-22H-imidazo[3,4-h][1,8,11,14] oxatriazacycloeicosine-9-carbonitrile, and (+−)-19,20-dihydro-3-methyl-1 g-oxo-5H-18,21-ethano-12,14-etheno-6,10-metheno-22H-benzo[d]imidazo[4,3-k][1,6,9,12]oxatriazacyclooctadecine-9-carbonitrile. Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420, 245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571, 792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer* 35(9):1394-1401 (1999).

Angiogenesis inhibitors refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-.alpha., interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS* 89:7384 (1992); *JNCI* 69:475 (1982); *Arch. Opthalmol.* 108: 573 (1990); *Anat Rec.*, (238):68 (1994); *FEBS Letters* 372:83 (1995); *Clin, Orthop.* 313:76 (1995); *J. Mol. Endocrinol.* 16:107 (1996); *Jpn. J. Pharmacol.* 75:105 (1997); *Cancer Res.* 57:1625 (1997); *Cell* 93:705 (1998); *Intl. J. Mol. Med.* 2:715 (1998); *J. Biol. Chem.* 274:9116 (1999)), steroidal anti-inflammatories (such as corticosteroids, mineralocorticoids, dexamethasone, prednisone, prednisolone, methylpred, betamethasone), carboxyamidotriazole, combretastatin A4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, 17:963-968 (October 1999); Kim et al., *Nature*, 362:841-844 (1993); WO 00/44777; and WO 00/61186). Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002). The invention also encompasses combinations of the compounds of the invention with NSAIDs which are selective COX-2 inhibitors (generally defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays). Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference. Representative inhibitors of COX-2 that are useful in the methods of the present invention include 3-phenyl-4-(4-(methylsulfonyl) phenyl)-2-(5H)-furanone; and 5-chloro-3-(4-methylsulfonyl)phenyl-2-(2-methyl-5-pyridinyl)pyridine. Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, U.S. Pat. No. 5,932,598, issued Aug. 3, 1999, U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998. Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3, 5-dichloro-4-(4-chlorobenzoyl)phenyl]methyl]-1H-1,2,3-triazole-4-carboxamide, CM 101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Agents that interfere with cell cycle checkpoints are compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

Inhibitors of cell proliferation and survival signaling pathway are pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY43-9006), inhibitors of MEK (for example CI-1040 and PD-098059) and inhibitors of mTOR (for example Wyeth CCI-779). Such agents include small molecule inhibitor compounds and antibody antagonists.

Apoptosis inducing agents include activators of TNF receptor family members (including the TRAIL receptors).

In certain presently preferred embodiments of the invention, representative agents useful in combination with the compounds of the invention for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, trastuzumab, as well as other cancer chemotherapeutic agents.

The above compounds to be employed in combination with the compounds of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan et al., *J. Biol. Chem.* 276:40888, 2001). As reported by Donovan et al., inhibition of MAPK signaling through treatment with MEK inhibitor changed the phosphorylation status of p27 in hormone refactory breast cancer cell lines and in so doing restored hormone sensitivity. Accordingly, in one aspect, any of the embodiments of the compounds of formulas (I), (II), (III), or (IV) or a tautomer, pharmaceutically acceptable salt, or a pharmaceutically acceptable salt of the tautomer thereof may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-AB1 tyrosine kinase. The afflicted patients are responsive to Gleevec, a small molecule tyrosine kinase inhibitor, as a result of inhibition of Ab1 kinase activity. However, many patients with advanced stage disease respond to Gleevec initially, but then relapse later due to resistance-conferring mutations in the Ab1 kinase domain. In vitro studies have demonstrated that BCR-Av1 employs the Raf kinase pathway to elicit its effects. In addition, inhibiting more than one kinase in the same pathway provides additional protection against resistance-conferring mutations. Accordingly, in another aspect of the invention, any of the embodiments of compounds of formulas (I), (II), (III), or (IV) or a tautomer, pharmaceutically acceptable salt, or a pharmaceutically acceptable salt of the tautomer thereof are used in combination with at least one additional agent, such as Gleevec, in the treatment of hematological cancers, such as chronic myelogenous leukemia (CML), to reverse or prevent resistance to the at least one additional agent.

In another aspect, the present invention relates to methods of inhibiting at least one serine/threonine kinase in the MAPK signaling pathway in a subject, or treating a biological condition mediated by a serine/threonine kinase in the MAPK signaling pathway in a subject, comprising administering a therapeutic composition comprising at least one compound of formulas (I), (II), (III), or (IV) or a tautomer, pharmaceutically acceptable salt, or a pharmaceutically acceptable salt of the tautomer thereof effective to inhibit the activity of the at least one serine/threonine kinase in the MAPK signaling pathway in the subject.

The therapeutic compositions in accordance with this aspect of the invention are useful for treating patients with a need for such inhibitors (e.g., those suffering from cancer mediated by abnormal MAPK signaling). Cancer types mediated by abnormal MAPK signaling include, for example, melanoma, papillary cancer, thyroid cancer, ovarian cancer, colon cancer, pancreatic cancer, non-small cell lung cancer (NSCLC), acute lymphoblastic leukemia (ALL), and acute myeloid leukemia. Abnormal MAPK signaling may be inhibited by administering a compound that inhibits wild-type or mutant forms of Ras, Raf, MEK or ERK.

In one embodiment, the invention provides a method of inhibiting Ras (wild-type or mutant Ras). The method includes administering an effective amount of any of the embodiments of compounds of formulas (I), (II), (III), or (IV) or a tautomer, pharmaceutically acceptable salt, or a pharmaceutically acceptable salt of the tautomer thereof to a subject in need thereof.

In one embodiment, the invention provides a method of inhibiting Raf (wild-type, or mutant B-Raf). The method includes administering an effective amount of a compound any of the embodiments of compounds of formulas (I), (II), (III), or (IV) or a tautomer, pharmaceutically acceptable salt, or a pharmaceutically acceptable salt of the tautomer thereof to a subject in need thereof.

In one embodiment, the invention provides a method of inhibiting MEK. The method includes administering an effective amount of any of the embodiments of compounds of formulas (I), (II), (III), or (IV) or a tautomer, pharmaceutically acceptable salt, or a pharmaceutically acceptable salt of the tautomer thereof to a subject in need thereof.

In one embodiment, the invention provides a method of inhibiting ERK. The method includes administering an effective amount of any of the embodiments of a compound of formulas (I), (II), (III), or (IV) or a tautomer, pharmaceutically acceptable salt, or a pharmaceutically acceptable salt of the tautomer thereof to a subject in need thereof.

An exemplary compound for use in the methods of this aspect of the invention, 1-Methyl-5-[2-(5-trifluoromethyl-1H-imidazol-2-yl)-pyridin-4-yloxy]-1H-benzoimidazol-2-yl}-(4-trifluoro-methyl-phenyl)-amine, exhibited potent inhibition of the MAPK signaling pathway, as described below in Examples 82-86 and 89-90 and shown in FIGS. 6-12B; 14A-C and 15. The compound is a potent inhibitor of B-Raf, c-Raf, mutant B-Raf and mutant Ras in biochemical assays, as shown in Example 82, demonstrating inhibition of mutant B-Raf activity ($IC_{50}$ of 0.0053 μM), inhibition of B-Raf activity ($IC_{50}$ of 0.068 μM) and inhibition of c-Raf activity ($IC_{50}$ of 0.004 μM). Treatment with the compound caused tumor regression in all three mutant B-Raf xenograft models (A375M, MEXF276 and HT29) tested, and tumor growth inhibition in K-Ras and N-Ras driven xenograft models as summarized below in TABLE 7, and described in Examples 84, 85, and 86.

Figure 7A:
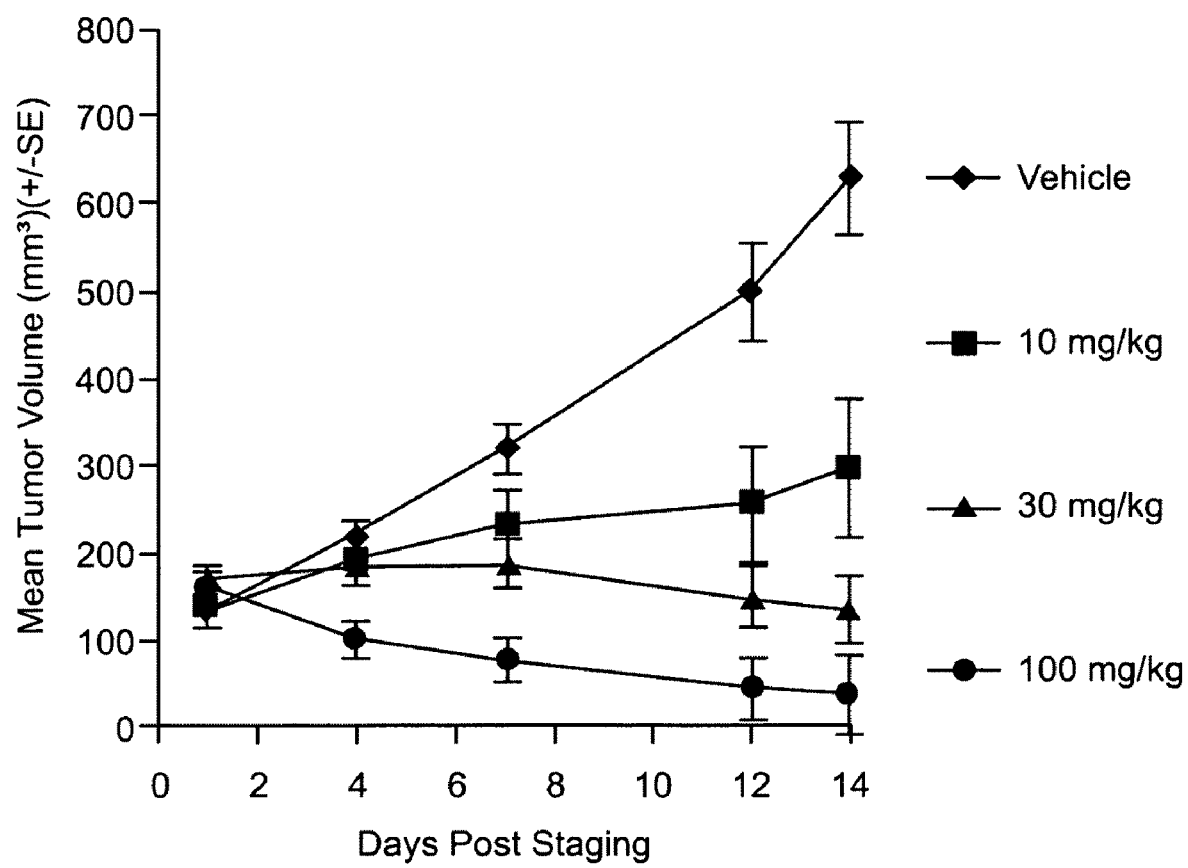
FIG. 7A is a graph showing a dose response in the mean reduction in tumor volume of A375M (B-Raf V600E) human melanoma tumors in mice when treated with an oral dose of 10 mg/kg, 30 mg/kg or 100 mg/kg of the compound of Example 1, as described in Example 84.
Figure 7B:
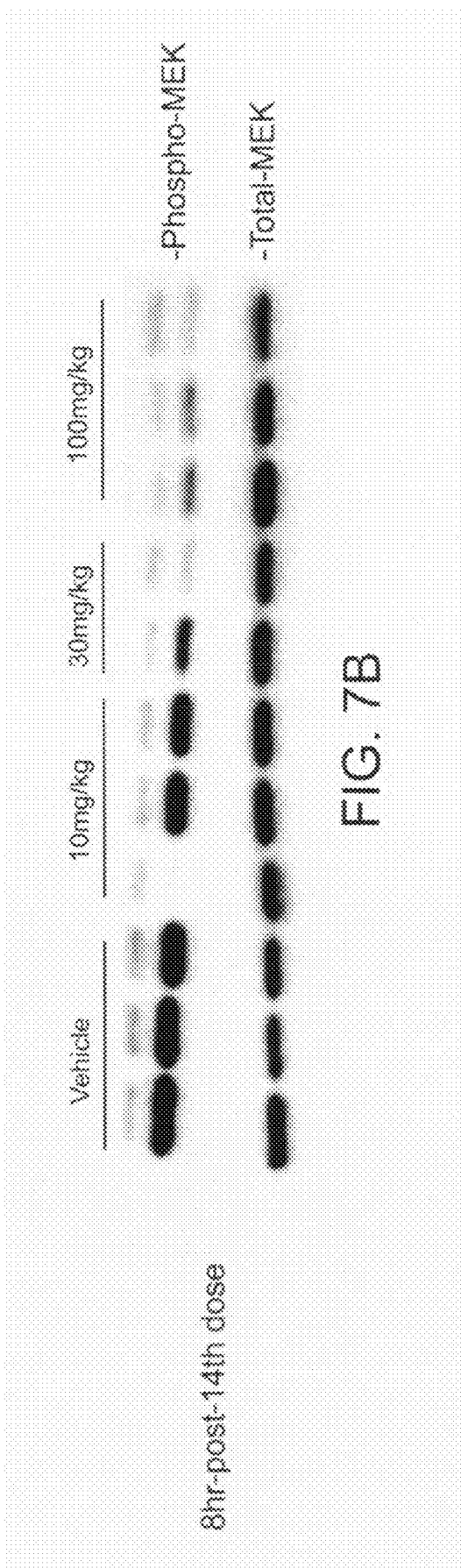
FIG. 7B is a PAGE slide showing the inhibition of downstream signaling from Raf kinase in A375M tumor cells in mice 8 hours after the 14th treatment with the compound of Example 1, as described in Example 84.
Figure 7D:
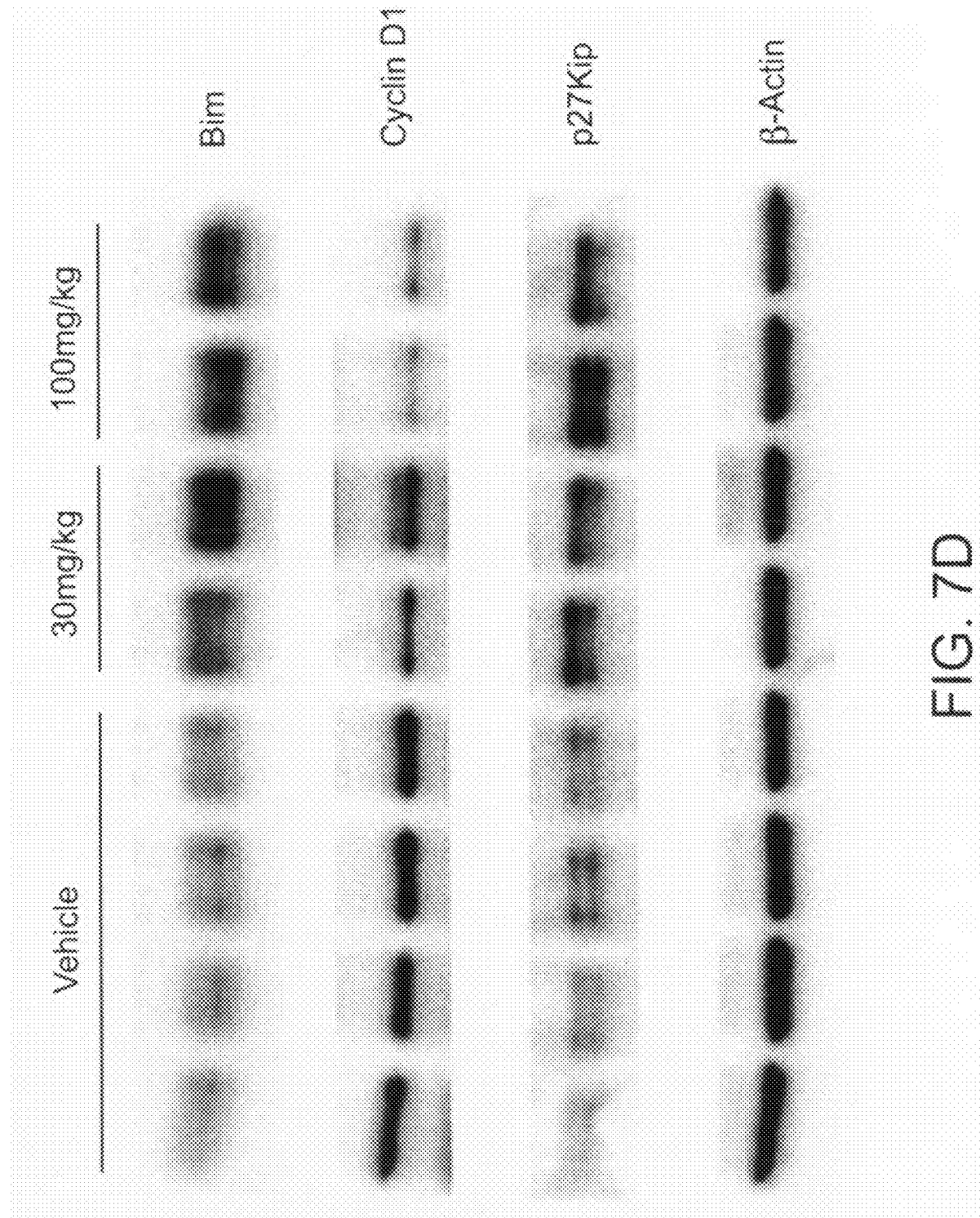
FIG. 7D is a PAGE slide showing the modulation of markers downstream from Raf kinase in A375M tumor cells 24 hours after the 14th treatment with the compound of Example 1, as described in Example 84.
Figure 8A:
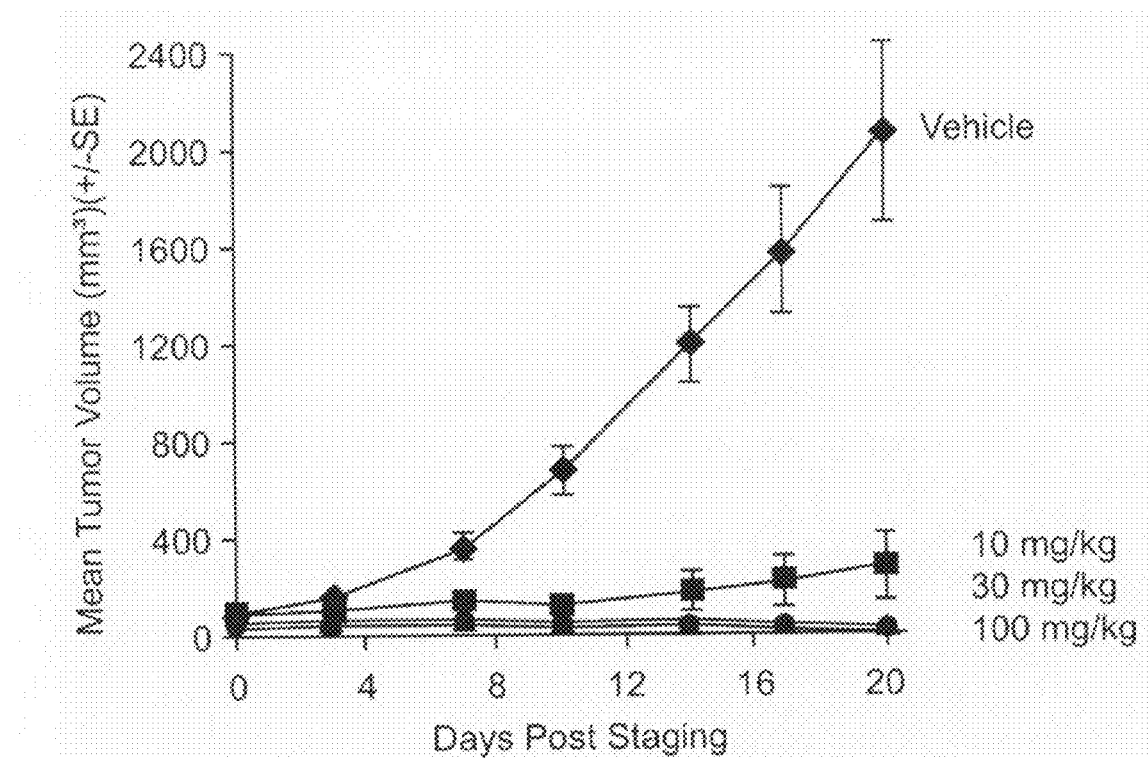
FIG. 8A is a graph showing the mean reduction in tumor volume of MEXF276 (B-Raf V600E) melanoma cancer tumors in mice when treated with the compound of Example 1, as described in Example 85.
Figure 8B:
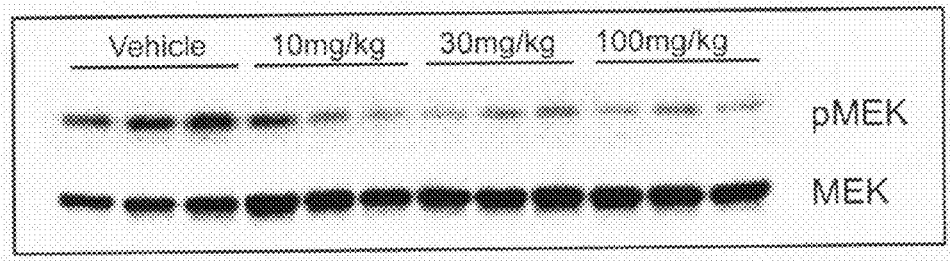
FIG. 8B is a PAGE slide showing the inhibition of downstream signaling from Raf kinase in MEXF276 tumor cells in mice 4 hours after the 20th treatment with the compound of Example 1, as described in Example 85.
Figure 8C:
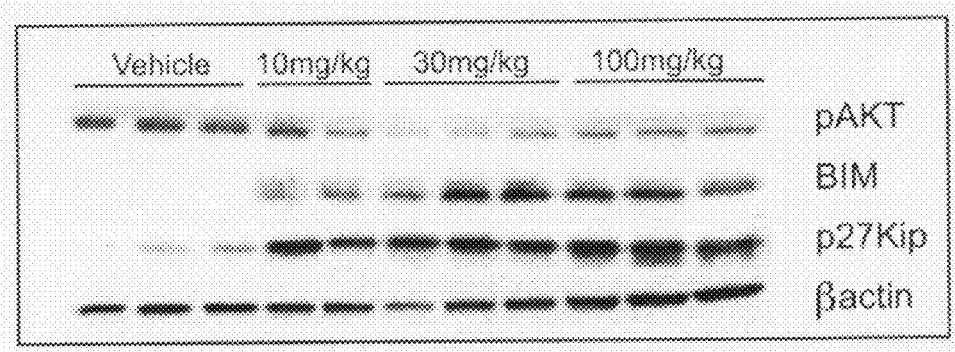
FIG. 8C is a PAGE slide showing the modulation of markers downstream from Raf kinase in MEXF276 tumor cells 4 hours after the 20th treatment with the compound of Example 1, as described in Example 85.
Figure 9C:
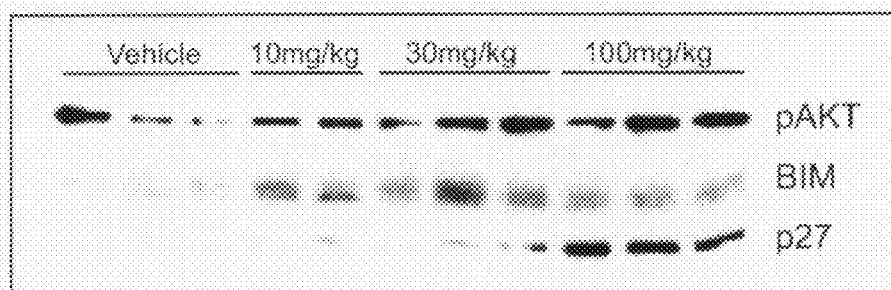
FIG. 9C is a PAGE slide showing the modulation of markers downstream from Raf kinase in MEXF1341 tumor cells 4 hours after the 20th treatment with the compound of Example 1, as described in Example 85.
Figure 10A:
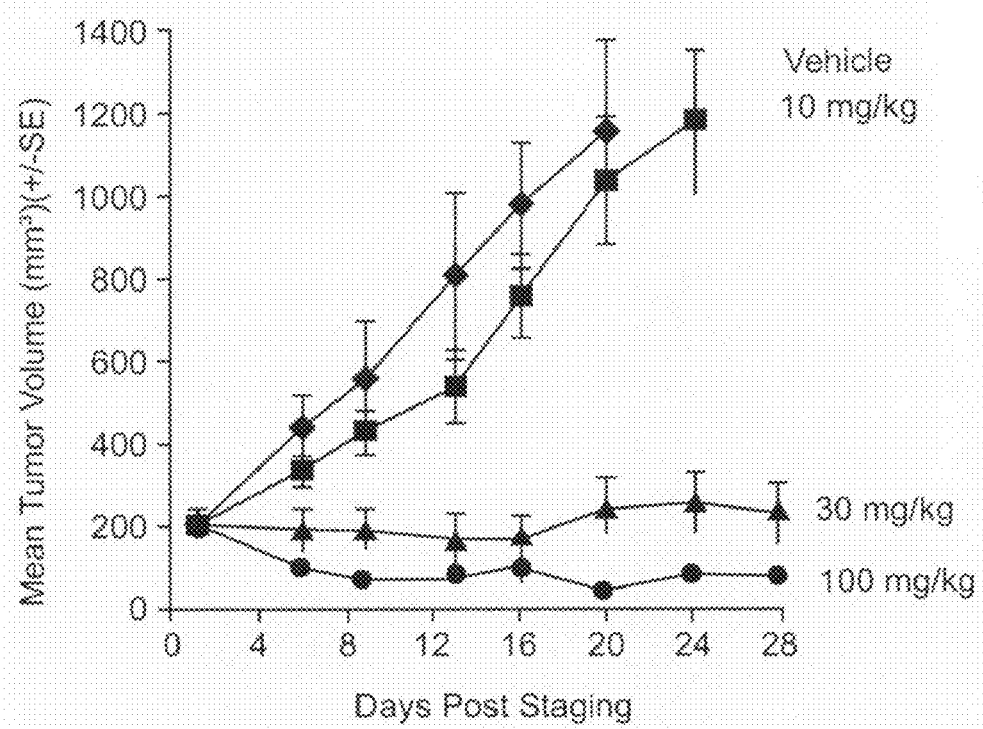
FIG. 10A is a graph showing the mean reduction in tumor volume of HCT-116 (K-Ras G13D) colorectal carcinoma tumors in mice when treated with the compound of Example 1, as described in Example 86.
Figure 10B:
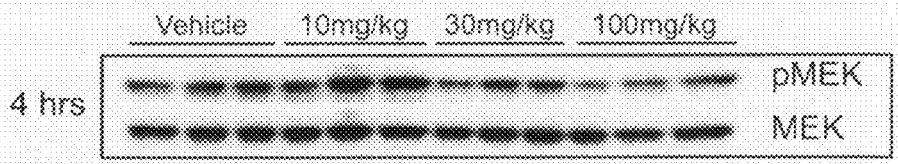
FIG. 10B is a PAGE slide showing the inhibition of downstream signaling from Raf kinase in HCT-116 tumor cells in mice 4 hours after the 3rd treatment with the compound of Example 1, as described in Example 86.
Figure 10C:
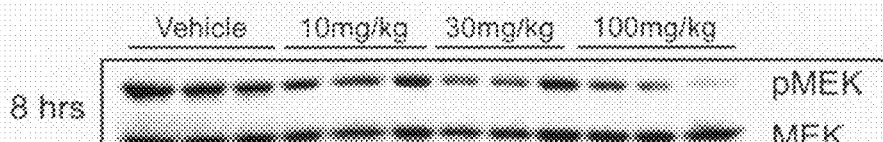
FIG. 10C is a PAGE slide showing the inhibition of downstream signaling from Raf kinase in HCT-116 tumor cells in mice 8 hours after the 3rd treatment with the compound of Example 1, as described in Example 86.

Analysis of target modulation in tumor cells A375M, MEXF276 and HCT-116 after treatment with {1-Methyl-5-[2-(5-trifluoromethyl-1H-imidazol-2-yl)-pyridin-4-yloxy]-1H-benzo-imidazol-2-yl}-(4-trifluoromethyl-phenyl)-amine indicated that phosphorylation of MEK was inhibited in a dose and time-dependant manner, as shown in FIGS. 7B, 8B and 10C. In addition, treatment of tumor cells A375M, MEXF276 and HCT-116 with the compound modulated markers downstream from Raf, including BIM, Cyclin D1, p27Kip and pAKT as shown in FIGS. 7D, 8C and 9C. These assays in preclinical models indicate that {1-Methyl-5-[2-(5-trifluoromethyl-1H-imidazol-2-yl)-pyridin-4-yloxy]-1H-benzoimidazol-2-yl}-(4-trifluoromethyl-phenyl)-amine showed a dose and time dependant inhibition of both MEK target phosphorylation and the signaling molecules downstream from Raf in the MAPK pathway.

In another aspect, the present invention relates to methods of inhibiting at least one tyrosine kinase receptor selected from the group consisting of VEGFR-2, PDGFR-β, pERK, bFGF, FGFR1, FGFR2, FGFR3, c-Kit and CSF-1R in a subject, or treating a biological condition mediated by at least one of VEGFR-2, PDGFR-β, pERK, bFGF, FGFR1, FGFR2, FGFR3, c-Kit and CSF-1R, comprising administering a therapeutic composition comprising at least one compound or a pharmaceutically acceptable salt thereof of formula (I), (II), (III), or (IV) effective to inhibit the tyrosine kinase receptor in the subject.

The therapeutic compounds in accordance with this aspect of the invention are useful for treating patients with a need for such inhibitors (e.g., those suffering from cancer mediated by abnormal tyrosine kinase receptor signaling). Cancers mediated by abnormal tyrosine kinase receptor signaling include, for example, melanoma, breast cancer, bladder cancer, lung cancer, thyroid cancer, prostate cancer, ovarian cancer, mast cell leukemia, germ cell tumors, small-cell lung carcinoma, gastrointestinal stromal tumors, acute myelogenous leukemia (AML), neuroblastoma, and pancreatic cancer.

In one embodiment, the invention provides a method of inhibiting VEGFR-2. The method includes administering an effective amount of a compound, or a pharmaceutically acceptable salt thereof, of any of the embodiments of compounds of formula (I), (II), (III), or (IV) to a subject in need thereof. The method may be useful to treat a solid tumor by inhibiting angiogenesis.

In one embodiment, the invention provides a method of inhibiting PDGFR-β. The method includes administering an effective amount of a compound, or a pharmaceutically acceptable salt thereof, of any of the embodiments of compounds of formula (I), (II), (III), or (IV) to a subject in need thereof.

In one embodiment, the invention provides a method of inhibiting c-Kit. The method includes administering an effective amount of a compound, or a pharmaceutically acceptable salt thereof, of any of the embodiments of compounds of formula (I), (II), (III), or (IV) to a subject in need thereof.

In one embodiment, the invention provides a method of inhibiting CSF-1R. The method includes administering an effective amount of a compound, or a pharmaceutically acceptable salt thereof, of any of the embodiments of compounds of formula (I), (II), (III), or (IV) to a subject in need thereof.

Figure 13:
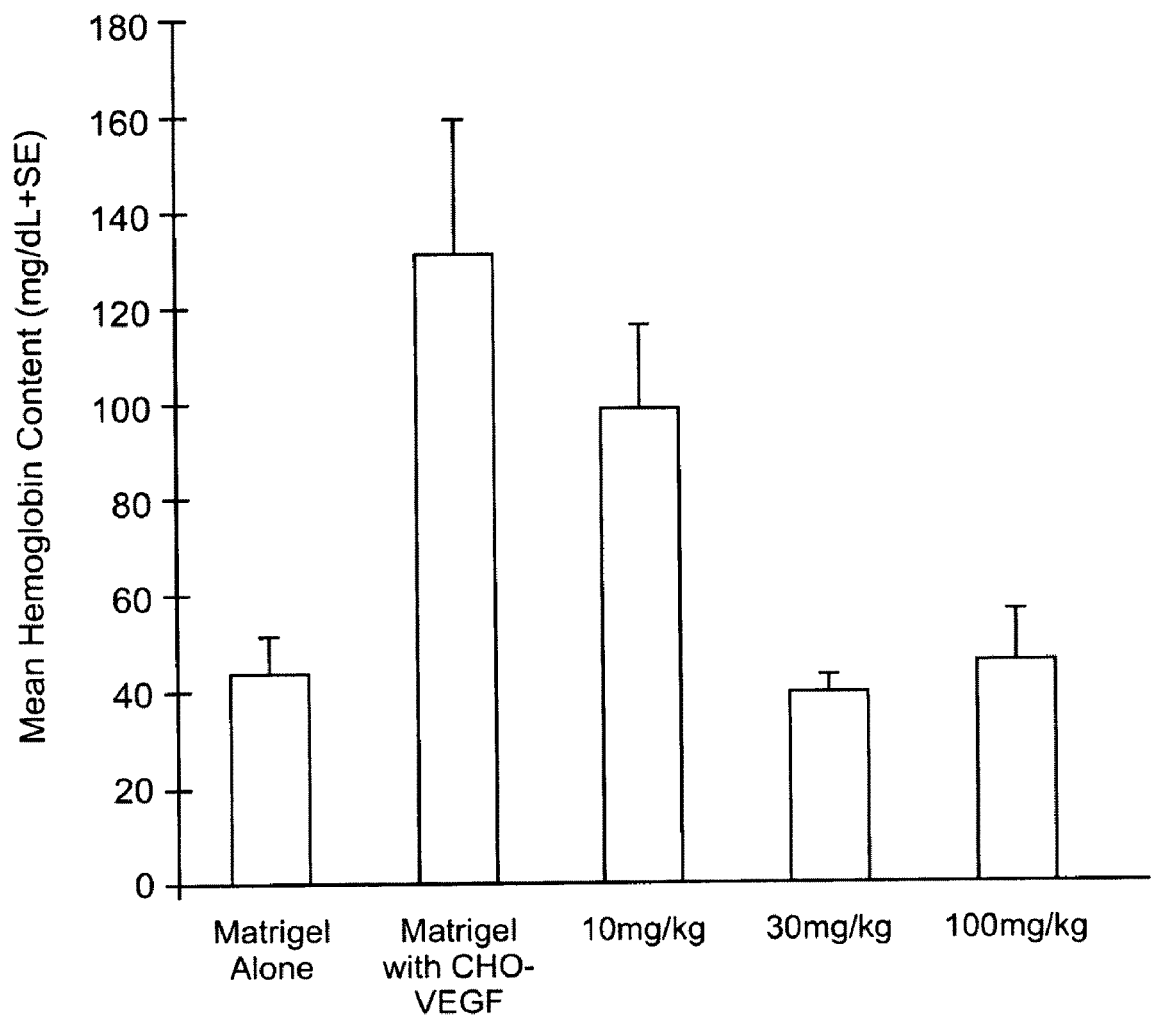
FIG. 13 is a graph showing the inhibition of VEGF-mediated angiogenesis in a CHO-VEGF Matrigel model after treatment with 10 mg/kg, 30 mg/kg, and 100 mg/kg of the compound of Example 1, as described in Example 88.

An exemplary compound for use in the methods of this aspect of the invention, {1-Methyl-5-[2-(5-trifluoromethyl-1H-imidazol-2-yl)-pyridin-4-yloxy]-1H-benzoimidazol-2-yl}-(4-trifluoro-methyl-phenyl)-amine, is a potent inhibitor of tyrosine kinase receptors VEGFR-2, PDGFR-0, pERK, bFGF, FGFR1, FGFR2, FGFR3, c-Kit and CSF-1R in a biochemical assay. The compound demonstrates inhibition of VEGFR-2 activity ($IC_{50}$ of 0.07 µM), inhibition of PDGFR-β ($IC_{50}$ of 0.0032 µM), inhibition of c-Kit ($IC_{50}$ of 0.02 µM), and inhibition of CSF-1R ($IC_{50}$ of 0.20 µM), as described in Example 87. In addition, the compound induced inhibition of angiogenesis in an in vivo matrigel model, as shown in FIG. 13 and described in Example 88.

The present invention will be understood more readily by reference to the following examples, which are provided by way of illustration and are not intended to be limiting of the present invention.

In the Examples below as well as throughout the application, the following abbreviations have the following meanings. If not defined, the terms have their generally accepted meanings.

| | |
|---|---|
| APCI | Atmospheric pressure chemical ionization mass spectroscopy |
| aq. | Aqueous |
| atm | Atmosphere |
| cm | Centimeter |
| ° C. | Degrees Celcius |
| DIPEA | Diisopropylethylamine |
| DMC | 2-Chloro-1,3-dimethylimidazolinium chloride |
| DMSO | Dimethylsulfoxide |
| eq. | equivalent |
| EtOAc | Ethyl Acetate |
| EtOH | Ethanol |
| g or gm | Gram(s) |
| h/hr/hrs | Hour(s) |
| HPLC | High Performance Liquid Chromatography |
| IPA | Isopropyl alcohol |
| L | Liter |
| LCAP | Liquid Chromatography Area Percent |
| LC/MS | Liquid chromatography mass spectroscopy |
| M | Molar |
| MeCN | Acetonitrile |

| | |
|---|---|
| mL | Milliliters |
| NaOMe | Sodium Methoxide |
| 1-PrOH | 1-Propanol |
| TEA | Triethylamine |
| TFAA | Trifluoroacetic anhydride |
| THF | Tetrahydrofuran |

Representative side chains for use in the compounds of the following examples may generally be prepared in accordance with the following procedures:

Example 1

Preparation of {1-Methyl-5-[2-(5-trifluoromethyl-1H-imidazol-2-yl)-pyridin-4-yloxy]-1H-benzo-imidazol-2-yl}-(4-trifluoromethyl-phenyl)-amine

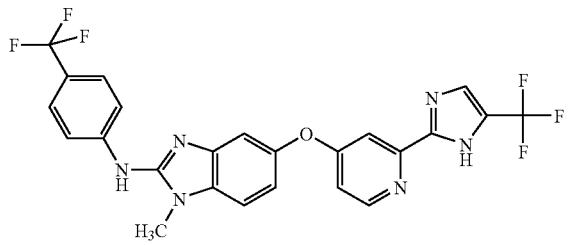

Step 1

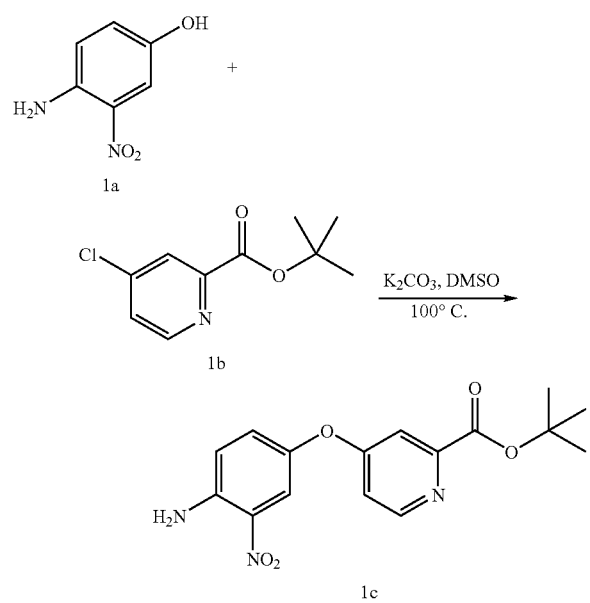

A 500 mL three-neck flask was fitted with a mechanical stirrer and charged with $K_2CO_3$ (4.15 g, 30 mmol). The vessel was sealed, evacuated, and flame dried. The apparatus was allowed to cool to room temperature and purged with argon. To the reaction flask was added 4-amino-3-nitrophenol 1a (3.08 g, 20 mmol), tert-butyl 4-chloropyridine-2-carboxylate 1b (5.2 g, 24 mmol) and dry DMSO (30 mL). The resulting mixture was stirred vigorously and heated to 100° C. for ~14 h. The reaction was poured over iced phosphate buffer (pH=7) and the reaction flask was rinsed well with MTBE (methyl tert butyl ether) and water. The combined biphasic mixture was filtered through Celite (>2 cm pad). The layers were partitioned and separated and the aqueous phase was extracted with MTBE (3×100 mL). The combined organic layers were washed with water (5×100 mL), dried (MgSO$_4$), and evaporated. The crude residue was adsorbed onto SiO$_2$, and purified by flash chromatography (4:1, 2:1, 1:1 hexanes-EtOAc (ethyl acetate)) to furnish 4.92 g (14.9 mmol, 74% yield) of 1c as a yellow brown solid. $^1$H NMR (300 MHz, CDCl$_3$) δ 8.58 (d, J=5.8 Hz, 1 H), 7.90 (d, J=2.8 Hz, 1 H), 7.56 (d, J=2.5 Hz, 1 H), 7.17 (dd, J=2.8, 8.8 Hz, 1 H), 6.94 (dd, J=2.8, 5.8 Hz, 1 H), 6.91 (d, J=9.1 Hz, 1 H), 6.15 (brs, 2 H), 1.62 (s, 9 H); $^{13}$CNMR (75 MHz, CDCl$_3$) δ 165.8, 164.0, 151.8, 151.5, 143.4, 143.2, 131.5, 129.8, 121.0, 118.0, 114.2, 113.1, 83.0, 28.4; mp 163-166° C.

Step 2

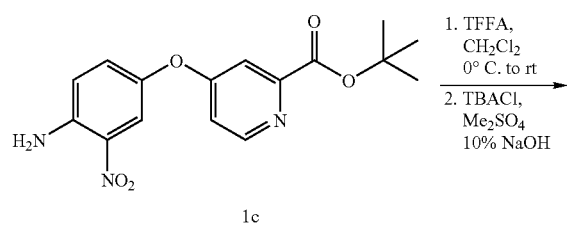

To a solution of the nitroaniline 1c (5.62 g, 17 mmol) in CH$_2$Cl$_2$ (85 mL) at 0° C. was added TFAA (2.4 mL, 3.6 g, 17 mmol). The cooling bath was then removed and the reaction maintained at room temperature for 2 h. The reaction was cooled to 0° C. and TBACl (tetrabutylammonium chloride, 2.5 g, 8.5 mmol), Me$_2$SO$_4$ (dimethylsulfate 3.2 mL, 4.3 g 34 mmol), and 10% NaOH (34 mL) were added. The resulting mixture was stirred vigorously for 4 h at room temperature. The reaction was diluted with water and the resulting layers were partitioned and separated. The aqueous phase was extracted with CH$_2$Cl$_2$ (3×100 mL), and the combined organic layers were washed with brine (2×100 mL), dried (MgSO$_4$), and evaporated. The crude residue was adsorbed onto silica gel and purified by flash chromatography (4:1, 2:1, 1:1, 1:2 hexanes/EtOAc) to give 4.5 g (13.0 mmol, 76%) of 1d as a yellow-orange solid. $^1$H NMR (300 MHz, CDCl$_3$) δ 8.54 (d, J=5.5 Hz, 1H), 8.04 (br d, J=4.7 Hz, 1 H), 7.93 (d, J=2.8 Hz, 1 H), 7.53 (d, J=2.5 Hz, 1 H), 7.25 (app dd, J=2.8, 9.1 Hz, 1 H), 6.91 (m, 2 H), 3.04 (d, J=4.9 Hz, 3 H), 1.59 (s, 9 H); $^{13}$C NMR (75 MHz, CDCl$_3$) δ 165.9, 164.1, 151.5, 144.7, 142.1, 130.4, 118.8, 115.5, 114.1, 112.9, 82.9, 30.4, 28.5; mp 187-189° C.

Step 3

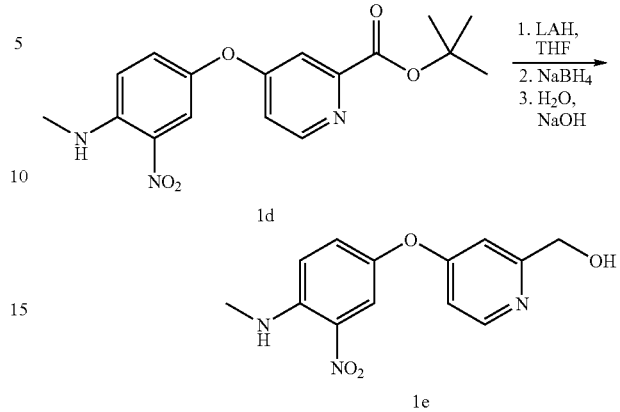

A flame dried 500 mL three necked round bottom flask purged with N$_2$ was charged with LAH (lithium aluminum hydride, 3.0 g, 75 mmol) and dry THF (240 mL). The resulting suspension was cooled to 0° C. and t-butyl ester 1d (20.7 g, 60 mmol) was slowly added while keeping the internal reaction temperature under 5° C. The reaction mixture was then stirred at 0° C. for 2 h followed by stirring at room temperature overnight. NaBH$_4$ (2.27 g, 60 mmol) was added and the reaction mixture was stirred for an additional hour at room temperature. After the reaction was judged complete, the reaction mixture was treated with successive dropwise addition of water (3 mL), 15% NaOH (3 mL), and water (9 mL). The resulting mixture was filtered through Celite, and the remaining solids were washed with EtOAc and methanol. The combined organic portions were evaporated and the resulting crude residue was adsorbed onto SiO$_2$ and purified by flash chromatography (97:3 CH$_2$Cl$_2$—MeOH) to afford 7.63 g (27.7 mmol, 46%) of a red-orange solid as 1e. $^1$H NMR (300 MHz, CDCl$_3$) δ 8.40 (d, J=5.5 Hz, 1 H), 8.05 (br s, 1H), 7.96 (d, J=2.75 Hz, 1 H), 7.29 (d, J=2.75 Hz, 1 H), 6.92 (d, J=9.35 Hz, 1 H), 6.75 (m, 2 H), 4.68 (s, 2 H), 3.07 (d, J=5.23 Hz, 3 H).

Step 4

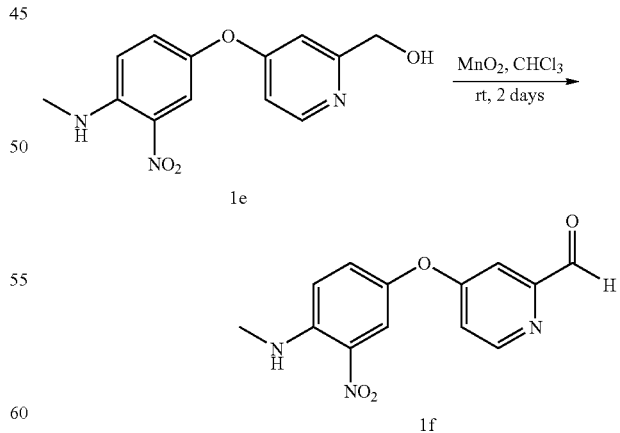

A 100 mL round bottom flask was charged with benzyl alcohol 1e (1.38 g, 5.0 mmol), MnO$_2$ (6.52 g, 75 mmol) and CHCl$_3$ (20 mL). The resulting suspension was stirred at room temperature (rt) for 2 days. The reaction mixture was filtered through Celite, and the remaining solids were washed successively with CHCl₃ and EtOH. The combined organic portions were evaporated, adsorbed onto silica gel, and purified by flash chromatography (98:2 CH₂Cl₂/MeOH) to give 790 mg (2.89 mmol, 58%) of an orange solid as 1f. ¹H NMR (300 MHz, CDCl₃) δ 10.01 (s, 1 H), 8.64 (d, J=5.5 Hz, 1 H), 8.09 (br s, 1 H), 7.96 (d, J=2.75 Hz, 1 H), 7.37 (d, J=2.48 Hz, 1 H), 7.29 (d, J=2.75 Hz, 1 H), 7.08 (dd, J=2.47, 5.5 Hz, 1 H), 6.94 (d, J=9.35 Hz, 1 H), 3.08 (d, J=5.23 Hz, 3 H).

Step 5

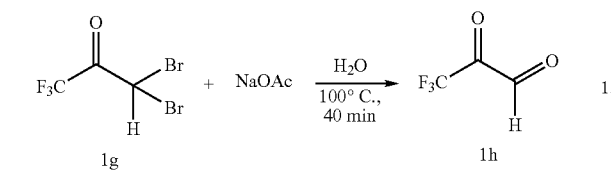

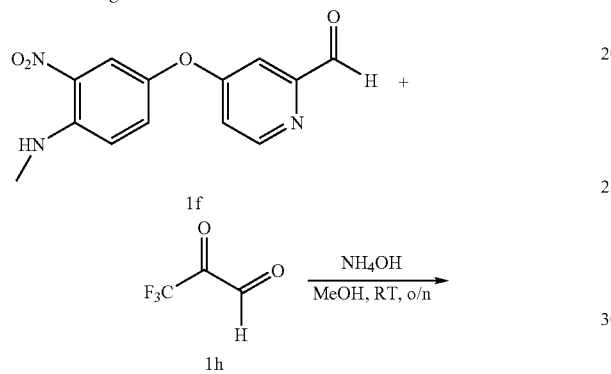

Imidazole ring formation (Baldwin, J. J.; Engelhardt, E. L.; Hirschmann, R.; Lundell, G. F.; Ponticello, G. S. J. Med. Chem. 1979, 22, 687): Compound 1g (Lancaster (Windham, N.H.), 25.75 mL, 136.5 mmol) was added to a solution of NaOAc (22.4 g, 273 mmol) in H₂O (60 mL) and the resulting solution heated to 100° C. for 40 min. After cooling to room temperature (room temperature), the solution of 1h was added to a suspension of 1f (25 g, 91 mmol) in NH₄OH (150 mL) and methanol (450 mL). The resulting mixture was stirred at room temperature overnight. TLC (thin layer chromatography, 95:5 CH₂Cl₂/MeOH) showed complete consumption of 1f. The crude product was concentrated into an aqueous slurry, and partitioned with saturated Na₂CO₃ and CH₂Cl₂. The aqueous phase was extracted three times with CH₂Cl₂, and the combined organics washed with brine, then dried (MgSO₄), and concentrated to give 31.6 g of 1i (83 mmol) as an orange solid (91% yield). No further was purification required.

Other intermediates for preparing substituted imidazoles may be prepared in a similar matter. For example, intermediate 1i² was synthesized following step 5 using 3,3,3-trifluoro-1-phenylpropane-1,2-dione dydrate instead of 1h as shown below as shown below (MeOH=methanol, RT=room temperature, o/n=overnight, min=minutes):

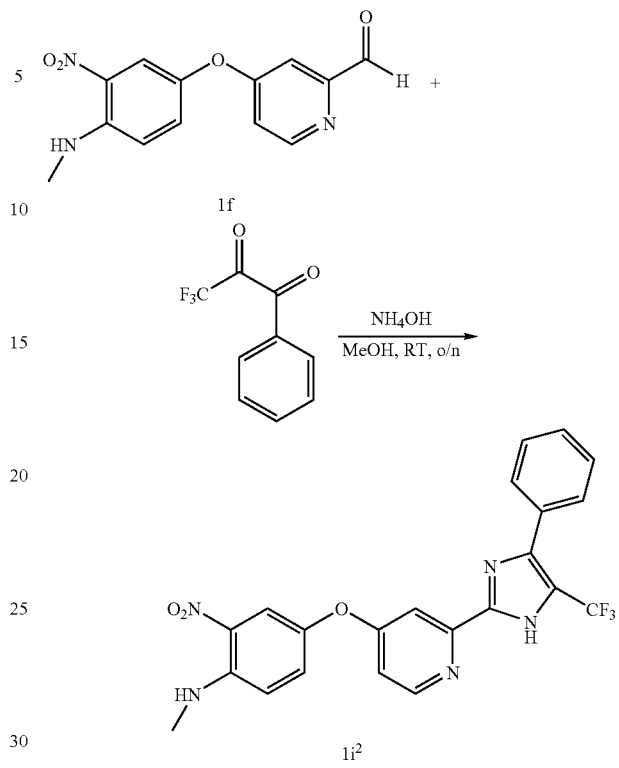

Intermediate 1i³ was synthesized following step 5 using 1-phenyl-1,2-propanedione instead of 1 h as shown below:

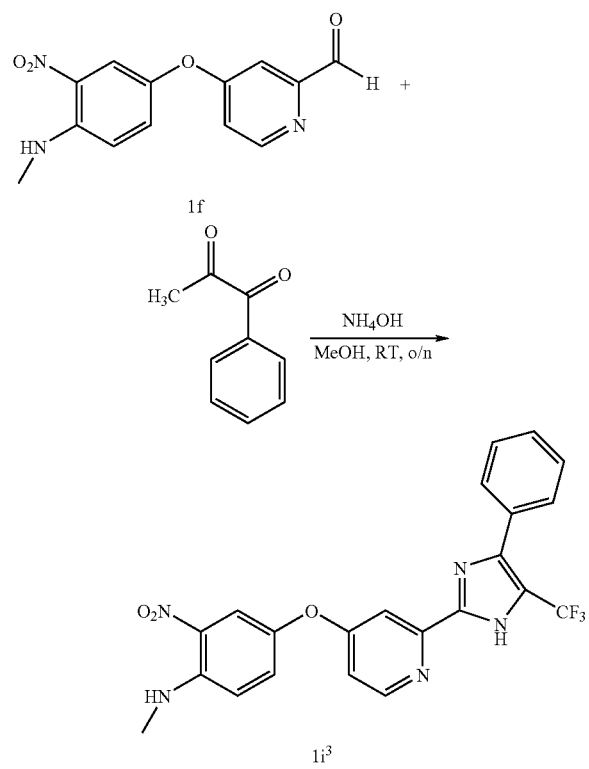

Intermediate 1i⁴ was synthesized following step 5 using 1-(3-trifluoromethylphenyl)-1,2-propanedione or 1-(4-trifluoromethylphenyl)-1,2-propanedione instead of 1h as shown below:

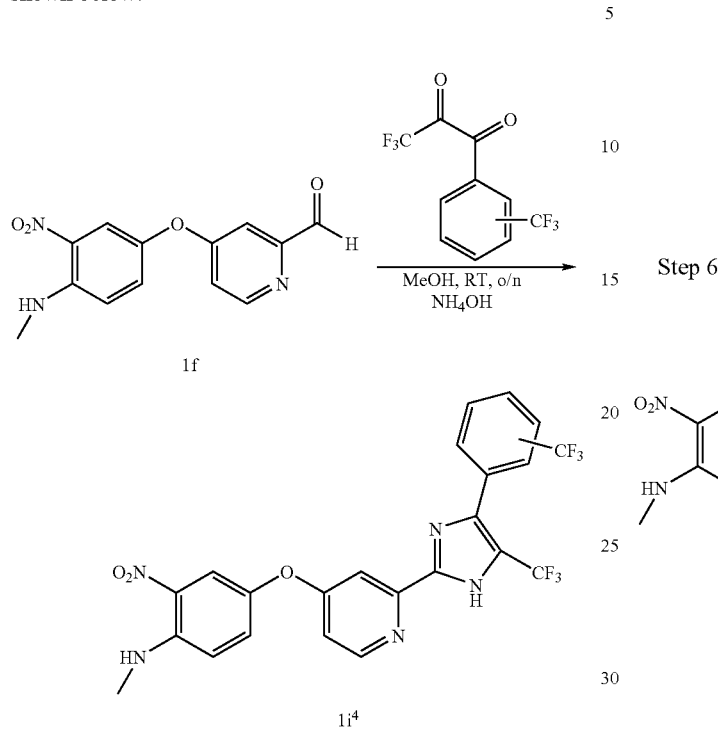

Intermediate 1i⁵ was synthesized following step 5, coupled with procedures in U.S. Pat. No. 5,374,615, using ethyl (2Z)-4,4,4-trifluoro-2-(hydroxyimino)-3-oxobutanoate made from ethyl 4,4,4-trifluoro-3-oxobutanoate instead of 1h as shown below (NMA=N-methyl acetamide):

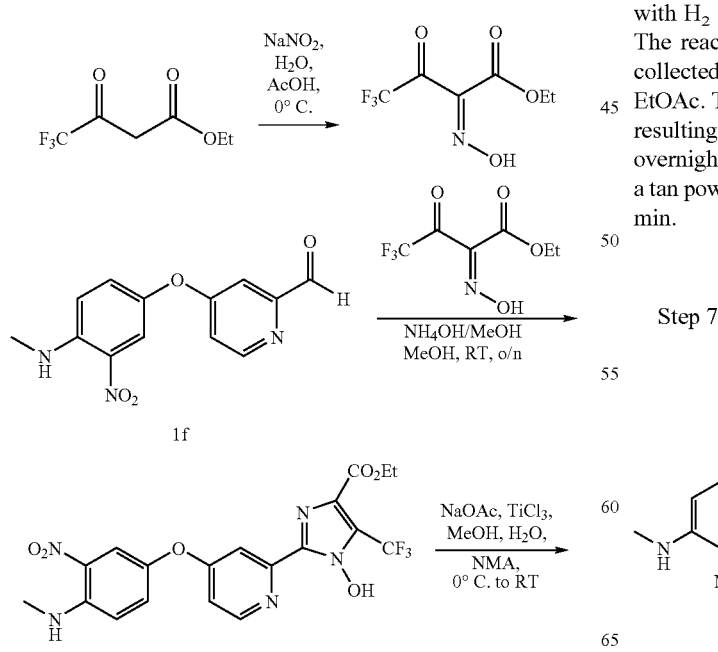

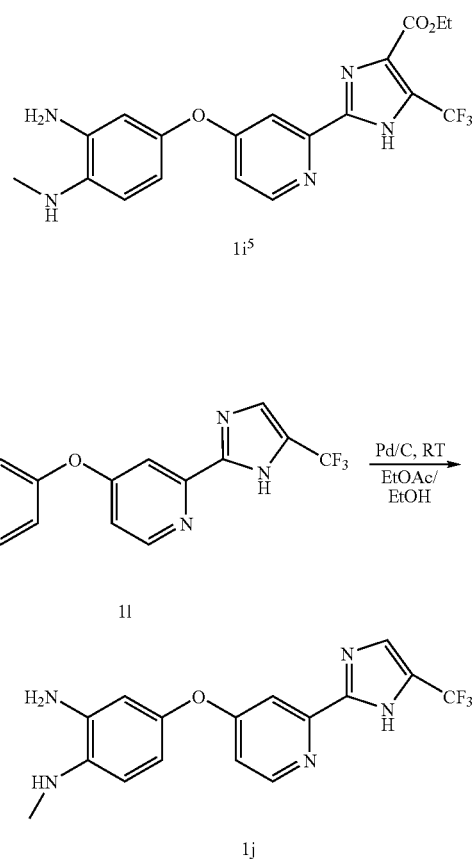

Step 6

A slurry of nitroaniline 1i (45.76 g, 120 mmol) in MeOH (220 mL) and EtOAc (200 mL) was sparged with $N_2$ for 20 min, and then charged with a suspension of 10% Pd/C (12.77 g, 120 mmol) in MeOH (60 mL). The reaction was purged with $H_2$ and maintained under a $H_2$ atmosphere for 2 days. The reaction was filtered through a pad of Celite and the collected solids were washed successively with MeOH and EtOAc. The combined organic filtrates were evaporated, the resulting solid was azeotroped with $CH_2Cl_2$ and then dried overnight under vacuum to give 40.17 g (115 mmol) of 1j as a tan powder (96% yield). LC/MS m/z 336.1 (MH⁺), $t_R$=1.81 min.

Step 7

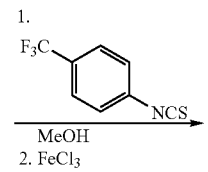

-continued

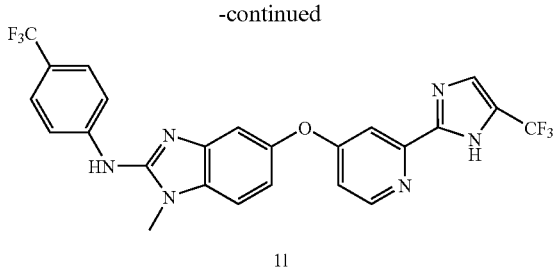

11

4-Trifluoromethylphenyl isothiocyanate (23.37 g, 115 mmol) was added to a stirring solution of diamine 1j (40.17 g, 115 mmol) in MeOH (460 mL) at room temperature. The reaction was maintained at room temperature for 16 h. After the reaction was judged complete, a solution of $FeCl_3$ (20.52 g, 126.5 mmol) in MeOH (50 mL) was added to the reaction and the resulting mixture was stirred at room temperature overnight. The crude reaction mixture was added to a 3 L separatory funnel containing EtOAc (750 mL) and water (750 mL). The layers were separated, and the aqueous phase was extracted with EtOAc (aqueous phase saved). The organic layers were combined, washed with saturated aqueous $Na_2CO_3$ solution, water, and brine, then dried ($MgSO_4$), and concentrated. The saved aqueous phase was made basic (pH=10) by addition of saturated aqueous $Na_2CO_3$ solution and the resulting slurry was added to a 3 L separatory funnel containing EtOAc (500 mL). The mixture was agitated and the resulting emulsion was filtered through filter paper, and the layers were then separated and the aqueous phase was extracted with EtOAc (2×500 mL). The organic layers were combined, washed with brine, then dried ($MgSO_4$), added to previously extracted material and concentrated. The combined product was triturated with $CH_2Cl_2$ (500 mL), adsorbed onto $SiO_2$ and purified by flash chromatography. A final trituration of material with $CH_2Cl_2$ produced {1-methyl-5-[2-(5-trifluoromethyl-1H-imidazol-2-yl)-pyridin-4-yloxy]-1H-benzoimidazol-2-yl}-(4-trifluoromethyl-phenyl)-amine as a pure, white solid. LC/MS m/z 519.1 (MH+); $^1$HNMR (300 MHz, $CDCl_3$) δ 8.44 (d, J=5.5 Hz, 1 H), 7.75 (d, J=8.8 Hz, 2H), 7.61 (dd, J=2.2, 8.5 Hz, 1 H), 7.59 (d, J=8.8 Hz, 2 H), 7.56 (d, J=2.5 Hz, 1 H), 7.38 (app d, J=8.5 Hz, 1 H), 7.23 (d, J=1.9 Hz, 1 H), 6.96 (dd, J=2.2, 8.5 Hz, 1 H), 6.93 (dd, J=2.5, 5.5 Hz, 1 H), 3.76 (s, 3H); LC/MS 1/Z=519.0, $t_R$=2.57 min (MH$^+$); Anal. calc'd for $C_{24}H_{16}F_6N_6O$: C, 55.6; H, 3.11; N, 16.21; Found: C, 55.81; H, 3.43; N, 16.42; mp: 217-220° C.

Example 2

Preparation of (2-Fluoro-5-pyridin-3-yl-phenyl)-{1-methyl-5-[2-(5-trifluoromethyl-1H-imidazol-2-yl)-pyridin-4-yloxy]-1H-benzoimidazol-2-yl}-amine

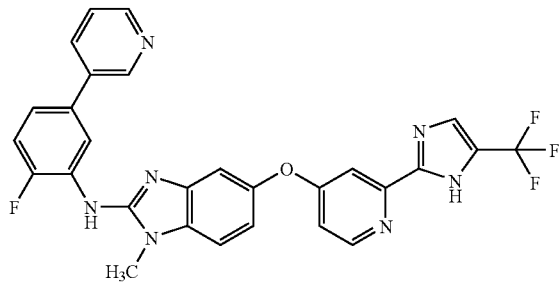

(2-Fluoro-5-pyridin-3-yl-phenyl)-{1-methyl-5-[2-(5-trifluoromethyl-1H-imidazol-2-yl)-pyridin-4-yloxy]-1H-benzoimidazol-2-yl}-amine was synthesized as described above in Step 7 of Example 1 using 3-(4-Fluoro-3-isothiocyanato-phenyl)-pyridine. LC/MS m/z 546.1 (MH$^+$), $R_t$ 1.82 min.

Example 3

Preparation of (2-Fluoro-5-pyridin-4-yl-phenyl)-{1-methyl-5-[2-(5-trifluoromethyl-1H-imidazol-2-yl)-pyridin-4-yloxy]-1H-benzoimidazol-2-yl}-amine

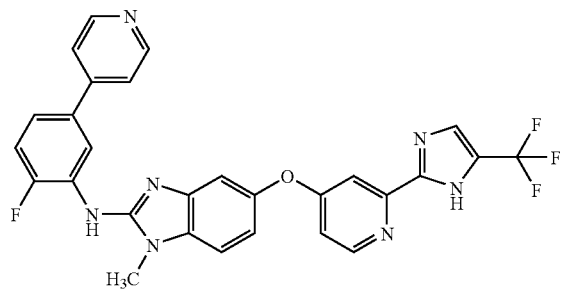

(2-Fluoro-5-pyridin-4-yl-phenyl)-{1-methyl-5-[2-(5-trifluoromethyl-1H-imidazol-2-yl)-pyridin-4-yloxy]-1H-benzoimidazol-2-yl}-amine was synthesized as described above in Step 7 of Example 1 using 4-(4-Fluoro-3-isothiocyanato-phenyl)-pyridine. LC/MS m/z 546.5 (MH$^+$), $R_t$ 1.83 min.

Example 4

Preparation of (4-tert-Butyl-phenyl)-(1-methyl-5-[2-(5-trifluoromethyl-1H-imidazol-2-yl)-pyridin-4-yloxy]-1H-benzoimidazol-2-yl)-amine

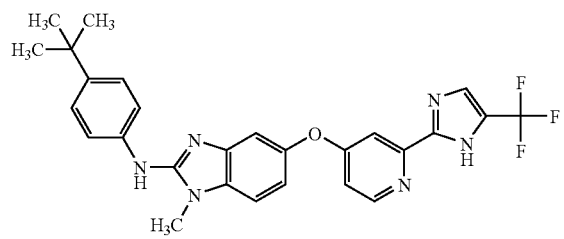

(4-tert-Butyl-phenyl)-{1-methyl-5-[2-(5-trifluoromethyl-1H-imidazol-2-yl)-pyridin-4-yl-oxy]-1H-benzoimidazol-2-yl}-amine was synthesized as described above in Step 7 of Example 1 using 4-tert-butylphenylisothiocyanate. LC/MS m/z 425.4 (MH$^+$), $R_t$ 2.56 min.

Example 5

Preparation of ({1-Methyl-5-[2-(5-trifluoromethyl-1H-imidazol-2-yl)-pyridin-4-yloxy]-1H-benzo-imidazol-2-yl}-(3-trifluoromethyl-phenyl)-amine

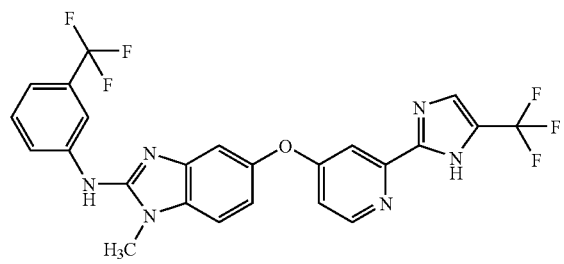

{1-Methyl-5-[2-(5-trifluoromethyl-1H-imidazol-2-yl)-pyridin-4-yloxy]-1H-benzoimidazol-2-yl}-(3-trifluoromethyl-phenyl)-amine was synthesized as described above in Step 7 of Example 1 using 3-(trifluoromethyl)phenylisothiocyanate. LC/MS m/z 519.4 (MH⁺), $R_t$ 2.36 min.

Example 6

Preparation of (3-Ethyl-phenyl)-{1-methyl-5-[2-(5-trifluoromethyl-1H-imidazol-2-yl)-pyridin-4-yloxy]-1H-benzoimidazol-2-yl}-amine

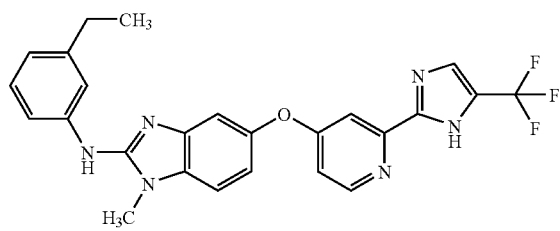

(3-Ethyl-phenyl)-{1-methyl-5-[2-(5-trifluoromethyl-1H-imidazol-2-yl)-pyridin-4-yloxy]-1H-benzoimidazol-2-yl}-amine was synthesized as described in Step 7 of Example 1 using 3-ethyl phenylisothiocyanate. LC/MS m/z 479.4 (MH⁺), $R_t$ 2.32 min.

Example 7

Preparation of (4-Chloro-phenyl)-{1-methyl-5-[2-(5-trifluoromethyl-1H-imidazol-2-yl)-pyridin-4-yloxy]-1H-benzoimidazol-2-yl}-amine

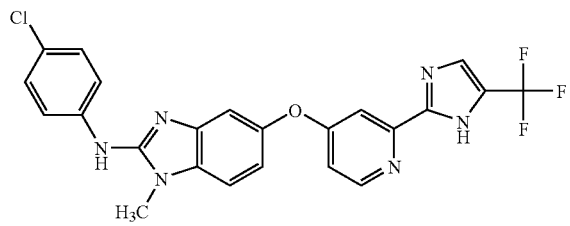

(4-Chloro-phenyl)-{1-methyl-5-[2-(5-trifluoromethyl-1H-imidazol-2-yl)-pyridin-4-yloxy]-1H-benzoimidazol-2-yl}-amine was synthesized as described above in Step 7 of Example 1 using 4-chlorophenylisothiocyanate. LC/MS m/z 485.4 (MH⁺); $R_t$ 2.23 min.

Example 8

Preparation of (4-Ethyl-phenyl)-{1-methyl-5-[2-(5-trifluoromethyl-1H-imidazol-2-yl)-pyridin-4-yloxy]-1H-benzoimidazol-2-yl}-amine

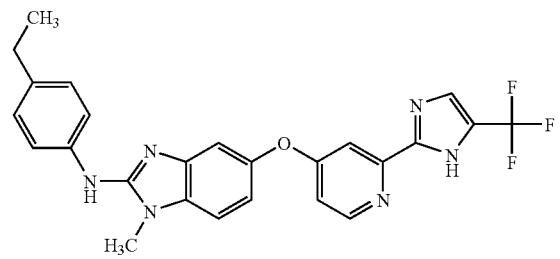

(4-Ethyl-phenyl)-{1-methyl-5-[2-(5-trifluoromethyl-1H-imidazol-2-yl)-pyridin-4-yloxy]-1H-benzoimidazol-2-yl}-amine was synthesized as described above in Step 7 of Example 1 using 4-ethylphenylisothiocyanate. LC/MS m/z 479.5 (MH⁺), $R_t$ 2.31 min.

Example 9

Preparation of (4-Chloro-3-trifluoromethyl-phenyl)-{1-methyl-5-[2-(5-trifluoromethyl-1H-imidazol-2-yl)-pyridin-4-yloxy]-1H-benzoimidazol-2-yl}-amine

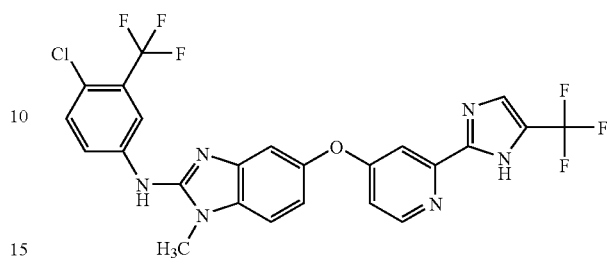

(4-Chloro-3-trifluoromethyl-phenyl)-{1-methyl-5-[2-(5-trifluoromethyl-1H-imidazol-2-yl)-pyridin-4-yloxy]-1H-benzoimidazol-2-yl}-amine was synthesized as described above in Step 7 of Example 1 using 4-chloro-3-(trifluoromethyl)phenylisothiocyanate. LC/MS m/z 553.4 (MH⁺), $R_t$ 2.51 min.

Example 10

Preparation of (4-Fluoro-3-trifluoromethyl-phenyl)-{1-methyl-5-[2-(5-trifluoromethyl-1H-imidazol-2-yl)-pyridin-4-yloxy]-1H-benzoimidazol-2-yl}-amine

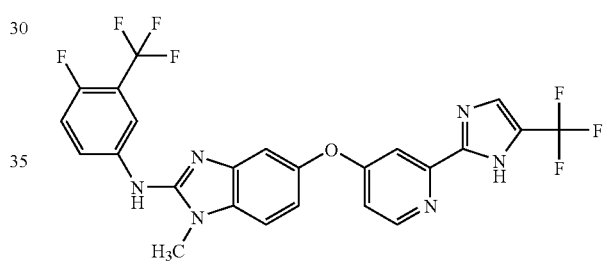

(4-Fluoro-3-trifluoromethyl-phenyl)-{1-methyl-5-[2-(5-trifluoromethyl-1H-imidazol-2-yl)-pyridin-4-yloxy]-1H-benzoimidazol-2-yl}-amine was synthesized as described above in Step 7 of Example 1 using 4-fluoro-3-(trifluoromethyl)phenylisothiocyanate. LC/MS m/z 537.4 (H⁺), $R_t$ 2.40 min.

Example 11

Preparation of {1-Methyl-5-[2-(5-trifluoromethyl-1H-imidazol-2-yl)-pyridin-4-yloxy]-1H-benzo-imidazol-2-yl}-(4-trifluoromethoxy-phenyl)-amine

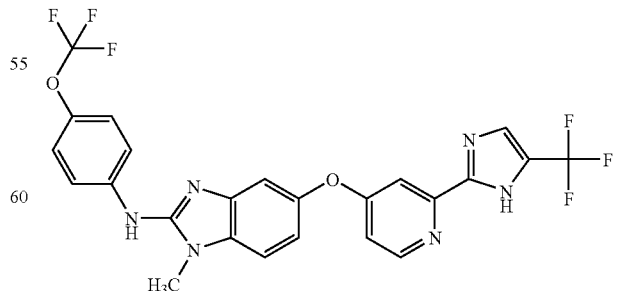

{1-Methyl-5-[2-(5-trifluoromethyl-1H-imidazol-2-yl)-pyridin-4-yloxy]-1H-benzoimidazol-2-yl}-(4-trifluoromethoxy-phenyl)-amine was synthesized as described above in Step 7 of Example 1 using 4-(trifluoromethoxy) phenylisothiocyanate. LC/MS m/z 535.4 (MH⁺), R_t 2.24 min.

Example 12

Preparation of (2-Fluoro-5-trifluoromethyl-phenyl)-(1-methyl-5-{2-[5-methyl-4-(3-trifluoromethyl-phenyl)-1H-imidazol-2-yl]-pyridin-4-yloxy}-1H-benzoimidazol-2-yl)-amine

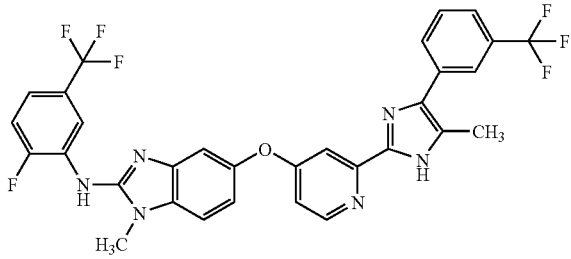

(2-Fluoro-5-trifluoromethyl-phenyl)-(1-methyl-5-{2-[5-methyl-4-(3-trifluoromethyl-phenyl)-1H-imidazol-2-yl]-pyridin-4-yloxy}-1H-benzoimidazol-2-yl)-amine was synthesized using similar procedures as described above in Example 1 using 2-Fluoro-5-(trifluoromethyl)phenyl isothiocyanate. LC/MS m/z 627.5 (MH⁺), R_t 2.79 min.

Example 13

Preparation of (2-Fluoro-5-trifluoromethyl-phenyl)-(1-methyl-5-{2-[5-methyl-4-(4-trifluoromethyl-phenyl)-1H-imidazol-2-yl]-pyridin-4-yloxy}-1H-benzoimidazol-2-yl)-amine

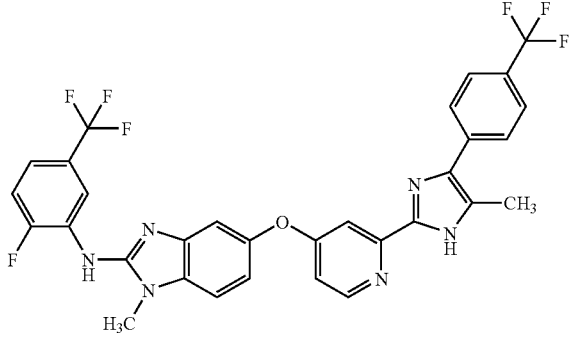

(2-Fluoro-5-trifluoromethyl-phenyl)-(1-methyl-5-{2-[5-methyl-4-(4-trifluoromethyl-phenyl)-1H-imidazol-2-yl]-pyridin-4-yloxy}-1H-benzoimidazol-2-yl)-amine was synthesized using similar procedures as described above in Example 1 using 2-Fluoro-5-(trifluoromethyl)phenyl isothiocyanate. LC/MS m/z 627.5 (MH⁺), R_t 2.79 min.

Example 14

Preparation of 2-{4-[2-(2-Fluoro-5-trifluoromethyl-phenylamino)-1-methyl-1H-benzoimidazol-5-yloxy]-pyridin-2-yl}5-trifluoromethyl-1H-imidazole-4-carboxylic Acid Ethyl Ester

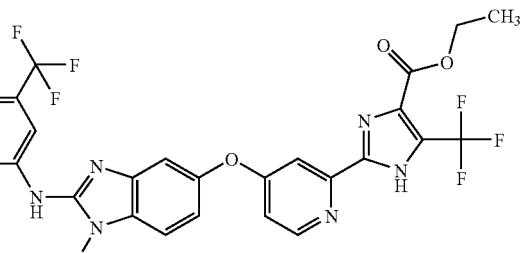

2-{4-[2-(2-Fluoro-5-trifluoromethyl-phenylamino)-1-methyl-1H-benzoimidazol-5-yloxy]-pyridin-2-yl}-5-trifluoromethyl-1H-imidazole-4-carboxylic acid ethyl ester was synthesized using similar procedures as described above in Example 1 using 2-Fluoro-5-(trifluoromethyl)phenyl isothiocyanate. LC/MS m/z 609.5 (H⁺).

Example 15

Preparation of (2-{4-[2-(2-Fluoro-5-trifluoromethyl-phenylamino)-1-methyl-1H-benzo-imidazol-5-yloxy]-pyridin-2-yl}-5-trifluoromethyl-1H-imidazol-4-yl)-methanol

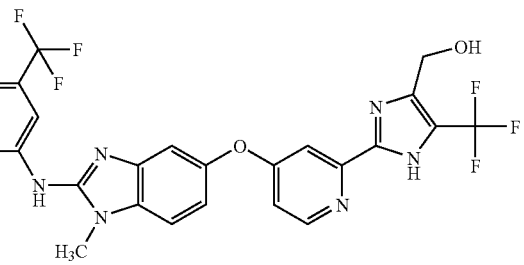

Red-Al (sodium bis(2-methoxyethoxy)aluminium hydride, 65% wt in toluene, 0.1 mL) was added dropwise to a solution of 2-{4-[2-(2-fluoro-5-trifluoromethyl-phenylamino)-1-methyl-1H-benzoimidazol-5-yloxy]-pyridin-2-yl}-5-trifluoromethyl-1H-imidazole-4-carboxylic acid ethyl ester (0.0104 g, 0.017 mmol) in toluene. Effervescence was observed and after 20 min, the reaction was quenched with H₂O, NaOH and extracted with EtOAc. The organic layer was washed with H₂O, dried over Na₂SO₄, filtered and concentrated to give 5.9 mg of crude (2-{4-[2-(2-fluoro-5-trifluoromethyl-phenylamino)-1-methyl-1H-benzoimidazol-5-yloxy]-pyridin-2-yl}-5-trifluoromethyl-1H-imidazol-4-yl)-methanol which was further purified by RP HPLC (reverse phase HPLC) to give 1.1 mg of the pure compound (98% purity). LC/MS m/z 567.1 (MH⁺), R_t 2.40 min.

Example 16

Preparation of 2-{4-[1-Methyl-2-(4-trifluoromethyl-phenylamino)-1H-benzoimidazol-5-yl-oxy]-pyridin-2-yl}-3H-imidazole-4-carbonitrile

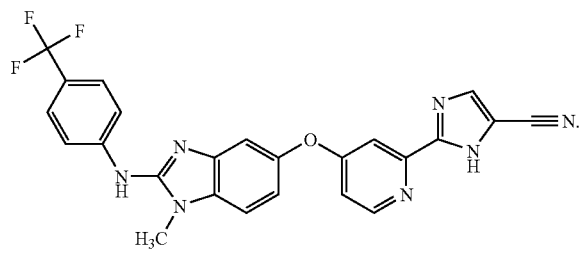

A slurry of {1-methyl-5-[2-(5-trifluoromethyl-1H-imidazol-2-yl)-pyridin-4-yloxy]-1H-benzoimidazol-2-yl}-(4-trifluoromethyl-phenyl)-amine was prepared according to Example 1 (1.83 g, 3.4 mmol) and 28% NH$_4$OH (23 mL) in MeOH (10 mL) was sealed in a tube and heated to 140° C. for 3 h. After the reaction was judged complete by LC/MS, the crude reaction mixture was added to a separatory funnel and partitioned with EtOAc (50) and water (50 mL). The layers were separated, and the aqueous phase was extracted with EtOAc (2×50 mL). The organic layers were combined, washed with brine, then dried (MgSO$_4$), and concentrated. The crude product was adsorbed onto SiO$_2$ and purified by flash chromatography to give 2-{4-[1-methyl-2-(4-trifluoromethyl-phenylamino)-1H-benzoimidazol-5-yloxy]-pyridin-2-yl}-3H-imidazole-4-carbonitrile as a white solid. LC/MS m/z 476.1 (MH$^+$).

Examples 17-59a

The compounds shown in the following Table 1 (Examples 17-59a) were prepared from following the procedures described for Examples 1-16. Various starting materials used in the synthesis of the compounds will be apparent to one of skill in the art (e.g. Tordeux, M.; Langlois, B.; Wakselman, C. *J. Chem. Soc. Perkin Trans* 1 1990, 2293).

TABLE 1

| Example | Structure | Name | MH+ |
|---|---|---|---|
| 17 | 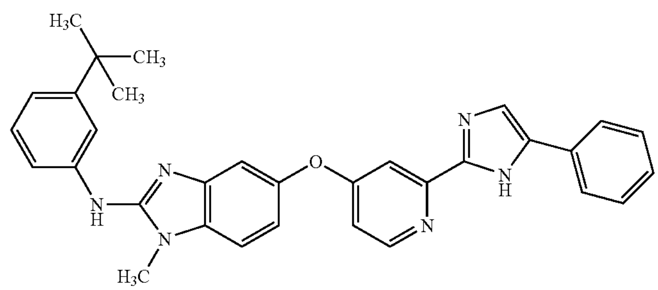 | (3-tert-Butyl-phenyl)-{1-methyl-5-[2-(5-phenyl-1H-imidazol-2-yl)-pyridin-4-yloxy]-1H-benzo-imidazol-2-yl}-amine | 515.4 |
| 18 | 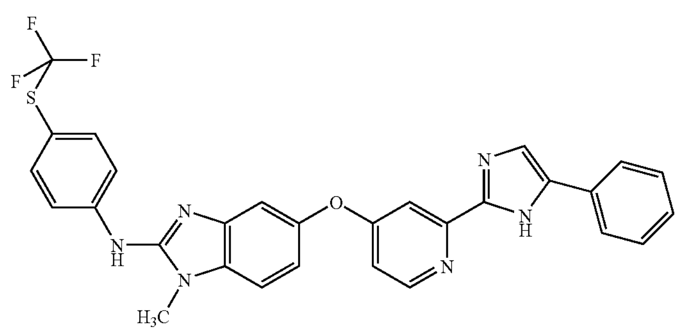 | {1-Methyl-5-[2-(5-phenyl-1H-imidazol-2-yl)-pyridin-4-yloxy]-1H-benzoimidazol-2-yl}-(4-trifluoromethylsulfany-phenyl)-amine | 559.3 |
| 19 | 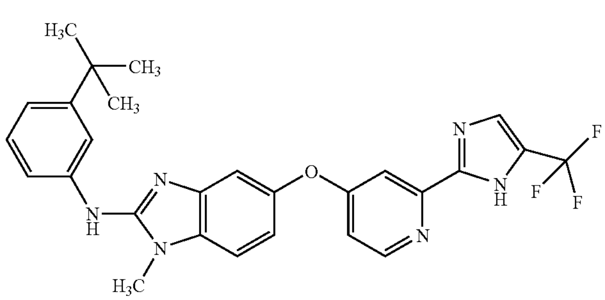 | (3-tert-Butyl-phenyl)-{1-methyl-5-[2-(5-trifluoromethyl-1H-imidazol-2-yl)-pyridin-4-yloxy]-1H-benzoimidazol-2-yl}-amine | 507.1 |

TABLE 1-continued

| Example | Structure | Name | MH+ |
|---|---|---|---|
| 20 | 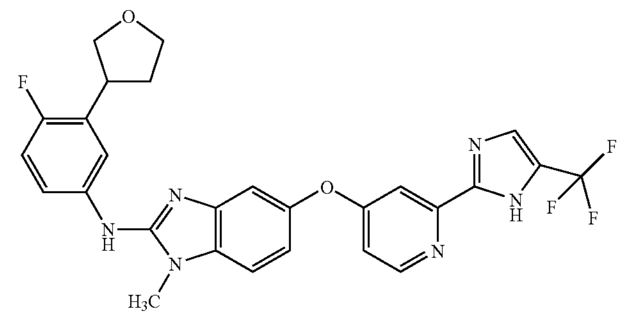 | (4-Fluoro-3-(tetrahydro-furan-3-yl)-phenyl]-{1-methyl-5-[2-(5-trifluoromethyl-1H-imidazol-2-yl)-pyridin-4-yloxy)-1H-benzoimidazol-2-yl}-amine | 539.3 |
| 21 | 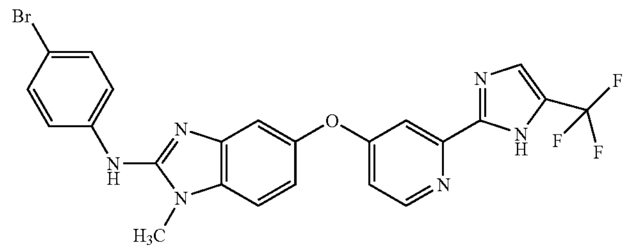 | (4-Bromo-phenyl)-{1-methyl-5-[2-(5-trifluoromethyl-1H-imidazol-2-yl)-pyridin-4-yloxy]-1H-benzoimidazol-2-yl}-amine | 529.1 |
| 22 | 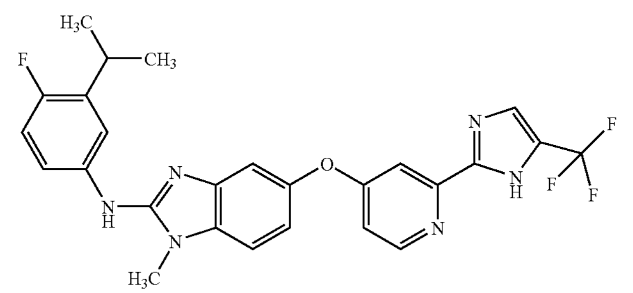 | (4-Fluoro-3-isopropyl-phenyl)-{1-methyl-5-[2-(5-trifluoromethyl-1H-imidazol-2-yl)-pyridin-4-yloxy]-1H-benzoimidazol-2-yl}-amine | 511.3 |
| 23 | 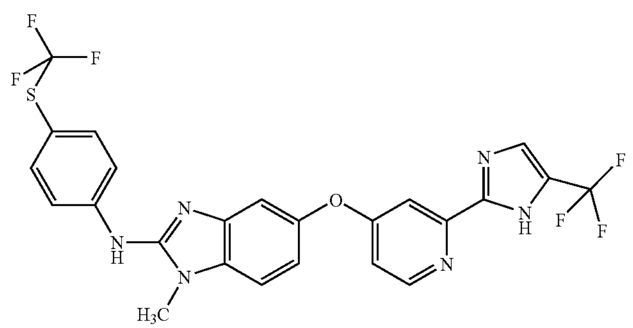 | {1-Methyl-5-[2-(5-trifluoromethyl-1H-imidazol-2-yl)-pyridin-4-yloxy]-1H-benzoimidazol-2-yl}-(4-trifluoromethylsulfanyl-phenyl)-amine | 551.2 |
| 24 | 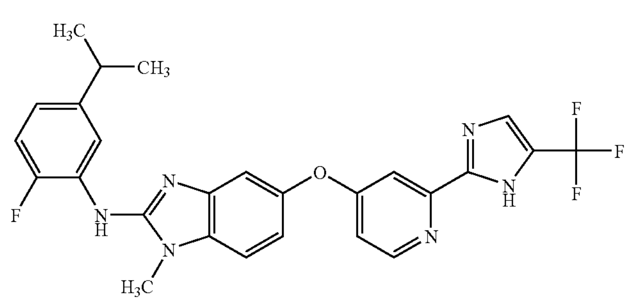 | (2-Fluoro-5-isopropyl-phenyl)-{1-methyl-5-[2-(5-trifluoromethyl-1H-imidazol-2-yl)-pyridin-4-yloxy]-1H-benzoimidazol-2-yl}-amine | 511.1 |

TABLE 1-continued

| Example | Structure | Name | MH+ |
|---|---|---|---|
| 25 | 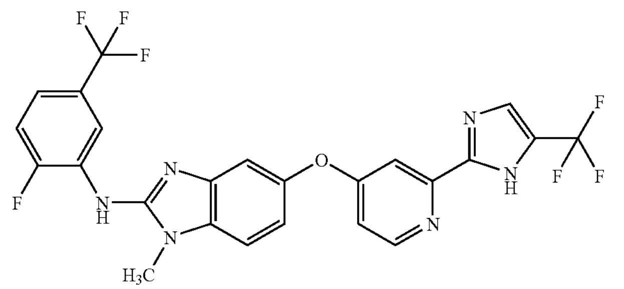 | (2-Fluoro-5-trifluoromethyl-phenyl)-{1-methyl-5-[2-(5-trifluoromethyl-1H-imidazol-2-yl)-pyridin-4-yloxy]-1H-benzoimidazol-2-yl}-amine | 537.0 |
| 26 | 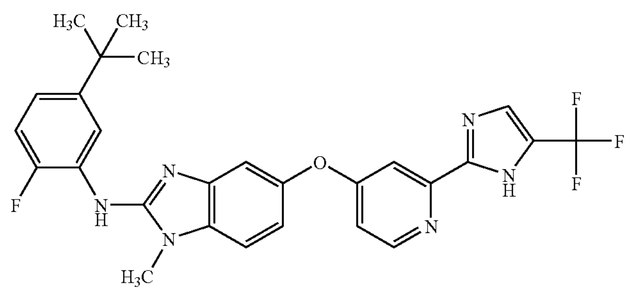 | (5-tert-Butyl-2-fluoro-phenyl)-{1-methyl-5-[2-(5-trifluoromethyl-1H-imidazol-2-yl)-pyridin-4-yloxy]-1H-benzoimidazol-2-yl}-amine | 525.1 |
| 27 | 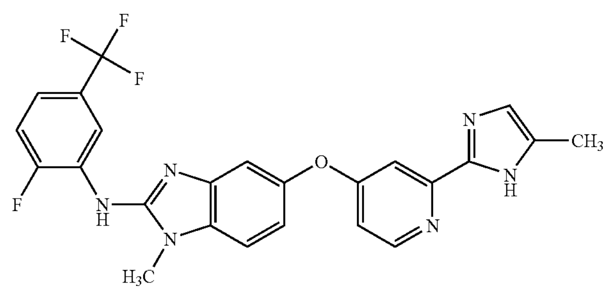 | (2-Fluoro-5-trifluoromethyl-phenyl)-(1-methyl-5-[2-(5-methyl-1H-imidazol-2-yl)-pyridin-4-yl-oxy]-1H-benzoimidazol-2-yl}-amine | 483.1 |
| 28 | 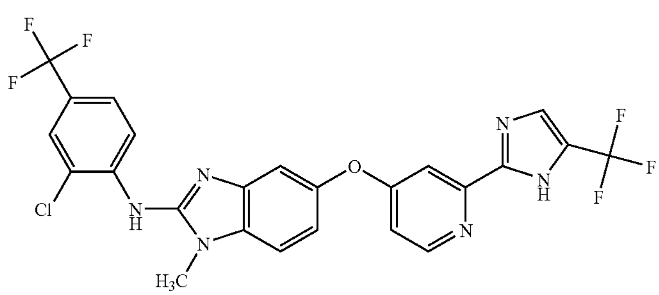 | (2-Chloro-4-trifluoromethyl-phenyl)-{1-methyl-5-[2-(5-trifluoromethyl-1H-imidazol-2-yl)-pyridin-4-yloxy]-1H-benzoimidazol-2-yl}-amine | 553.0 |
| 29 | 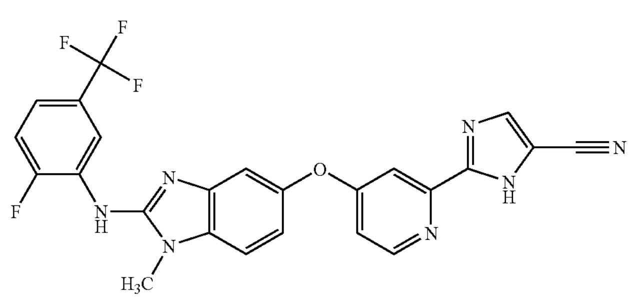 | 2-{4-(2-(2-Fluoro-5-trifluoromethyl-phenylamino)-1-methyl-1H-benzoimidazol-5-yloxy]-pyridin-2-yl}-3H-imidazole-4-carbonitrile | 494.1 |

TABLE 1-continued

| Example | Structure | Name | MH+ |
|---|---|---|---|
| 30 | 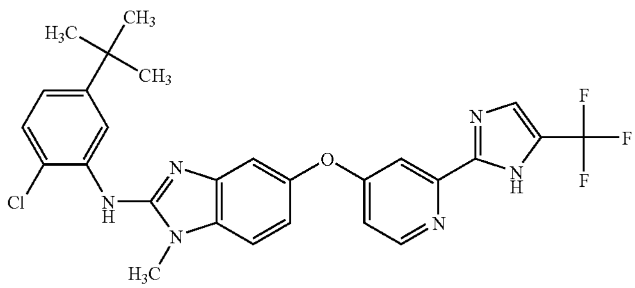 | (5-tert-Butyl-2-chloro-phenyl)-{1-methyl-5-[2-(5-trifluoromethyl-1H-imidazol-2-yl)-pyridin-4-yloxy]-1H-1-benzoimidazol-2-yl}-amine | 541.1 |
| 31 | 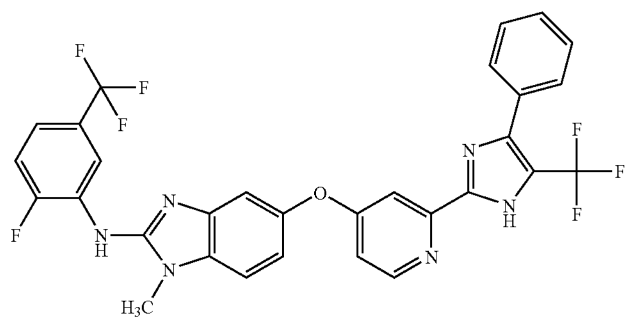 | (2-Fluoro-5-trifluoromethyl-phenyl)-{1-methyl-5-[2-(4-phenyl-5-trifluoromethyl-1H-imidazol-2-yl)-pyridin-4-yloxy]-1H-benzoimidazol-2-yl}-amine | 613.1 |
| 32 | 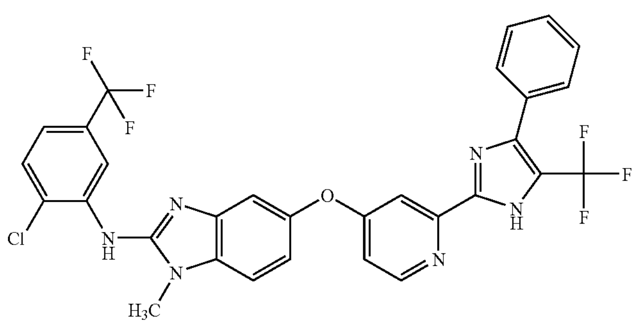 | (2-Chloro-5-trifluoromethyl-phenyl)-{1-methyl-5-[2-(4-phenyl-5-trifluoromethyl-1H-imidazol-2-yl)-pyridin-4-yloxy]-1H-benzoimidazol-2-yl}-amine | 629.0 |
| 33 | 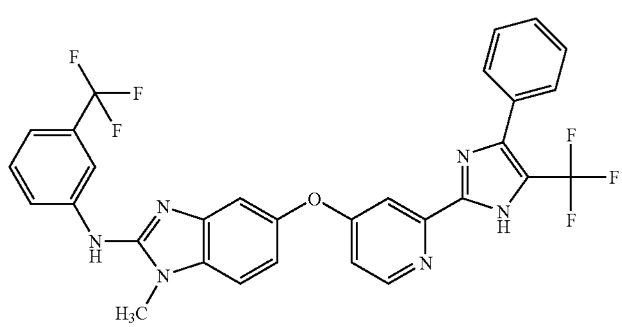 | {1-Methyl-5-[2-(4-phenyl-5-trifluoromethyl-1H-imidazol-2-yl)-pyridin-4-yloxy]-1H-benzoimidazol-2-yl}-(3-trifluoromethyl-phenyl)-amine | 595.1 |

TABLE 1-continued

| Example | Structure | Name | MH+ |
|---|---|---|---|
| 34 | 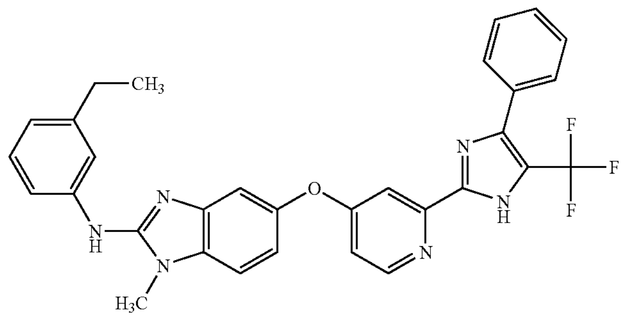 | (3-Ethyl-phenyl)-{1-methyl-5-[2-(4-phenyl-5-trifluoromethyl-1H-imidazol-2-yl)-pyridin-4-yloxy]-1H-benzoimidazol-2-yl}-amine | 555.1 |
| 35 | 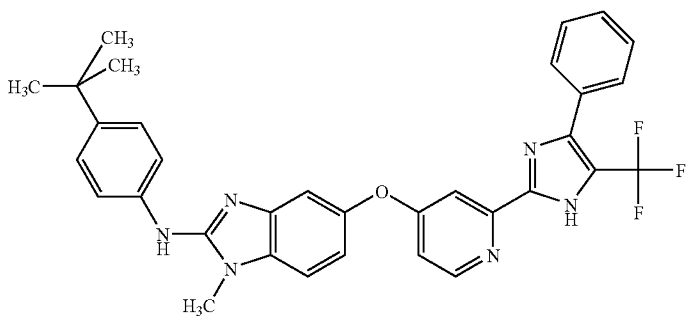 | (4-tert-Butyl-phenyl)-{1-methyl-5-[2-(4-phenyl-5-trifluoromethyl-1H-imidazol-2-yl)-pyridin-4-yloxy]-1H-benzoimidazol-2-yl}-amine | 583.2 |
| 36 | 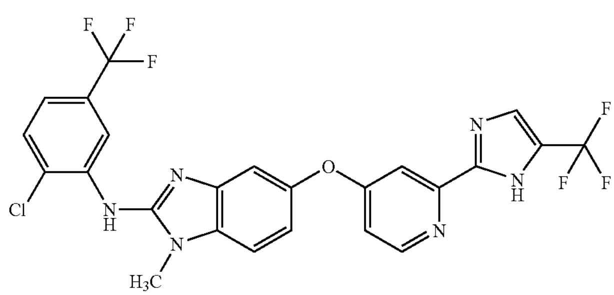 | (2-Chloro-5-trifluoromethyl-phenyl)-{1-methyl-5-[2-(5-trifluoromethyl-1H-imidazol-2-yl)-pyridin-4-yloxy]-1H-benzoimidazol-2-yl}-amine | 553.1 |
| 37 | 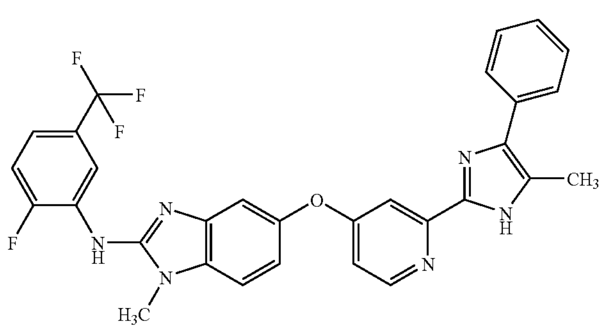 | (2-Fluoro-5-trifluoromethyl-phenyl)-{1-methyl-5-[2-(5-methyl-4-phenyl-1H-imidazol-2-yl)-pyridin-4-yloxy]-1H-benzoimidazol-2-yl}-amine | 559.1 |

TABLE 1-continued

| Example | Structure | Name | MH+ |
|---|---|---|---|
| 38 | 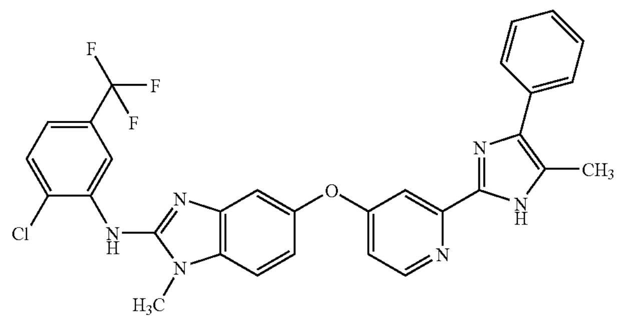 | (2-Chloro-5-trifluoromethyl-phenyl)-{1-methyl-5-[2-(5-methyl-4-phenyl-1H-imidazol-2-yl)-pyridin-4-yloxy]-1H-benzo-imidazol-2-yl}-amine | 575.1 |
| 39 | 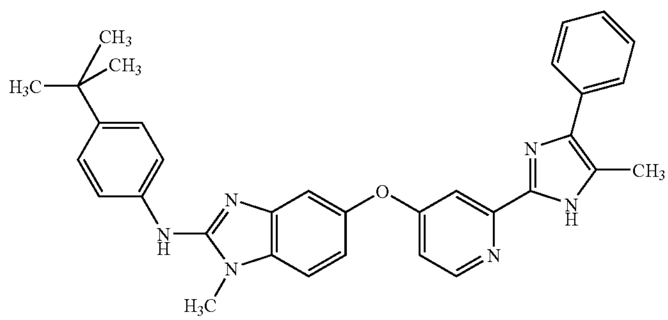 | (4-tert-Butyl-phenyl)-{1-methyl-5-[2-(5-methyl-4-phenyl-1H-imidazol-2-yl)-pyridin-4-yloxy]-1H-benzoimidazol-2-yl}-amine | 529.3 |
| 40 | 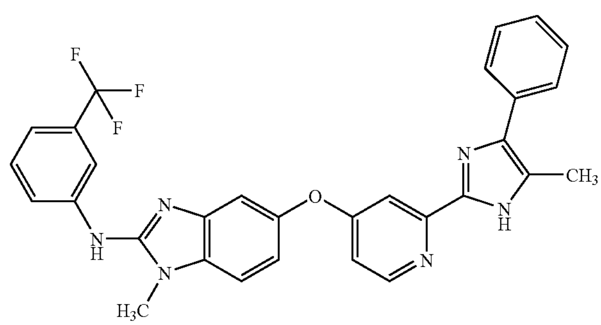 | {1-Methyl-5-[2-(5-methyl-4-phenyl-1H-imidazol-2-yl)-pyridin-4-yloxy]-1H-benzoimidazol-2-yl}-(3-trifluoromethyl-phenyl)-amine | 541.2 |
| 41 | 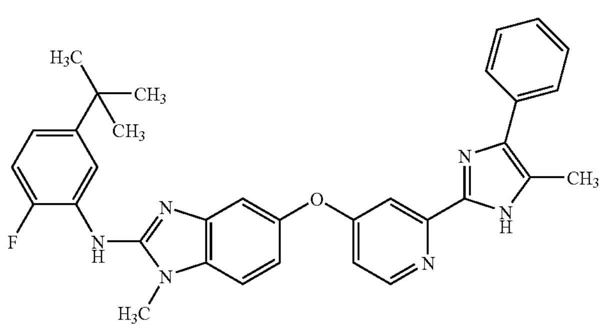 | (5-tert-Butyl-2-fluoro-phenyl)-{1-methyl-5-[2-(5-methyl-4-phenyl-1H-imidazol-2-yl)-pyridin-4-yloxy]-1H-benzoimidazol-2-yl}-amine | 547.2 |

TABLE 1-continued

| Example | Structure | Name | MH+ |
|---|---|---|---|
| 42 | 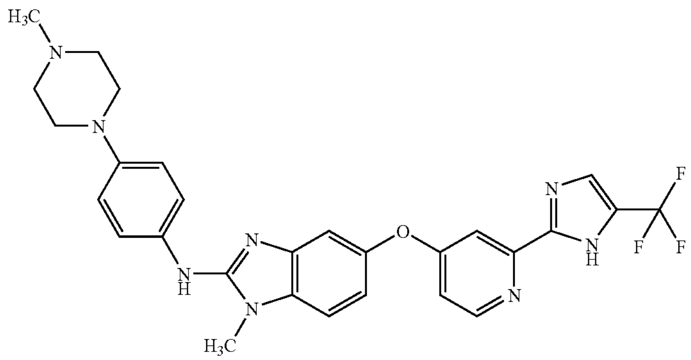 | [4-(4-Methyl-piperazin-1-yl)-phenyl]-{1-methyl-5-[2-(5-trifluoromethyl-1H-imidazol-2-yl)-pyridin-4-yloxy]-1H-benzoimidazol-2-yl}-amine | 549.2 |
| 43 | 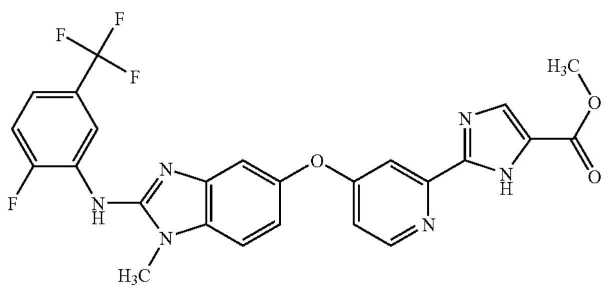 | 2-{4-[2-(2-Fluoro-5-trifluoromethyl-phenylamino)-1-methyl-1H-benzoimidazol-5-yloxy]-pyridin-2-yl}-3H-imidazole-4-carboxylic acid methyl ester | 527.1 |
| 44 | 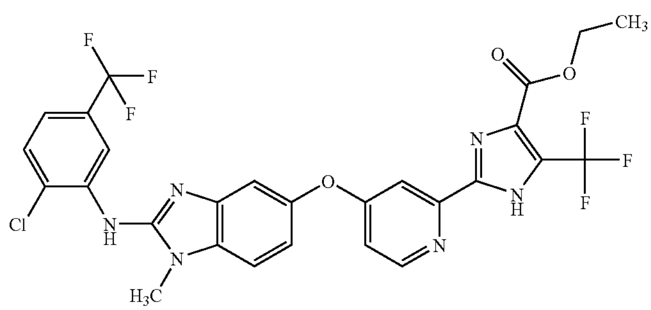 | 2-{4-[2-(2-Chloro-5-trifluoromethyl-phenylamino)-1-methyl-1H-benzoimidazol-5-yloxy]-pyridin-2-yl}-5-trifluoromethyl-1H-imidazole-4-carboxylic acid ethyl ester | 625.0 |
| 45 | 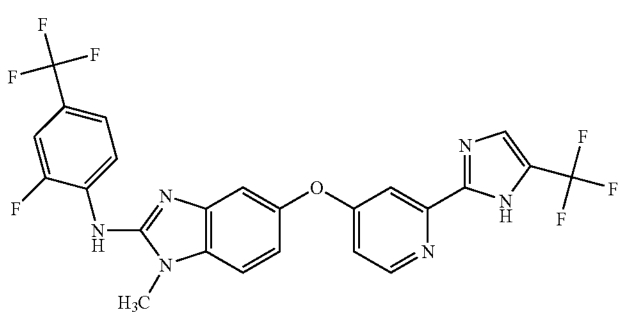 | (2-Fluoro-4-trifluoromethyl-phenyl)-{1-methyl-5-[2-(5-trifluoromethyl-1H-imidazol-2-yl)-pyridin-4-yloxy]-1H-benzoimidazol-2-yl}-amine | 537.1 |
| 46 | 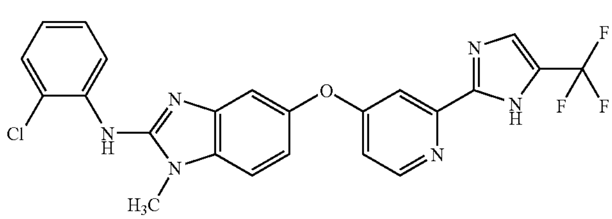 | (2-Chloro-phenyl)-{1-methyl-5-[2-(5-trifluoromethyl-1H-imidazol-2-yl)-pyridin-4-yloxy]-1H-benzoimidazol-2-yl}-amine | 485.1 |

TABLE 1-continued

| Example | Structure | Name | MH+ |
|---|---|---|---|
| 47 | 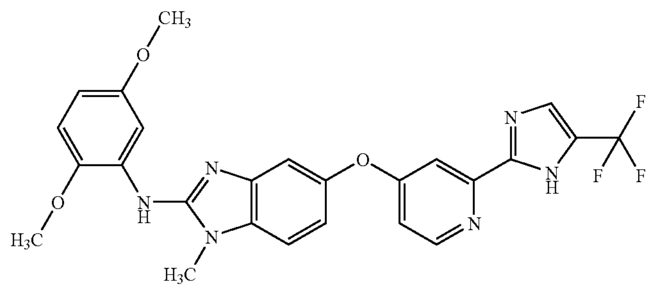 | (2,5-Dimethoxy-phenyl)-{1-methyl-5-[2-(5-trifluoromethyl-1H-imidazol-2-yl)-pyridin-4-yloxy]-1H-benzoimidazol-2-yl}-amine | 511.1 |
| 48 | 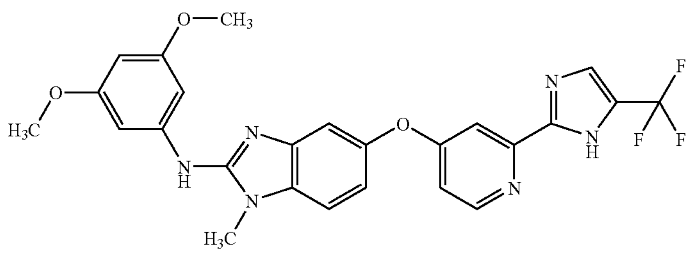 | (3,5-Dimethoxy-phenyl)-{1-methyl-5-[2-(5-trifluoromethyl-1H-imidazol-2-yl)-pyridin-4-yloxy]-1H-benzoimidazol-2-yl}-amine | 511.2 |
| 49 | 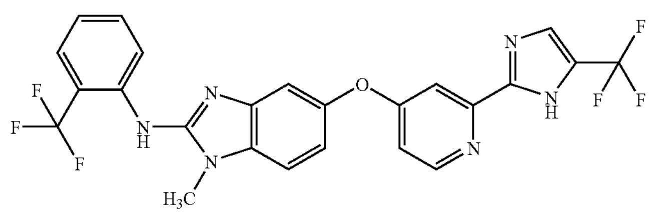 | (1-Methyl-5-[2-(5-trifluoromethyl-1H-imidazol-2-yl)-pyridin-4-yloxy]-1H-benzoimidazol-2-yl}-(2-trifluoromethyl-phenyl)-amine | 519.1 |
| 50 | 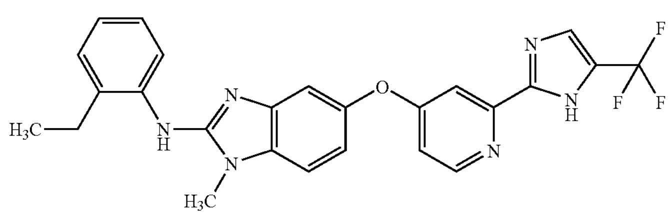 | (2-Ethyl-phenyl)-{1-methyl-5-[2-(5-trifluoromethyl-1H-imidazol-2-yl)-pyridin-4-yloxy]-1H-benzoimidazol-2-yl}-amine | 479.2 |
| 51 | 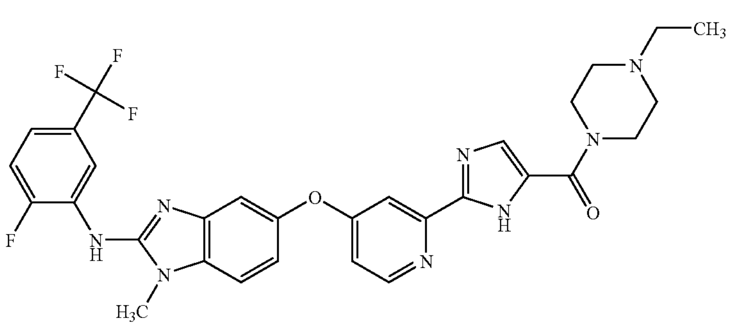 | (4-Ethyl-piperazin-1-yl)-(2-{4-[2-(2-fluoro-5-trifluoromethyl-phenylamino)-1-methyl-1H-benzoimidazol-5-yloxy]-pyridin-2-yl}-3H-imidazol-4-yl)-methanone | 609.2 |

TABLE 1-continued

| Example | Structure | Name | MH+ |
|---|---|---|---|
| 52 | 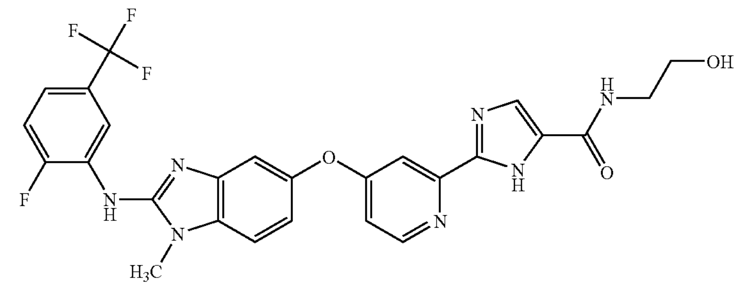 | 2-{4-[2-(2-Fluoro-5-trifluoromethyl-phenylamino)-1-methyl-1H-benzoimidazol-5-yloxy]-pyridin-2-yl}-3H-imidazole-4-carboxylic acid (2-hydroxy-ethyl)-amide | 556.1 |
| 53 | 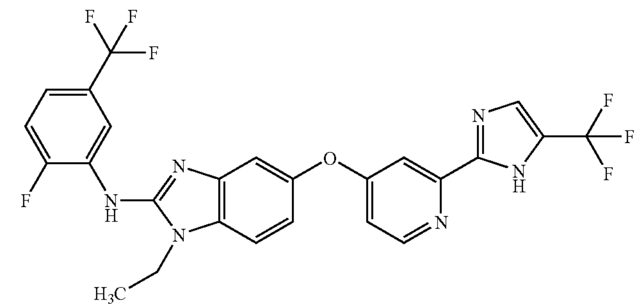 | {1-Ethyl-5-[2-(5-trifluoromethyl-1H-imidazol-2-yl)-pyridin-4-yloxy]-1H-benzoimidazol-2-yl}-(2-fluoro-5-trifluoromethyl-phenyl)-amine | 551.1 |
| 54 | 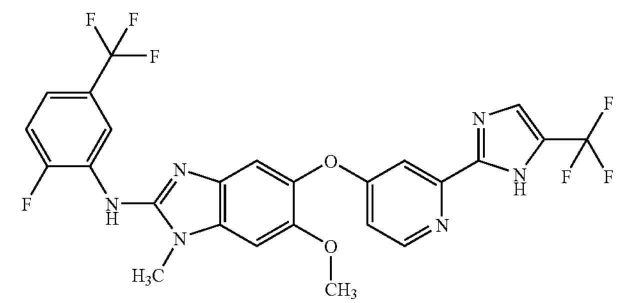 | (2-Fluoro-5-trifluoromethyl-phenyl)-{6-methoxy-1-methyl-5-[2-(5-trifluoromethyl-1H-imidazol-2-yl)-pyridin-4-yloxy]-1H-benzoimidazol-2-yl}-amine | 567.4 |
| 55 | 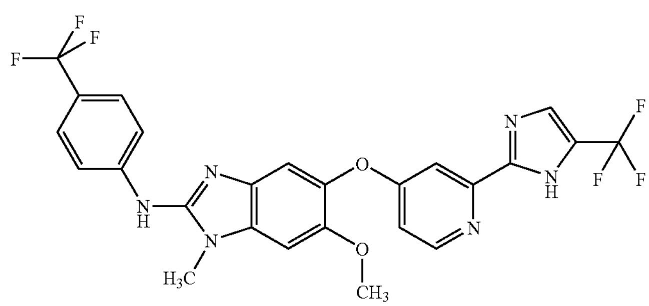 | {6-Methoxy-1-methyl-5-[2-(5-trifluoromethyl-1H-imidazol-2-yl)-pyridin-4-yloxy]-1H-benzoimidazol-2-yl}-(4-trifluoromethyl-phenyl)-amine | 549.4 |
| 56 | 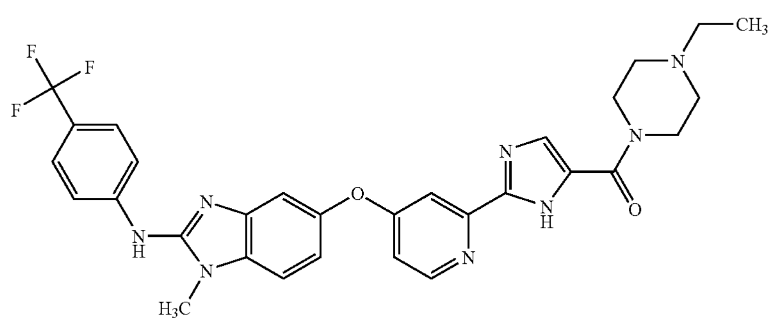 | (4-Ethyl-piperazin-1-yl)-(2-{4-[1-methyl-2-(4-trifluoromethyl-phenylamino)-1H-benzoimidazol-5-yloxy]-pyridin-2-yl}-3H-imidazol-4-yl)-methanone | 591.2 |

TABLE 1-continued

| Example | Structure | Name | MH+ |
|---|---|---|---|
| 57 | 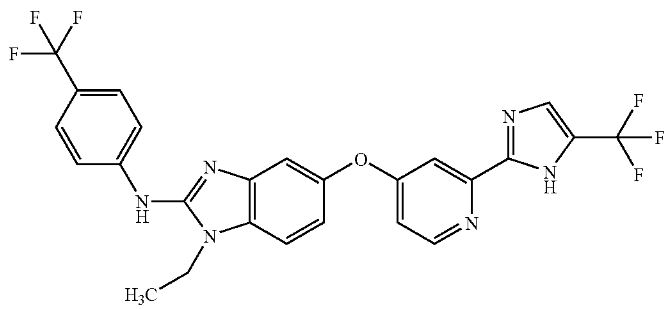 | {1-Ethyl-5-[2-(5-trifluoromethyl-1H-imidazol-2-yl)-pyridin-4-yl-oxy]-1H-benzoimidazol-2-yl}-(4-trifluoromethyl-phenyl)-amine | 533.1 |
| 58 | 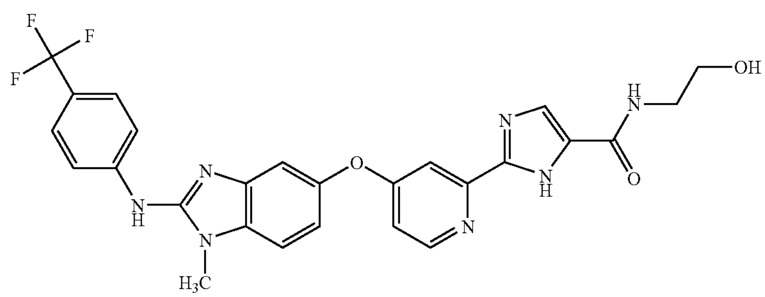 | 2-{4-[1-Methyl-2-(4-trifluoromethyl-phenylamino)-1H-benzoimidazol-5-yloxy]-pyridin-2-yl}-3H-imidazole-4-carboxylic acid (2-hydroxy-ethyl)-amide | 538.1 |
| 59 | 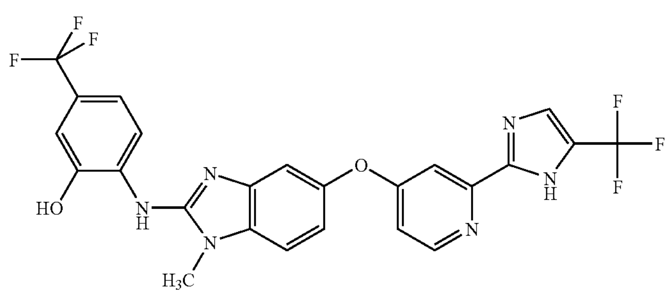 | 2-{1-Methyl-5-[2-(5-trifluoromethyl-1H-imidazol-2-yl)-pyridin-4-yloxy]-1H-benzoimidazol-2-ylamino}-5-trifluoromethyl-phenol | 535.3 |
| 59a | 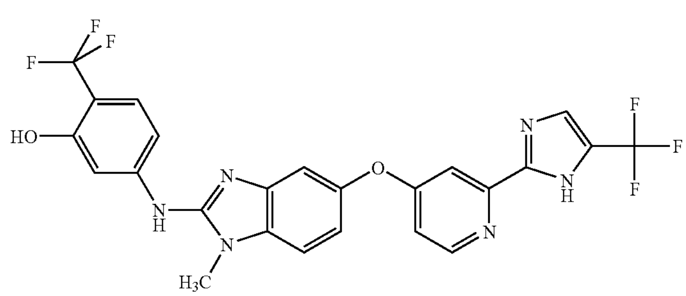 | 3-{1-Methyl-5-[2-(5-trifluoromethyl-1H-imidazol-2-yl)-pyridin-4-yloxy]-1H-benzoimidazol-2-ylamino}-6-trifluoromethyl-phenol | 535.3 |

Example 60

Preparation of (2-Fluoro-5-trifluoromethyl-phenyl)-{1-methyl-5-[2-(5-pyridin-2-yl-2H-[1,2,4]triazol-3-yl)-pyridin-4-yloxy]-1H-benzoimidazol-2-yl}-amine

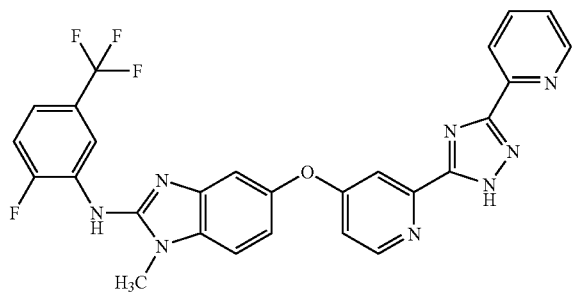

Preparation of 4-[2-(2-fluoro-5-trifluoro-phenylamino)-1-methyl-1H-benzoimidazol-5-yloxy]-pyridine-2-carbonitrile

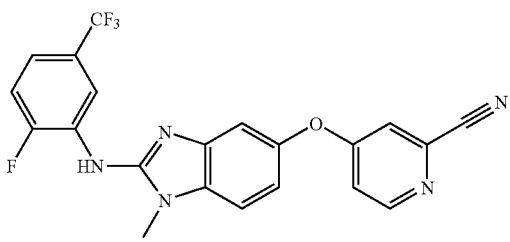

Step 1. Synthesis of 4-(4-Amino-3-nitro-phenoxy)pyridine-2-carbonitrile:

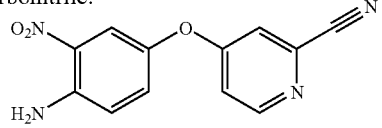

Potassium carbonate (9 g) was dried in vacuo with heating, cooled to room temperature under nitrogen. 4-Amino-3-nitrophenol (3.4 g), 4-chloro-2-cyanopyridine (3.0 g) and dimethylsulfoxide (30 mL, anhydrous) were added. The system was stirred under nitrogen as it was heated to 103° C., and held at this temperature for 1 hr. The reaction was then cooled to RT, poured onto ice/H₂O (500 mL) the precipitate was collected, washed (H₂O), dissolved (EtOAc), dried (Na₂SO₄), filtered and stripped to a solid. This was suspended (Et₂O), collected, air-dried 4.1 g (73.5%) and a second crop was collected (0.55 gm, 10%). m/z=257 (M+1).

Step 2. Synthesis of N-[4-(2-Cyano-pyridin-4-yloxy)-2-nitro-phenyl]-2,2,2-trifluoro-N-methyl-acetamide:

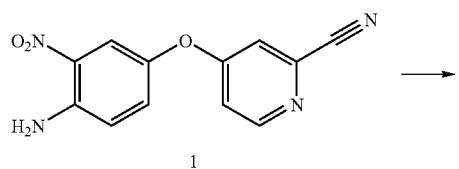

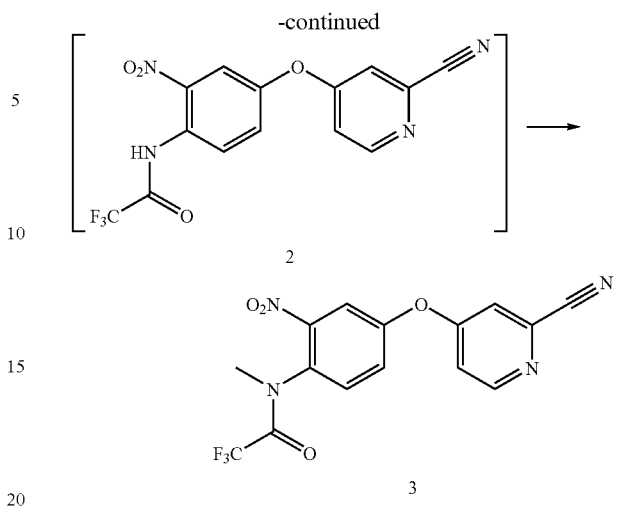

Potassium carbonate (1.6 g) was dried in vacuo with heating, cooled to room temperature and suspended in dichloromethane (30 mL) with 4-(4-amino-3-nitro-phenoxy)pyridine-2-carbonitrile (2.0 g) under nitrogen. This was cooled to 0° C. and trifluoroacetic anhydride (2.2 mL) was added, neat. The starting material goes into solution rapidly as addition is made. After 10 min at 0° C., the mixture was diluted with dichloromethane, washed (H₂O, aq. NaCl), dried (K₂CO₃), filtered and stripped to a yellow foam. m/z=353 (M+1). This product was used without purification. Iodomethane (0.53 mL) was added to a suspension of potassium carbonate (1.858 g) in dimethylformamide DMF (30 mL containing compound 2, ~7.8 mmol) under nitrogen. The suspension stirred at room temperature overnight, then poured onto H₂O (300 mL), extracted (Et₂O, 3×150 mL), the combined extracts were washed (H₂O, aq. NaCl), dried (potassium carbonate), filtered and stripped to yield an orange oil (7.4922 g). m/z=367 (M+1).

Step 3. Synthesis of 4-(4-Methylamino-3-nitro-phenoxy)-pyridine-2-carbonitrile:

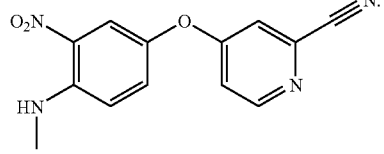

NaOH (1 mL, 1N aq.) was added dropwise to a solution of N-[4-(2-cyano-pyridin-4-yloxy)-2-nitro-phenyl]-2,2,2-trifluoro-N-methyl-acetamide (3, 440 mg) in ethanol (6 mL) at room temperature. After 40 min, the mixture was diluted with H₂O (20 mL) and cooled to 0° C. Bright orange crystals were collected, washed (H2O) and air-dried 311.1 mg (94%). m/z=271 (M+1)

Step 4. Synthesis of 4-[2-(2-fluoro-5-trifluoro-phenylamino)-1-methyl-1H-benzoimidazol-5-yloxy]-pyridine-2-carbonitrile:

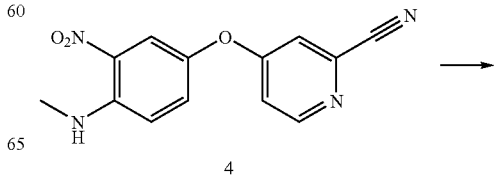

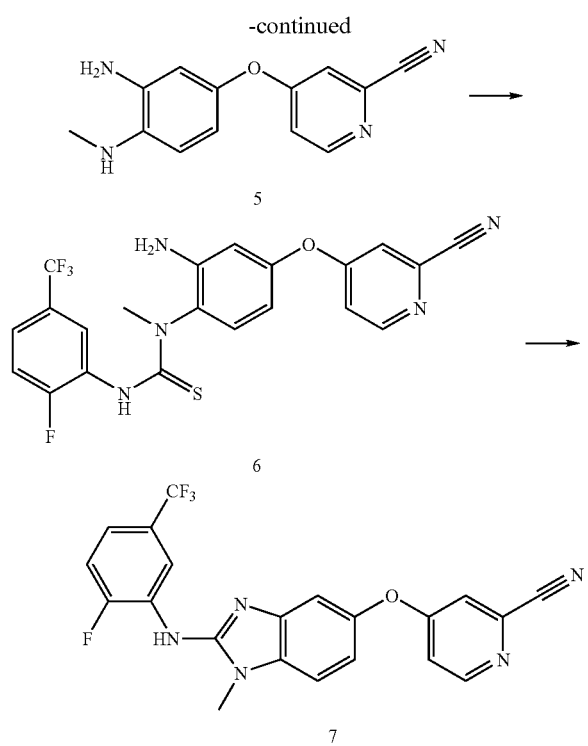

Palladium on carbon (46 mg, 10% w/w) was suspended in MeOH (2 mL) under nitrogen. The resulting suspension was added, under nitrogen, to a suspension of 4-(4-methylamino-3-nitro-phenoxy)-pyridine-2-carbonitrile (311 mg) in MeOH (3 mL) at room temperature. The atmosphere was exchanged with hydrogen, and the system stirred vigorously under 1 atm hydrogen for 1 hr. The atmosphere was then exchanged for nitrogen, the mixture was filtered (celite) and the filtrate was used without further purification in the next reaction. m/z=242 (M+1). 2-fluoro-5-trifluoromethylphenylisothiocyanate (250 mg) was added to a solution of compound 5 in MeOH (10 mL). The solution was stirred at reflux for 2 hrs. After the reaction was judged complete, anhydrous $FeCl_3$ (1.3 eq., 244 mg) was added to the reaction and the resulting mixture was stirred at room temperature overnight. The crude reaction mixture was added to a separatory funnel containing EtOAc and water. The layers were separated, and the aqueous phase was extracted with EtOAc. The organic layers were combined, washed with saturated aqueous $Na_2CO_3$ solution, water, and brine, then dried ($MgSO_4$), and concentrated. This material was chromatographed (gradient 0-5% MeOH in dichloromethane on silica gel) to isolate the desired compound in 28% yield from compound 4. m/z=428 (M+1).

Step 5. (2-Fluoro-5-trifluoromethyl-phenyl)-{1-methyl-5-[2-(5-pyridin-2-yl-2H-[1,2,4]triazol-3-yl)-pyridin-4-yloxy]-1H-benzoimidazol-2-yl}-amine

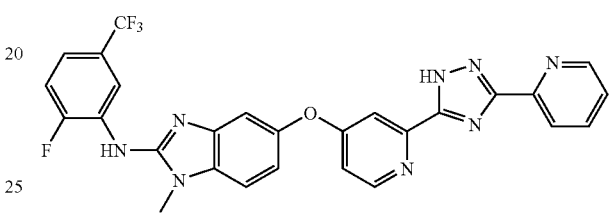

Step 6

4-[2-(4-Fluoro-phenylamino)-1-methyl-1H-benzoimidazol-5-yloxy]-pyridine-2-carbonitrile was solubilized in EtOH (0.1M) and NaOEt was added (1 eq., 0.5 M in EtOH) followed by picolinyl hydrazide (1 eq.) and the solution is heated in a microwave for 2000 seconds at 140° C. The reaction mixture is then concentrated and purified by reverse phase HPLC to yield the desired product. m/z=547 (M+1).

Examples 61-64

The compounds shown in the following Table 2 (Examples 61-64) were prepared by following the procedure described for Example 60.

TABLE 2

| Example | Structure | Name | MH+ |
|---|---|---|---|
| 61 | 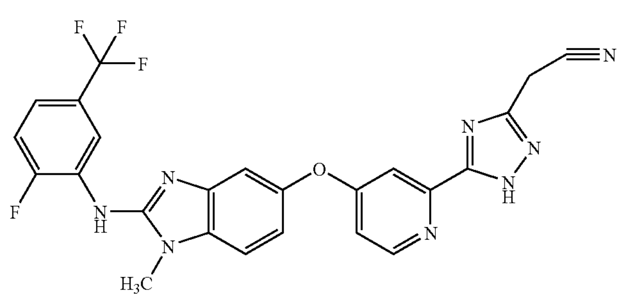 | (5-{4-[2-(2-Fluoro-5-trifluoro-methyl-phenylamino)-1-methyl-1H-benzoimidazol-5-yloxy]-pyridin-2-yl}-1H-[1,2,4]triazol-3-yl)-acetonitrile | 509.2 |

TABLE 2-continued

| Example | Structure | Name | MH+ |
|---|---|---|---|
| 62 | 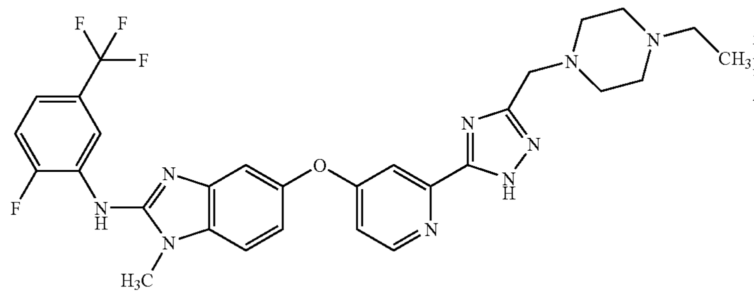 | (5-{2-[5-(4-Ethyl-piperazin-1-yl-methyl)-2H-[1,2,4]triazol-3-yl]-pyridin-4-yloxy}-1-methyl-1H-benzoimidazol-2-yl)-(2-fluoro-5-trifluoromethyl-phenyl)-amine | 596.2 |
| 63 | 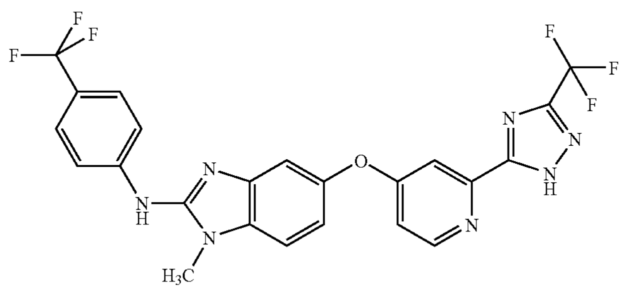 | {1-Methyl-5-[2-(5-trifluoromethyl-2H-[1,2,4]triazol-3-yl)-pyridin-4-yloxy]-1H-benzoimidazol-2-yl}-(4-trifluoromethyl-phenyl)-amine | 520.2 |
| 64 | 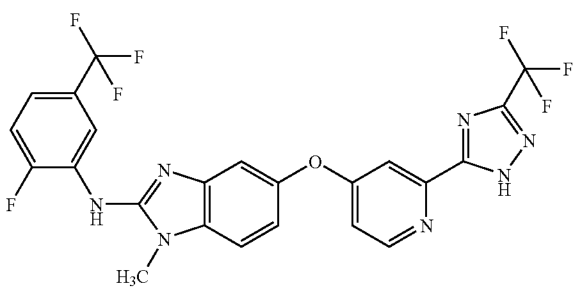 | (2-Fluoro-5-trifluoromethyl-phenyl)-{1-methyl-5-[2-(5-trifluoromethyl-2H-[1,2,4]triazol-3-yl)-pyridin-4-yloxy]-1H-benzoimidazol-2-yl}-amine | 538.2 |

Example 65

Preparation of N-(4-hydroxy-2-nitrophenyl)-formamide

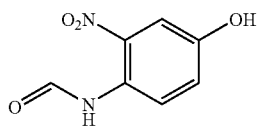

N-(4-hydroxy-2-nitrophenyl)-formamide can be prepared according to the following procedure:

1. Set up a 3-L, 5-necked reaction flask fitted with an internal temperature probe, temperature controller, heating mantle, condenser, mechanical stirrer, 1-L addition funnel and a nitrogen inlet. Flush the reactor with nitrogen for 5 minutes.
2. Charge acetic anhydride (245 mL) to the flask. Stir under nitrogen.
3. Charge formic acid (125 mL) in one portion (an exotherm is observed due to the mixing and the reaction between acetic anhydride and formic acid).
4. Set internal temperature (IT) end point to 60° C. and start heating. After IT reaches 60° C., stir and maintain for another 2 hours.
5. Cool contents with an ice bath.
6. When IT reaches ambient temperature (ca 20° C.), start adding a solution of 4-amino-3-nitrophenol (160 g) in 700 mL of anhydrous THF (tetrahydrofuran) via the 1-L addition funnel in portions so that IT does not exceed. 40° C. The product starts to precipitate out as a yellow solid.
7. When the addition is completed, replace the ice bath with a heating mantle. Set IT end point at 60° C. and start heating.
8. Monitor the reaction progress by HPLC. The reaction normally takes less than 1 hour.
9. When the starting material is <1 area %, add 500 mL of water. Cool to room temperature with an ice bath.
10. Collect the product by vacuum filtration. Wash the filter cake with 3×200 mL of water. Air-dry, and further dry in an oven at 50° C. at 27 in. Hg vacuum with a gentle air or nitrogen bleed until a consistent weight is reached.

Example 66

Preparation of 4-methylamino-3-nitrophenol

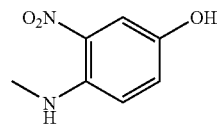

4-Methylamino-3-nitrophenol can be prepared according to the following procedure:
1. Set up a 500 mL, 3-necked reaction flask fitted with an internal temperature probe, and a nitrogen inlet. Flush the reactor with nitrogen for 5 minutes.
2. Charge N-(4-hydroxy-2-nitrophenyl)-formamide (5 g) and anhydrous THF (100 mL) to the reactor. Stir under $N_2$ to afford a yellow slurry.
3. Add the boron trifluoride diethyl etherate (3.83 mL) via syringe slowly.
4. Stir the reaction mixture for 30 minutes at room temperature.
5. Add the sodium borohydride (1.04 g) portion wise via an addition funnel.
6. Stir the reaction for one hour and monitor the reaction by HPLC every hour thereafter (reaction typically takes 3 hours).
7. When the HPLC sample shows the starting material is less then 1.0% slowly add 1 M HCl (40 mL) via a syringe over a period of 10 minutes.
8. Stir for 60 minutes.
9. Add 1 M NaOH as needed via a syringe to bring pH to 7±0.5.
10. Pour the reaction mixture into a 500 mL round bottom flask and concentrate under reduced pressure (20 mm Hg, at 25° C.) until ca 100 mL of clear liquid is removed.
11. Add water (100 mL) to the reaction vessel. Cool to 0±2° C. with stirring. The product precipitates out as a red solid.
12. Collect the product by vacuum filtration through a coarse fritted funnel. Wash the filter cake with water (2×20 mL). Air-day and then dry in an oven at 50° C./27 in. Hg until a consistent weight is reached. Submit samples for analysis.

Example 67

Preparation of 4-chloropyridine-2-carbonyl Chloride

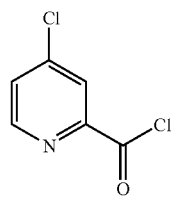

4-Chloropyridine-2-carbonyl chloride can be prepared according to the following procedure:
1. Set up a 5-L, 5-necked reaction flask fitted with an internal temperature (IT) probe, a temperature controller, heating mantle, condenser, mechanical stirrer, nitrogen inlet, gas outlet on top of the condenser that is connected to a 2-L, 2-neck liquid trap that is in turn connected to a 12-L scrubber filled with approx. 6 liters of 8 M NaOH solution and stirred with a magnetic stirrer. Flush the reactor with nitrogen for 5 minutes and then shut off nitrogen flow.
2. Charge thionyl chloride (1.18 L) to the reactor, followed by potassium bromide (38.4 g) while maintaining moderate stirring (ca 200 rpm).
3. Charge picolinic acid (397 g) to the reactor.
4. Set the IT end point at 80° C. and start heating.
5. Take samples and monitor the reaction progress by HPLC. The reaction normally takes around 14 hours to go to completion. Extended heating will result in more di-chlorination.
6. When the reaction is deemed complete (less than 1% of picolinic acid is present in the reaction mixture), stop heating. Remove the heating mantle.
7. When the IT is below 30° C., transfer the liquid to a 3-L reaction flask. Rinse the 5-L reactor with 700 mL of toluene. Transfer the rinses to the 3-L flask. Remove excess $SOCl_2$ and toluene under reduced pressure. Repeat the process with 2×700 mL of toluene. Remove all solvent yielding a yellow-orange solid. Toluene (400 mL) was added to the reaction mixture. Resulting mixture was carried on to the next step.

Example 68

Preparation of 4-chloropyridine-2-carboxylic Acid T-Butyl Ester

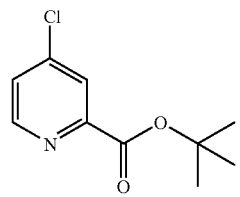

4-Chloropyridine-2-carboxylic acid t-butyl ester can be prepared according to the following procedure:
1. Equip a 12 L round bottom flask (4-necked) with a mechanical stirrer and a thermometer.
2. Charge the reactor with toluene (1 L), pyridine (977.7 g), and di-t-butyl dicarbonate $(BOC)_2O$ (855.5 g).
3. Cool the reactor so that the internal temperature is 0° C.
4. Add the 4-chloropyridine-2-carbonyl chloride (686 g) to the reactor at such a rate as to keep the internal temperature of the reaction below 5° C.
5. The reaction was allowed to slowly come up to room temp (~20° C.) and stirred for 16 hours.
6. When the reaction is deemed complete using HPLC (starting material <0.5 area %) the reaction was washed with water (2×4 L), then 1 M HCl solution (2×2 L).
7. The reaction mixture was concentrated under reduced pressure to remove toluene and residual pyridine.
8. Toluene (500 mL) was added, and then the reaction mixture was concentrated under reduced pressure to obtain the desired product.

Example 69

Preparation of 4-(4-methylamino-3-nitrophenoxy)-pyridine-2-carboxylic Acid T-Butyl Ester

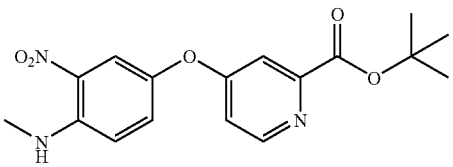

4-(4-Methylamino-3-nitrophenoxy)-pyridine-2-carboxylic acid t-butyl ester can be prepared according to the following procedure:
1. Equip a 3 L round bottom flask with a mechanical stirrer, thermometer and nitrogen inlet.
2. Charge the reactor with the $K_2CO_3$ (123 g).
3. Bring the reaction vessel under inert atmosphere.
4. Charge the reactor with 4-methylamino-3-nitrophenol (100 g), 4-chloropyridine-2-carboxylic acid t-butyl ester (127 g), and dry DMSO (1 L).
5. Stir the reaction vigorously and heat to 110° C.
6. When the reaction is deemed complete using HPLC (<0.5 area % 4-chloropyridine-2-carboxylic acid t-butyl ester), pour the hot reaction mixture into 3 L of stirring cool water (by volume).
7. Isolate the desired compound by filtration, as an orange to orange-brown solid.
8. Rinse the isolated solid with water (2×200 mL) followed by heptane (2×200 mL).
9. Dry material in vacuum oven @ 45-50° C. until constant weight is achieved.

Example 70

Preparation of 4-(4-(methylamino)-3-nitrophenoxy)pyridine-2-carbaldehyde

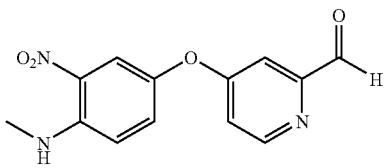

4-(4-(methylamino)-3-nitrophenoxy)pyridine-2-carbaldehyde can be prepared according to the following procedure:
1. Equip a 1000 mL round bottom flask with a nitrogen inlet, mechanical stirrer, and thermometer.
2. Charge the reactor with 4-(4-methylamino-3-nitrophenoxy)-pyridine-2-carboxylic acid t-butyl ester (10 g) via a powder funnel.
3. Add 2-methyl THF (100 mL) via a powder funnel.
4. Cool the reactor until an internal temperature of −25° C.
5. Add the DIBAL (diisobutylaluminum hydride, 1.5 M in toluene; 72 mL) via an addition funnel at such a rate as to keep the internal temperature under −15° C.
6. Analyze the reaction via HPLC or GC (gas chromatography), checking for the disappearance of ester.
7. Stir the reaction at −20° C., monitoring every hour.
8. If the reaction fails to progress after 2 hours, add another 0.5 equivalents of DIBAL (diisobutylaluminum hydride) and monitor the reaction. Keep repeating this step until all the ester has been consumed.
9. Once the reaction is complete quench slowly with MeOH (10 mL).
10. Add the potassium sodium tartrate (40 g) to 200 mL of water and stir to dissolve.
11. Add the aqueous solution to the reaction mixture and allow to warm to RT.
12. Add 2-methyl THF (100 mL) to the reaction vessel.
13. Heat the reaction to 50° C. for 1 hour with stirring.
14. Allow the phases to separate.
15. Remove the lower aqueous layer.
16. Filter the organic layer through a plug of celite.
17. Rinse the celite with 2-methyl THF (2×50 mL).
18. Add the reaction mixture to a 500 mL round bottom flask.
19. Concentrate the reaction mixture to ~50 mL by distillation.
20. Cool the reaction mixture to 0° C. with stirring.
21. Stir the reaction mixture for 1 hour at 0° C.
22. Filter the reaction mixture through a course fritted filter.
23. Allow the solids to dry on the filter for 30 minutes to 1 hour.
24. Analyze the solids by GC and NMR to determine the % alcohol, slurrying in methanol at 30° C. for 1 hour (5 mL of methanol per g of compound) if necessary to remove alcohol impurity.

Example 71

Preparation of 4-(2-(5-(trifluoromethyl)-1H-imidazol-2-yl)-pyridin-4-yloxy)-N-methyl-2-nitrobenzenamine

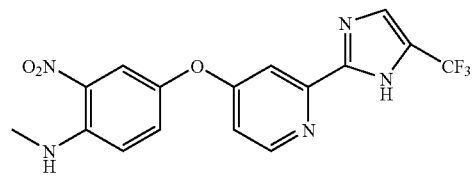

4-(2-(5-(trifluoromethyl)-1H-imidazol-2-yl)pyridin-4-yloxy)-N-methyl-2-nitrobenzenamine can be prepared according to the following procedure:
1. Equip a 2 L round bottom flask (3 necked) with a mechanical stirrer, internal temperature probe, temperature controller and condenser.
2. Charge the reactor with water (590 mL) via powder funnel.
3. Begin stirring the mixture and charge the reactor with sodium acetate (240 g).
4. Rinse the flask used for the sodium acetate charge with water (30 mL).
5. Heat the reaction to 50° C.
6. Add 3,3-dibromo-1,1,1-trifluoropropan-2-one (395 g) portion-wise at 50° C. keeping the internal temperature of the reaction under 100° C.
7. Heat the reaction to an internal temperature of 100° C.
8. After stirring the reaction for 1 hour at 100° C., remove a sample for analysis.
9. Keep stirring the reaction at 100° C. until the starting material is <1.5%.
10. Once the reaction is complete cool the reaction mixture to <65° C.
11. While the reaction is cooling, equip a 5 L round bottom flask jacketed 4 necked) with an internal temperature probe, temperature controller, reflux condenser and mechanical stirrer.
12. Charge the 5 L reactor with ethyl acetate (500 mL) via a powder funnel and begin stirring.

13. Charge the 5 L reactor with 4-(4-(methylamino)-3-nitrophenoxy)pyridine-2-carbaldehyde (200 g) via powder funnel.
14. Rinse the powder funnel with ethyl acetate (200 mL) into the 5 L reactor.
15. Charge the 5 L reactor with 95% ethanol (1.3 L).
16. Transfer the pyruvaldehyde reaction mixture from the 2 L reactor to the 5 L reactor. Temperature of the mixture at this point is ~35° C.
17. Slowly add conc. NH₄OH (1.3 L) portion wise monitoring the temperature. The reaction is exothermic so the first 500 mL should be added in portions keeping the internal temperature under 50° C. The total addition time is ~25 minutes. Elevated temperatures cause the final product to become redder.
18. Heat the 5 L reactor to 50° C.
19. Stir the reaction mixture at 50° C. Solution at this point is usually reddish-orange in color.
20. Monitor the reaction every hour until the reaction is complete.
21. Once the reaction is deemed complete, cool the reaction mixture to 0° C. for 2 hours.
22. Isolate the product by filtration through a coarse fritted glass filter.
23. Rinse the reactor with cold ethanol (150 mL). Transfer the rinse to the filter.
24. Charge the 5 L reactor with water (2 L).
25. Stir and cool the reactor to 10° C.
26. Transfer the wet cake from the filter to the 5 L reactor.
27. Stir at 10° C. for 60 minutes.
28. Filter the product through a coarse fritted glass filter.
29. Rinse the reactor with water (250 mL). Transfer the rinse to the filter.
30. Dry the wet cake on the filter for 1 hour.
31. Transfer the product to a 2 L round bottom flask (single neck) and tumble dry using a rotary evaporator with a bath temperature of 45° C. until a constant weight is recorded.

Example 72

Preparation of 4-(2-(5-(trifluoromethyl)-1H-imidazol-2-yl)pyridin-4-yloxy)-N1-methylbenzene-1,2-diamine

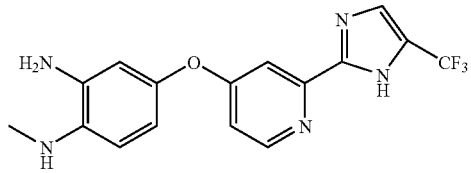

4-(2-(5-(trifluoromethyl)-1H-imidazol-2-yl)pyridin-4-yloxy)-N1-methylbenzene-1,2-diamine can be prepared according to the following procedure:
1. Equip a 2 L round bottom flask (4 neck) with a mechanical stirrer, internal temperature probe, temperature controller, nitrogen purge and reflux condenser.
2. Charge the reactor with EtOH (125 mL) via powder funnel. Begin stirring rapidly.
3. Charge the reactor with 4-(2-(5-(trifluoromethyl)-1H-imidazol-2-yl)pyridin-4-yloxy)-N-methyl-2-nitrobenzenamine (50 g) via powder funnel.
4. Heat the reaction to 50° C.
5. While the reaction is heating, charge a 250 mL Erlenmeyer with water (75 mL) via powder funnel. Begin stirring rapidly.
6. Charge the 250 mL Erlenmeyer with 3.0 eq. sodium carbonate (41.92 g) via a powder funnel.
7. Stir the mixture until all the solids are dissolved.
8. Once the suspension reaches 50° C., transfer the sodium carbonate mixture from the 250 mL Erlenmeyer to the reaction mixture via powder funnel.
9. Charge a 250 mL Erlenmeyer with water (75 mL) via powder funnel. Begin stirring rapidly.
10. Charge the 250 mL Erlenmeyer with 1.0 eq. sodium dithionite (22.95 g) via powder funnel just before addition to the reaction flask.
11. Rapidly stir the solids until they are mostly dissolved.
12. Quickly transfer the sodium dithionite mixture from the 250 mL Erlenmeyer to the reaction mixture via powder funnel.
13. Stir the reaction at 50° C. for 30 minutes.
14. Charge a 250 mL Erlenmeyer with water (75 mL) via powder funnel. Begin stirring rapidly.
15. Charge the 250 mL Erlenmeyer with 1.0 eq. sodium dithinonite (22.95 g) via powder funnel just before addition to the reaction flask.
16. Rapidly stir the solids until they are mostly dissolved.
17. Quickly transfer the sodium dithionite mixture from the 250 mL Erlenmeyer to the reaction mixture via powder funnel.
18. Stir the reaction at 50° C. for 30 minutes.
19. Charge a 250 mL Erlenmeyer with water (150 mL) via powder funnel.
20. Charge the 250 mL Erlenmeyer with 2.0 eq. sodium dithinonite (45.90 g) via powder fuel just before addition to the reaction flask.
21. Rapidly stir the solids until they are mostly dissolved.
22. Quickly transfer the sodium dithionite mixture from the 250 mL Erlenmeyer to the reaction mixture via powder funnel.
23. Stir the reaction at 50° C. for 60 minutes.
24. A sample is taken to verify the reaction completion.
25. If the reaction is ≧98% complete, go to step 36. If not then continue to step 26.
26. Charge the 2 L reaction flask with 1.0 eq. sodium dithinonite (22.95 g) via powder funnel.
27. Rapidly stir the reaction mixture at 50° C. for 60 minutes.
28. A sample is taken to verify the reaction completion.
29. If the reaction is ≧98% complete, go to step 36. If not then continue to step 30.
30. Charge the 2 L reaction flask with 1.0 eq. sodium carbonate (13.97 g) via a powder funnel.
31. Rapidly stir the reaction mixture at 50° C. for 15 minutes.
32. Charge the 2 L reaction flask with 1.0 eq. sodium dithinonite (22.95 g) via powder funnel.
33. Rapidly stir the reaction mixture at 50° C. for 60 minutes.
34. A sample is taken to verify the reaction completion.
35. When the reaction is ≧98% complete, go to step 36
36. Once the reaction is deemed complete, charge the 2 L reaction flask with water (125 mL) via a powder funnel.
37. Cool the reaction mixture to 10° C. and stir for 1 hour.
38. Isolate the product by filtration through a course fritted glass filter.
39. Rinse the reactor with water (50 mL). Transfer the rinse to the filter.
40. Dry the wet cake on the filter until it no longer drips.
41. Charge the 2 L reaction flask with water (500 mL) via a powder funnel.
42. Transfer the cake back into the reaction flask via a powder funnel.
43. Stir material at room temperature for 60 min.

44. Isolate the product by filtration through a course fritted glass filter.
45. Rinse the reactor with water (25 mL). Transfer the rinse to the filter.
46. Dry the wet cake on the filter for about 1 hour.
47. Transfer the product to a 2 L round bottom flask (single neck) and slowly tumble dry using a rotary evaporator with a bath temperature of 50° C. until a constant weight is recorded.

Example 73

Preparation of {1-Methyl-5-[2-(5-trifluoromethyl-1H-imidazol-2-yl)-pyridin-4-yloxy]-1H-benzo-imidazol-2-yl}-(4-trifluoromethyl-phenyl)-amine

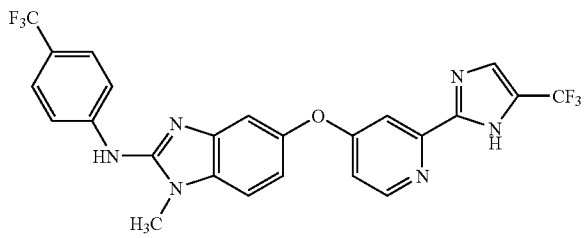

{1-Methyl-5-[2-(5-trifluoromethyl-1H-imidazol-2-yl)-pyridin-4-yloxy]-1H-benzoimidazol-2-yl}-(4-trifluoromethyl-phenyl)-amine can be prepared according to the following procedure:
1. Equip a 2-L, 4-neck round bottom flask with a mechanical stirrer, internal temperature probe, temperature controller, nitrogen purge and condenser.
2. Charge the reactor with 4-(2-(5-(trifluoromethyl)-1H-imidazol-2-yl)pyridin-4-yloxy)-NI-methylbenzene-1,2-diamine (200 g) via powder funnel.
3. Charge the reactor with acetonitrile (1 L) via powder funnel.
4. Begin stirring the mixture at ambient temperature and under a nitrogen atmosphere.
5. After 20±5 min, charge the reactor with 4-trifluoromethylphenyl isothiocyanate (104 g) via powder funnel.
6. A sample is taken 30 min after addition of the isothiocyanate to verify reaction completion.
7. Once the reaction is complete, filter the mixture through a coarse fritted glass filter.
8. Rinse the reactor with MeCN (200 mL). Transfer the rinse to the filter.
9. Wash the removed solids with MeCN (200 mL).
10. Transfer the filtrate to a 3-L, 4-neck round bottom flask with a mechanical stirrer, internal temperature probe, temperature controller, nitrogen purge and condenser.
11. Charge the reactor with N,N-diisopropylethylamine via powder funnel.
12. Charge the reactor with 2-chloro-1,3-dimethylimidazolinium chloride via powder funnel in four equivalent portions every 10 min (total addition time of 30 min). After the final addition, allow the reaction mixture to stir an additional 10 min.
13. Heat the reaction to 50° C.±5° C.
14. A sample is taken 30 minutes after heating the mixture to verify reaction completion.
15. Once the reaction is complete, transfer the reaction mixture through an in-line 0.2 μm capsule filter to a 3-L round bottom flask equipped as in step 10.
16. Add the water via powder funnel.
17. Heat the reaction to 50° C.±5° C.
18. After heating for 2 h, allow the reaction mixture to cool to 20-25° C. and stir an additional 1 h.
19. Isolate the product by filtration through a medium fritted glass filter.
20. Rinse the reactor with 2:1 MeCN/water (300 mL). Transfer the rinse to the filter.
21. Wash the filter cake with 2:1 MeCN/water (300 mL).
22. Dry the wet cake on the filter for about 1 hour.
23. Transfer the product to a drying dish and dry the material in a vacuum oven at 70±5° C. with a small bleed of nitrogen until the amount of residual MeCN (acetonitrile) is less than 410 ppm.
24. To recrystallize, product is heated to reflux in 15 volumes (weight to volume) of EtOH in a reactor equipped with a mechanical stirrer, internal temperature probe, temperature controller, nitrogen purge and condenser.
25. The mixture is refluxed for 30 minutes when a distillation head is substituted for the condenser.
26. EtOH is distilled off until 4 volumes remain. Heating is stopped and one volume of water is added.
27. The mixture is allowed to cool to 0-5° C.
28. Isolate the product by filtration through a medium fitted glass filter.
29. Rinse the reactor with 4:1 EtOH/water (1 volume). Transfer the rinse to the filter.
30. Wash the filter cake with water (1 volume).
31. Dry the wet cake on the filter for about 1 hour.
32. Transfer the product to a drying dish and dry the material in a vacuum oven at 50° C.±° C. with a small bleed of nitrogen until constant weight is attained.

Example 74

Preparation of {1-Methyl-5-[2-(5-trifluoromethyl-1H-imidazol-2-yl)-pyridin-4-yloxy]-1H-benzo-imidazol-2-yl}-(4-trifluoromethyl-phenyl)-amine 4-Trifluoromethylphenyl isothiocyanate (200 mg, 1 mmol) was added to a mixture of 4-(2-(5-(trifluoromethyl)-1H-imidazol-2-yl)pyridin-4-yloxy)-N1-methylbenzene-1,2-diamine (350 mg, 1 mmol) in 3 mL of acetonitrile. After stirring for 20 min at ambient temperature, HPLC analysis showed complete conversion. Triethylamine (0.3 mL, 2.2 mmol) was added followed by 2-chloro-1-methylpyridinium iodide (270 mg, 1.05 mmol). The reaction mixture was heated to 50° C. for 5 h. The heating was stopped and 1.5 mL of water was added. After stirring the mixture for 2 h, the solid was collected by filtration and washed with 2:1 acetonitrile/water (3×1 mL) to afford 317 mg (61%) of the title compound.

Example 74a

Preparation of 4-(2-(5-(trifluoromethyl)-1H-imidazol-2-yl)pyridin-4-yloxy)-N-methyl-2-nitrobenzenamine

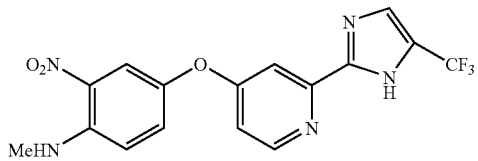

NaOMe (1.5 mL, 6.3 mmol, 25 wt % in MeOH) was added to a mixture of 4-(4-(methylamino)-3-nitrophenoxy)pyridine-2-carbonitrile (1.72 g, 6.3 mmol) in 1-PrOH (10 mL). The mixture was heated to 50° C. (internal temperature).

After heating for 1 h, HPLC analysis indicated complete conversion of starting material. NH₄OAc (1.46 g, 18.9 mmol) was added and the mixture heated to 70° C. After 1 h at 70° C., the mixture was heated to 85° C. Simultaneously, 3-bromo-1,1,1-trifluoroacetone (0.8 mL, 7.56 mmol) was added in 4×0.2-mL portions every 30 min. The mixture was heated at 85° C. for 20 h. The mixture was then allowed to cool to ambient and water (10 mL) was added. After stirring for several hours, the mixture was cooled in an ice/water bath. After 1 h in the ice/water bath, the solid was collected by filtration and washed with 1:1 1-PrOH/water (2×7 mL). The solid was dried in a vacuum oven at 50° C. for ca. 16 h to afford 0.982 g (41%) of the title compound.

Example 74b

Preparation of 4-chloro-2-(5-(trifluoromethyl)-1H-imidazol-2-yl)pyridine

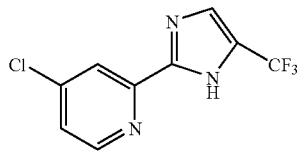

NaOMe (0.46 mL, 2 mmol, 25 wgt % in MeOH) was added to a mixture of 4-chloro-2-cyano-pyridine (277 mg, 2 mmol) in 1-PrOH (3 mL). The mixture was heated to 50° C. (Reaction-Block temperature). After heating for 1 h, HPLC analysis indicated complete conversion of starting material. The mixture was heated to 70° C. and NH₄OAc (462 mg, 6 mmol) was added. After 1 h at 70° C., the mixture was heated to 85° C. Simultaneously, 3-bromo-1,1,1-trifluoroacetone (0.25 mL, 2.4 mmol) was added in 4×0.063-mL portions every 30 min. The mixture was heated at 85° C. for ca. 20 h. The crude product was 72.4% (LCAP) by HPLC analysis and was confirmed by LC-MS analysis.

Example 74c

4-Chloro-2-cyano-pyridine

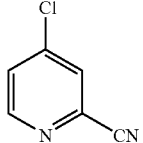

4-Chloro-2-pyridinecarboxamide (93.9 g, 0.6 moles) and TEA (125 mL, 0.9 moles) in EtOAc (500 mL) was cooled to 0.2° C. via an external chiller unit. TFAA (92 mL, 0.66 moles) was added via addition funnel over 40 min. The internal temperature rose to 10° C. during the addition. The temperature at the completion of the addition was 0.0° C. After addition, the chiller was turned off. After an additional 30 min, HPLC analysis showed 4.3% (LCAP) of the starting material. An additional 8.3 mL (0.06 moles) of TFAA was added. After stirring the reaction mixture for an additional 20 min, HPLC analysis indicated complete conversion. 10% Aqueous K₂CO₃ (w/v, 500 mL) was added. The internal temperature rose from 13.7 to 22.0° C. The mixture was transferred to a separatory funnel after stirring for 20 min. The layers were separated and the aqueous layer extracted with EtOAc (150 mL). The combined organic layers were washed with 10% aqueous citric acid (w/v, 300 mL), dried (Na₂SO₄), filtered, and concentrated. The crude product was dried in a vacuum oven at 50° C. for 16 h to afford 72.85 g (87%) of the title compound: ¹H NMR (400 MHz, CDCl₃) δ 8.6 (m, 1 H), 7.7 (m, 1 H), 7.5 (m, 1H); ¹³C NMR (100 MHz, CDCl₃) δ 151.8, 145.3, 134.9, 128.7, 127.4, 116.1; HPLC>99% (LCAP).

Example 74d 4-(4-Methylamino-3-nitro-phenoxy)-pyridine-2-carbonitrile

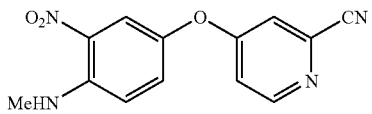

A mixture of 4-chloro-2-cyano-pyridine (6.9 g, 0.05 moles), 4-methylamino-3-nitrophenol (8.4 g, 0.05 moles), and K₂CO₃ (10.4 g, 0.075 moles) in DMSO (80 mL) was heated to 60° C. After 11.5 h, HPLC analysis indicated complete conversion of both starting materials. After cooling to 20° C., water (240 mL) was added to the reaction mixture. The temperature rose to 40° C. before decreasing to ambient temperature. The solid was collected by filtration and washed with water (2×40 mL). The solid was then slurried in heptane (40 mL). The solid was collected and washed with heptane (40 mL). The crude product was dried in a vacuum oven at 50° C. for 16 h to afford 10.33 g (76%) of the title compound: ¹H NMR (400 MHz, DMSO-d₆) δ 8.5 (m, 1 H), 8.2 (m, 1 H), 7.9 (m, 1 H), 7.7 (m, 1 H), 7.5 (m, 1 H), 7.2 (m, 1 H), 7.1 (m, 1 H), 3.0 (s, 3 H); ¹³C NMR (100 MHz, DMSO-d₆) 165.1, 152.9, 144.4, 140.6, 134.1, 130.4, 130.1, 117.9, 117.1, 117.0, 116.5, 114.9, 29.8; APCI MS [M+H]⁺=271; HPLC >99% (LCAP).

Example 74e 4-(4-Methylamino-3-amino-phenoxy)-pyridine-2-carbonitrile

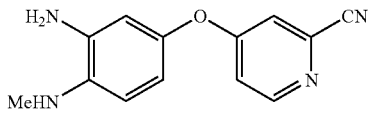

4-(4-Methylamino-3-nitro-phenoxy)-pyridine-2-carbonitrile (5.0 g, 0.019 moles) in EtOH (15 mL) was heated to 40° C. Na₂CO₃ (4.7 g, 0.044 moles) was added followed by H₂O (8.4 mL). Na₂S₂O₄ (3.3 g, 0.019 moles) was added followed by H₂O (10 mL). The temperature rose from 41.7 to 49.5° C. After cooling down to 41.7° C., Na₂S₂O₄ (3.3 g, 0.019 moles) was added followed by H₂O (10 mL). The temperature rose to 44.5° C. After cooling down to 36.7° C., Na₂S₂O₄ (6.6 g, 0.038 moles) was added followed by H₂O (20 mL). The temperature rose to 44.0° C. HPLC analysis showed 4.1% (LCAP) of the starting material. Additional Na₂S₂O₄ (3.3 g, 0.019 moles) was added. After stirring an additional 15 min, heat was removed and H₂O (12.5 mL) was added. At 25° C., additional Na₂CO₃ (1.3 g, 0.012 moles) was added and the mixture cooled in an ice/water bath. At less than 5° C., the mixture was allowed to age for 30 min (final temperature of 1.5° C.). The solid was collected by filtration and washed with H₂O (10 mL followed by 5 mL). The solid was dried on the filter for 30 min and then transferred to the reaction flask and H₂O (50 mL) added. The mixture was stirred for 45 min. The solid was then collected by filtration and washed with H₂O (2×10 mL). The crude product was dried in a vacuum oven at 50° C. for 16 h to afford 3.50 g (76%) of the title compound: ¹H NMR (400 MHz, DMSO-d₆) δ 8.5 (m, 1 H), 7.5 (m, 1 H), 7.1 (m, 1 H), 6.4 (m, 1 H), 6.3 (m, 2 H), 4.8 (s, 2 H), 4.7 (s, 1 H), 2.7 (s, 3H); APCI MS [M+H]$^+$=241; HPLC >99% (LCAP).

Example 74f

4-[1-Methyl-2-(4-(trifluoromethyl)phenylamino)-1H-benzoimidazol-5-yloxy]-pyridine-2-carbonitrile

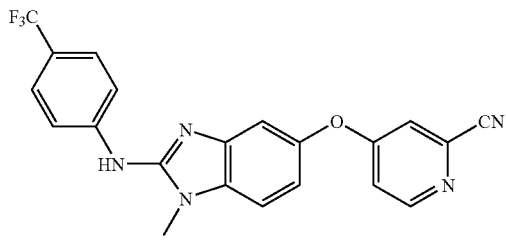

4-(Trifluoromethyl)phenyl isothiocyanate (9.65 g, 0.0475 moles) was added to a solution of 4-(4-methylamino-3-amino-phenoxy)-pyridine-2-carbonitrile (12.0 g, 0.05 moles) in MeCN (60 mL). HPLC analysis indicated complete conversion of the amine after 40 min. The mixture was filtered and the removed solids washed with MeCN (2×12 mL). DIPEA (17.5 mL, 0.1 moles) was added to the filtrate. 2-Chloro-1,3-dimethylimidazolinium chloride (DMC) was added in 4×2.11-g portions (8.44 g, 0.05 moles) every 10 min. After the final addition, the mixture was allowed to stir an additional 10 min when HPLC analysis indicated complete conversion. The mixture was then heated to 50° C. (internal temperature). After 45 min at 50° C., HPLC analysis indicated complete conversion to the product. The mixture was allowed to cool to ambient temperature and then H$_2$O (45 mL) was added. The reaction mixture was initially homogeneous before compound began to precipitate from the mixture. After stirring for 2 h, the solid was collected by filtration and washed with 2:1 MeCN/H$_2$O (2×20 mL). The crude product was dried in a vacuum oven at 50° C. for 16 h to afford 16.10 g (78%) of the title compound $^1$H NMR (400 MHz, DMSO-d$_6$) δ 9.5 (m, 1 H), 8.5 (m, 1 H), 8.0 (m, 2 H), 7.7 (m, 2H), 7.6 (m, 1H), 7.4 (m, 1 H), 7.3 (m, 1 H), 7.1 (m, 1 H), 6.9 (m, 1 H), 3.7 (m, 3 H); APCI MS [M+H]$^+$=410; HPLC >99% (LCAP).

Example 74g

{1-Methyl-5-[2-(5-trifluoromethyl-1H-imidazol-2-yl)-pyridin-4-yloxy]-1H-benzoimidazol-2-yl}-(4-trifluoromethyl-phenyl)-amine

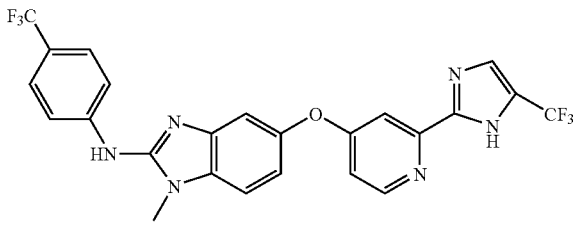

NaOMe (0.23 mL, 1 mmol, 25 wgt % in MeOH) was added to a mixture of Example 74f (409 mg, 1 mmol) in MeOH (4 mL). After 1 h at ambient temperature HPLC analysis indicated 46.2% (LCAP) of the starting material. The mixture was heated to 50° C. (Reaction-Block temperature). After heating for 1 h, HPLC analysis indicated 4.1% (LCAP) of the starting material remained. NH$_4$OAc (231 mg, 3 mmol) was added followed by 3-bromo-1,1,1-trifluoroacetone (0.13 mL, 1.2 mmol). The mixture was heated at 50° C. for about 20 h. Additional 3-bromo-1,1,1-trifluoroacetone (0.06 mL, 0.58 mmol) was added and the mixture heated to 60° C. After 24 h at 60° C., the mixture was allowed to cool to ambient temperature. Water (4 mL) was added followed by EtOAc (4 mL). The layers were separated and the aqueous layer extracted with EtOAc. The combined organic layers were dried (Na$_2$SO$_4$), filtered, and concentrated. The crude product was dissolved in IPA (4 mL). Methanesulfonic acid (0.020 mL) was added to 1 mL of solution of the IPA solution. The mixture was heated to 80° C. overnight. The mixture was then cooled to ambient temperature and concentrated to give the title compound: APCI MS [M+H]$^+$=519.

Example 74h

{1-Methyl-5-[2-(5-trifluoromethyl. 1H-imidazol-2-yl)-pyridin-4-yloxy]-1H-benzoimidazol-2-yl}-(4-trifluoromethyl-phenyl)-amine

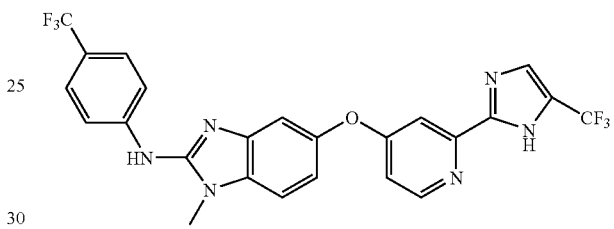

NaOMe (0.23 mL, 1 mmol, 25 wgt % in MeOH) was added to a mixture of Example 74f (409 mg, 1 mmol) in 1-PrOH (2 mL). The mixture was heated to 50° C. (Reaction-Block temperature). After heating for 1 h, HPLC analysis indicated complete conversion of the starting material. The mixture was heated to 70° C. and NH$_4$OAc (231 mg, 3 mmol) was added. After 1 h at 70° C., the mixture was heated to 85° C. Simultaneously, 3-bromo-1,1,1-trifluoroacetone (0.13 mL, 1.2 mmol) was added in 4×0.033-mL portions every 30 min. The mixture was heated at 85° C. for ca. 20 h. The mixture was allowed to cool to ambient temperature and water (2 mL) was added. After stirring for several hours, the solid was collected by filtration and washed with 1:1 1-PrOH/water (2×3 mL). The solid was dried in a vacuum oven at 50° C. for ca. 16 h to afford 0.11 g (21%) of the title compound.

Example 75

Preparation of {1-Methyl-5-[2-(5-trifluoromethyl-1H-imidazol-2-yl)-pyridin-4-yloxy]-1H-benzo-imidazol-2-yl}-(4-trifluoromethyl-phenyl)-amine 4-Trifluoromethylphenyl isothiocyanate (200 mg, 1 mmol) was added to a mixture of 4-(2-(5-(trifluoromethyl)-1H-imidazol-2-yl)pyridin-4-yloxy)-N1-methylbenzene-1,2-diamine (350 mg, 1 mmol) in 3 mL of acetonitrile. After stirring for 20 min at ambient temperature, HPLC analysis showed complete conversion. A mixture of thiourea (553 mg, 1 mmol) in POCl$_3$ (3 mL) was stirred at ambient temperature. After 4 h, the mixture was heated to approximately 50° C. After heating for 2 h, HPLC analysis indicated completion of reaction:

Example 76

Raf/Mek Filtration Assay

Buffers
  Assay buffer: 50 mM Tris, pH 7.5, 15 mM MgCl$_2$, 0.1 mM EDTA, 1 mM DTT
  Wash buffer: 25 mM Hepes, pH 7.4, 50 mM sodium pyrophosphate, 500 mM NaCl
  Stop reagent: 30 mM EDTA Materials
  Raf, active: Upstate Biotech #14-352
  Mek, inactive: Upstate Biotech #14-205
  $^{33}$P-ATP: NEN Perkin Elmer #NEG 602 h
  96 well assay plates: Falcon U-bottom polypropylene plates #35-1190
  Filter apparatus: Millipore #MAVM 0960R
  96 well filtration plates: Millipore Immobilon 1 #MAIP NOB
  Scintillation fluid: Wallac OptiPhase "SuperMix" #1200-439

Assay Conditions
  Raf approximately 120 pM
  Mek approximately 60 nM
  $^{33}$P-ATP 100 nM
  Reaction time 45-60 minutes at room temperature Assay Protocol
  Raf and Mek were combined at 2× final concentrations in assay buffer (50 mM Tris, pH 7.5, 15 mM MgCl$_2$. 0.1 mM EDTA and 1 mM DTT) and dispensed 15 μL per well in polypropylene assay plates (Falcon U-bottom polypropylene 96 well assay plates #35-1190. Background levels are determined in wells containing Mek and DMSO without Raf.
  To the Raf/Mek containing wells was added 3 μl of 10× of a raf kinase inhibitor test compound diluted in 100% DMSO. The raf kinase activity reaction was started by the addition of 12 μL per well of 2.5×$^{33}$P-ATP diluted in assay buffer. After 45-60 minutes, the reactions were stopped with the addition of 70 μL of stop reagent (30 mM EDTA). Filtration plates were pre-wetted for 5 min with 70% ethanol, and then rinsed by filtration with wash buffer. Samples (90 μl) from the reaction wells were then transferred to the filtration plates. The filtration plates were washed 6× with wash buffer using Millipore filtration apparatus. The plates were dried and 100 μL per well of scintillation fluid (Wallac OptiPhase "SuperMix" #1200-439) was added. The CPM is then determined using a Wallac Microbeta 1450 reader.

Example 77

Assay 2: Biotinylated Raf Screen

In Vitro Raf Screen
The activity of various isoforms of Raf serine/threonine kinases can be measured by providing ATP, MEK substrate, and assaying the transfer of phosphate moiety to the MEK residue. Recombinant isoforms of Raf were obtained by purification from sf9 insect cells infected with a human Raf recombinant baculovirus expression vector. Recombinant-kinase inactive MEK was expressed in E. Coli and labeled with Biotin post purification. For each assay, test compounds were serially diluted in DMSO then mixed with Raf (0.50 nM) and kinase inactive biotin-MEK (50 nM) in reaction buffer plus ATP (1 μM). Reactions were subsequently incubated for 2 hours at room temperature and stopped by the addition of 0.5 M EDTA. Stopped reaction mixture was transferred to a neutradavin-coated plate (Pierce) and incubated for 1 hour. Phosphorylated product was measured with the DELFIA time-resolved fluorescence system (Wallac), using a rabbit anti-p-MEK (Cell Signaling) as the primary antibody and europium labeled anti-rabbit as the secondary antibody. Time resolved fluorescence was read on a Wallac 1232 DELFIA fluorometer. The concentration of each compound for 50% inhibition (IC$_{50}$) was calculated by non-linear regression using XL Fit data analysis software.

Using the procedures of Examples 76 or 77, the compounds of Examples 1-64 were shown to have a raf kinase inhibitory activity at an IC$_{50}$ of less than 5 μM.

Example 78

Inhibition of Melanoma Tumor Growth

3×10$^6$ A375M human melanoma cells were implanted subcutaneously into the right flank of 10-12 week old female Nu/Nu mice weighing approximately 24 g. When the average tumor volume reached approximately 150 mm$^3$ (17 days post-implant), the mice were randomized by tumor volume into four groups of nine mice each and treatment with a compound of the invention was started. The mice were dosed by oral gavage every day for 14 days with either vehicle alone, or with 10 mg/kg, 30 mg/kg or 100 mg/kg of the compound of Example 25 all in a volume of 0.2 mL. The tumor volume was measured twice per week using digital calipers. The mean tumor volume is shown in FIG. 1.

Example 79

Inhibition of Raf Kinase Signaling in Melanoma Cells

As in Example 78, 3×10$^6$ A375M human melanoma cells were implanted subcutaneously into the right flank of 10-12 week old female Nu/Nu mice weighing approximately 24 g. When the average tumor volume reached approximately 150 mm$^3$ (17 days post-implant), the mice were randomized by tumor volume into four groups, and were dosed by oral gavage every day for 5 days with vehicle alone, or with 10 mg/kg, 30 mg/kg or 100 mg/kg of the compound of Example 25 all in a volume of 0.2 mL. At 4 and 24 hours post-dose, the mice were euthanized, tumors harvested and flash-frozen.

Figure 2A:
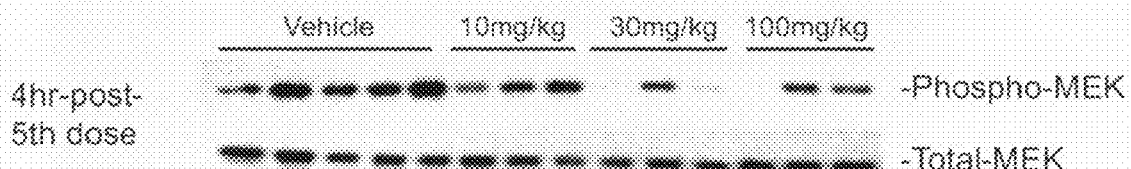
FIGS. 2A and 2B are PAGE slides showing the inhibition of downstream signaling from Raf kinase in A375M human melanoma tumor cells in mice 4-(FIG. 2A) and 24-hours (FIG. 2B) after treatment with a compound of the invention, as described in Example 79.
Figure 2B:
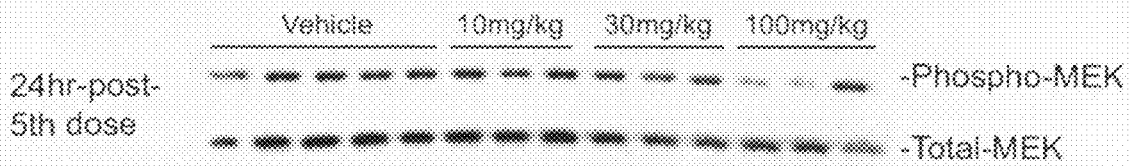

The frozen tumors were thawed on ice, weighed and then homogenized in RIPA buffer with Roche Complete, Mini EDTA-free protease inhibitor cocktail tablets (2 tablets per 25 mL of buffer), 1 mM phenylmethylsulfonylfluoride (PMSF) and 1× Sigma Phosphatase Inhibitor Cocktail II, using the Roche Magna-lyser (2×1 minute cycles at 6500 rpm at 4° C.). For every 100 mg of tumor tissue, 1 mL of RIPA lysis buffer was added. The homogenates were centrifuged at 14K RPM for 20 minutes in a microfuge at 4° C., followed by further homogenization using Qiagen Qiashredders (9K RPM for 2 minutes at 4° C.). The protein concentration was determined using the Pierce BCA protein assay and then 20 μg of each sample was loaded per well in a 4-20% Tris-Glycine SDS-polyacrylamide gel. Following PAGE, protein was transferred to nitrocellulose membranes, blocked (5% non-fat milk powder in TBST) for 1 hour at room temperature and then probed overnight at 4° C. using a 1:1000 dilution (in blocking buffer) of rabbit polyclonal anti-phospho-ERK 1/2 antibody (Cell Signalling #9101), rabbit polyclonal anti-phospho-MEK antibody (Cell Signaling #9121), rabbit polyclonal anti-ERK1/2 antibody (Cell Signalling #9102) or rabbit polyclonal anti-MEK antibody (Cell Signalling #9122). The membranes were then washed 5-times (5 minutes each) with TBST at room temperature and an HRP-labeled goat-anti-rabbit antibody was added at 1:5000 dilution in all blots (in blocking buffer) and incubated at room temperature for 1 hour. The membranes were then washed 5-times (5 minutes each) with TBST, and the membranes were incubated with Pierce Super-Signal for 4 mins, followed by exposure onto film for range of time exposures from 1 sec to 20 minutes. The results for the 4 and 24 hours post-dose samples is shown in FIGS. 2A and 2B, respectively.

Example 80

Figure 3:
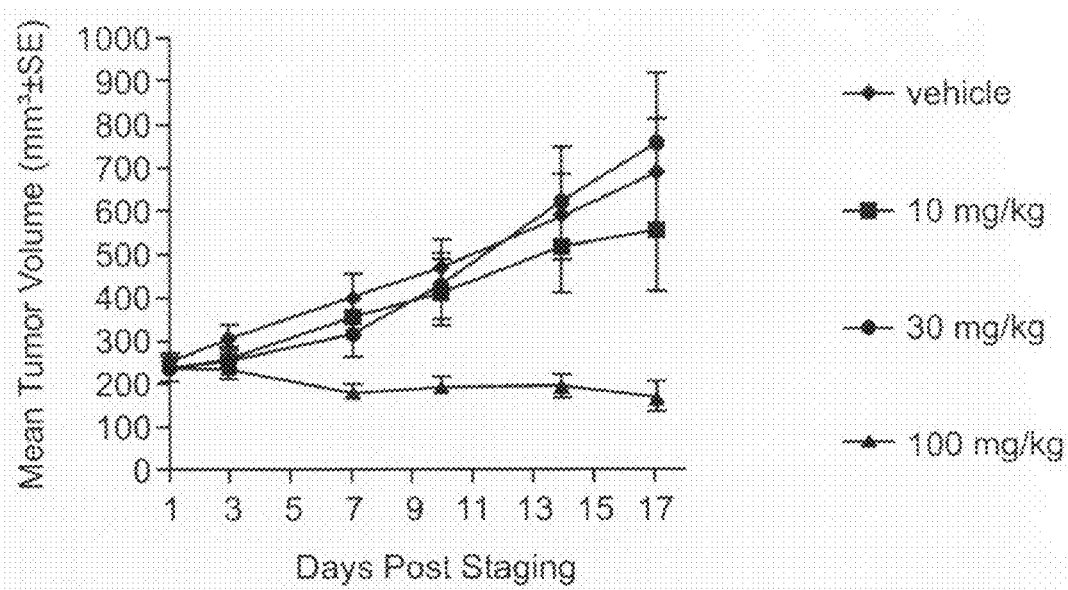
FIG. 3 is a graph showing the mean reduction in tumor volume of HT29P human colon cancer tumors in mice when treated with a compound of the invention, as described in Example 80.

Inhibition of Colon Cancer Tumor Growth $2 \times 10^6$ HT29P human colon cancer cells were implanted subcutaneously into the right flank of 10-12 week old female Nu/Nu mice weighing approximately 24 g. When the average tumor volume reached approximately 250 mm$^3$ (14 days post-implant), the mice were randomized by tumor volume into four groups of ten and treatment with a compound of the invention was started. The mice were dosed by oral gavage every day for 14 days with either vehicle alone, or with 10 mg/kg, 30 mg/kg or 100 mg/kg the compound of Example 25 all in a volume of 0.2 mL. The tumor volume was measured twice per week using digital calipers. The mean tumor volume is shown in FIG. 3.

Example 81

Figure 4A:
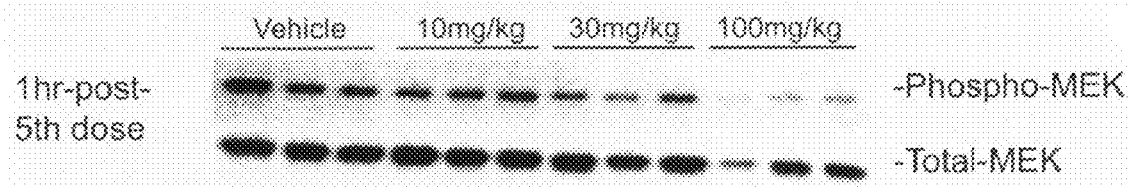
FIGS. 4A, 4B, and 4C are PAGE slides showing the inhibition of downstream signaling from Raf kinase in HT29P human colon cancer tumor cells in mice 1 hour (FIG. 4A), 4 hours (FIG. 4B), and 24 hours (FIG. 4C) after treatment with a compound of the invention, as described in Example 81.
Figure 4B:
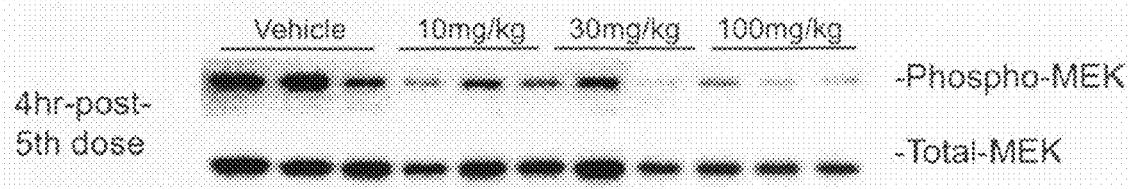
Figure 4C:
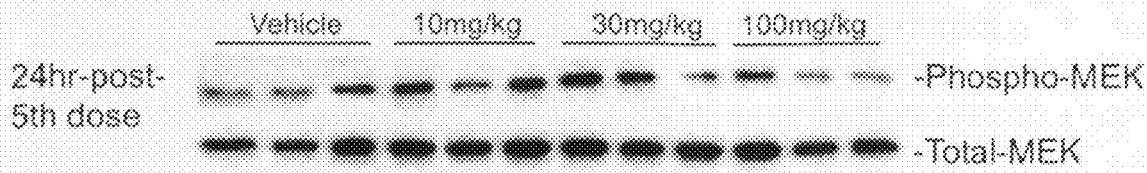

Inhibition of Raf Kinase Signaling in Colon Cancer Cells $3 \times 10^6$ HT29P human colon cancer cells were implanted subcutaneously into the right flank of 10-12 week old female Nu/Nu mice weighing approximately 24 g. When the average tumor volume reached approximately 150 mm$^3$ (17 days post-implant), the mice were randomized by tumor volume into four groups and treatment with a compound of the invention was started. The mice were dosed by oral gavage every day for 5 days with either vehicle alone, or with 10 mg/kg, 30 mg/kg or 100 mg/kg of the compound of Example 25 all in a volume of 0.2 mL. At 1, 4, and 24 hours post-dose, mice were euthanized, tumors harvested and flash-frozen. The frozen tumors were then treated according to the procedure of Example 79. The results for the 1, 4, and 24 hours post-dose samples is shown in FIGS. 4A, 4B, and 2C, respectively.

Example 82

Inhibition of Raf Kinase Signaling with the Compound of Example 1 in an In Vitro Biochemical Assay In Vitro Raf Assay The inhibitory effect of Compound of Example 1: {1-Methyl-5-[2-(5-trifluoromethyl-1H-imidazol-2-yl)-pyridin-4-yloxy]-1H-benzoimidazol-2-yl}-(4-trifluoromethyl-phenyl)-amine on wild-type B-Raf, wild-type c-Raf and mutant B-Raf (V600E) was determined using the following biotinylated assay. The kinase activity of the various isoforms of Raf serine/threonine kinases were measured by providing ATP, a recombinant kinase inactive MEK substrate and assaying the transfer of phosphate moiety to the MEK residue. Recombinant full length MEK with an inactivating K97R ATP binding site mutation (rendering it kinase inactive) was expressed in E. coli and labelled with Biotin post purification. The MEK cDNA was subcloned with an N-terminal (his)$_6$ tag and expressed in E. coli and the recombinant MEK substrate was purified from E. coli lysate by nickel affinity chromatography followed by anion exchange. The final MEK substrate preparation was biotinylated (Pierce EZ-Link Sulfo-NHS-LC-Biotin) and concentrated to 11.25 µM. Recombinant B-Raf, c-Raf and mutant B-Raf were obtained by purification from sf9 insect cells infected with the corresponding human Raf recombinant expression vectors. The recombinant Raf isoforms were purified via a Glu antibody interaction or by Metal Ion Chromatography.

For each assay, the compound of Example 1 was serially diluted in DMSO and then mixed with B-Raf, c-Raf or mutant B-Raf (0.50 nM each). The kinase inactive biotin-MEK substrate (50 nM) was added in reaction buffer plus ATP (1 µM). The reaction buffer contained 30 mM Tris-HCL$_2$ pH 7.5, 10 mM MgCl$_2$, 2 mM DTT, 4 mM EDTA, 25 mM beta-glycerophosphate, 5 mM MnCl$_2$, and 0.01% BSA/PBS. Reactions were subsequently incubated for 2 hours at room temperature and stopped by the addition of 0.5 M EDTA. Stopped reaction mixture was transferred to a neutradavin-coated plate (Pierce) and incubated for 1 hour. Phosphorylated product was measured with the DELFIA time-resolved fluorescence system (Wallac), using a rabbit anti-p-MEK (Cell Signaling) as the primary antibody and europium labeled anti-rabbit as the secondary antibody. Time resolved fluorescence was read on a Wallac 1232 DELFIA fluorometer. The concentration of the compound of Example 1 for 50% inhibition (IC$_{50}$) was calculated by non-linear regression using XL Fit data analysis software.

Results:

The compound of Example 1 exhibited potent inhibition (IC$_{50}$<0.1 µM) of B-Raf, c-Raf, and mutant B-Raf (V600E) activity as shown below in TABLE 3.

TABLE 3

| In Vitro Potency of the Compound of Example 1 against Raf activity | |
|---|---|
| Target | Compound of Example 1 Biochemical IC$_{50}$ |
| B-Raf (V600E) | 0.0053 µM |
| B-Raf | 0.068 µM |
| c-Raf | 0.004 µM |

Figure 5:
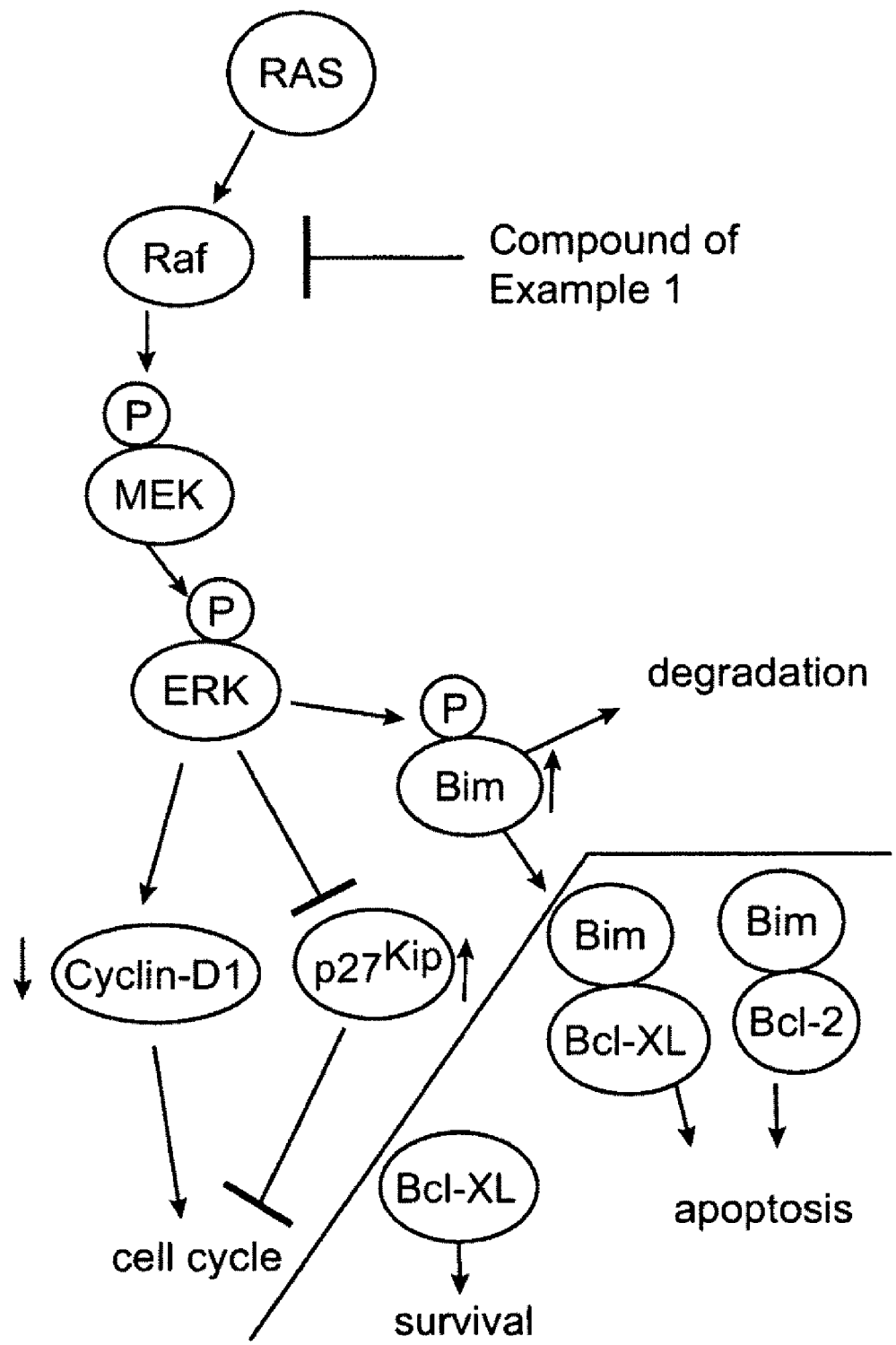
FIG. 5 illustrates the MAPK signaling pathway including Ras, Raf, MEK, and ERK and the proposed point of inhibition of downstream signaling from Raf kinase with the compound of Example 1 as described in Examples 82-86.

As shown above in TABLE 3, the compound of Example 1 displays potent inhibitory activity against wild-type isoform B-Raf, wild-type isoform c-Raf, and mutant B-Raf (V600E) Raf kinase. As shown in FIG. 5, Raf kinases are considered to be the primary Ras effectors in the MAPK (Ras/Raf/MEK/ERK) signaling pathway. The Raf kinases are activated by Ras and phosphorylate and activate Mek1 and Mek2, which in turn activate Mitogen Activated Kinases 1 and 2 (MAPK), in the MAPK pathway. Raf kinases are known to influence and regulate cellular proliferation, differentiation, survival, oncogenic transformation and apoptosis. The B-Raf isoform has been shown to be the most active form of Raf involved in signaling and key in propagating Ras signaling.

As shown below in TABLE 4, the MAPK signaling pathway is implicated in many human cancers. Ras mutations (activated) are found in 15% of all human cancers. ERK mutations (hyper-activated) are found in 30% of all human cancers. Oncogene mutations associated with cancer are common in several members of this pathway, for example the mutant B-Raf (V600E) occurs in about 70% of melanomas, and about 12% of colon carcinoma (Davies et al., Supra; Yuen et al., supra and Brose et al., supra).

TABLE 4

Association between Mutant Signaling molecules in the MAPK pathway and Poor Clinical Outcome

| Indication | Mutant signaling molecules |
|---|---|
| Melanoma | B-Raf(V600E) (70%); N-Ras (15%) |
| Papillary thyroid | B-Raf (V600E) (35-70%); H-,K-,N-Ras (60%) |
| Ovarian Cancer | B-Raf (V600E) (30%) |
| Colon Cancer | B-Raf (V600E) (12%); K-Ras (45%) |
| Pancreatic Cancer | K-Ras (90%) |
| NSC Lung Cancer | K-Ras (35%) |
| ALL, AML | N-Ras (30%) |

See Sebolt-Leopole and Herrera, Nature Reviews Cancer (4): 937 (2004).

As indicated above in TABLE 4, the mutant form of B-Raf (V600E), which is activated, is an important target for cancer treatment because its expression is an indicator of poor prognosis, it is constitutively active, and it drives several tumors, including melanoma, papillary thyroid cancer, ovarian cancer and colon cancer. It has been previously demonstrated that inhibitors of wild-type Raf kinase that also inhibit mutant B-Raf have shown promise as therapeutic agents in cancer therapy. For example, it has been shown that mutant B-Raf depletion by siRNA impairs ERK signaling and proliferation in melanoma cell lines (Dibb, N.J. et al., *Nature Reviews Cancer* (4): 718, 2004). Therefore, it is significant to note that mutant B-Raf is inhibited even more potently with the compound of Example 1 than the wild-type B-Raf, thereby demonstrating the utility of the compound for the inhibition of Raf in the treatment of Raf-mediated diseases including melanoma, ovarian cancer, papillary thyroid cancer and colon cancer.

Example 83

Inhibition of Mutant B-Raf Kinase Signaling with the Compound of Example 1 in Cell-Based Assays 1. Inhibition of ERK Phosphorylation
Methods:

Two melanoma cell lines, A375M (mutant B-Raf V600E), and SKMEL-28 (mutant B-Raf V600E) were used to measure the inhibitory effect of the compound of Example 1 in a cell-based assay. ERK phosphorylation was analyzed after treatment with serial dilutions of the compound of Example 1: {1-Methyl-5-[2-(5-trifluoromethyl-1H-imidazol-2-yl)-pyridin-4-yloxy]-1H-benzo-imidazol-2-yl}-(4-trifluoromethyl-phenyl)-amine in SKMEL-28 cells and A375M cells. $EC_{50}$ values were determined by fitting the data into a four-parameter curve.

Results:

As shown below in TABLE 5, the Compound of Example 1 inhibits mutant B-Raf (V600E) kinase activity in SKMEL-28 cells and A375M cells, as measured by the decrease in phospho-ERK.

TABLE 5

Inhibitory Effect of Compound of Example 1 in Melanoma Cell lines Expressing Mutant Raf-B.

| mutant Raf-B (V600E) Cell line | Compound of Example 1 pERK inhibition $EC_{50}$ |
|---|---|
| A375M | 160 nM |
| SKMEL-28 | 100 nM |

2. Inhibition of MEK Phosphorylation
Methods:

Three Melanoma cell lines, A375M (mutant B-Raf V600E), SKMEL-2 (wild-type Raf, mutant N-Ras), and CHL-1 (wild-type Raf, wild-type Ras) were used to measure the inhibitory effect of the compound of Example 1 in a cell-based assay. The three cell lines were incubated at 37° C. in 0.1% fetal bovine serum with 0.1 μM, 0.5 μM, 1 μM, 5 μM and 10 μM concentrations of the compound of Example 1. After 4 hours of incubation, MEK phosphorylation was analyzed by Western blot analysis.

Figure 6A:
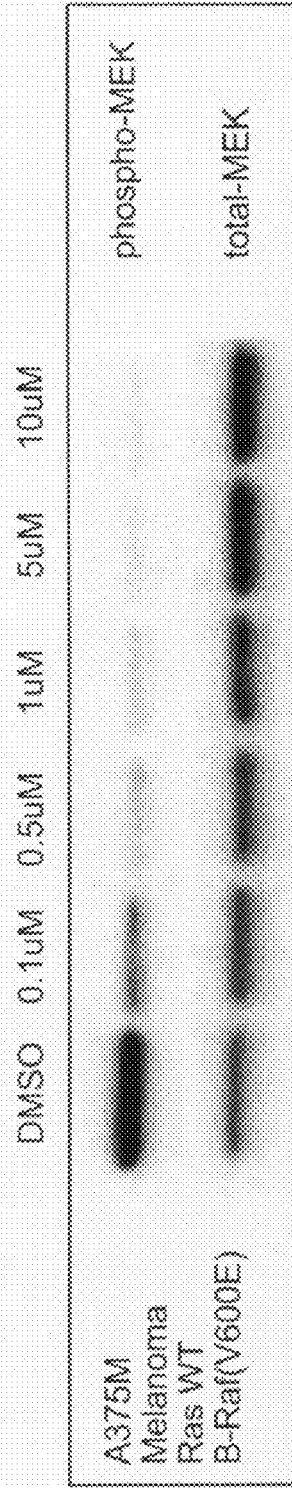
FIGS. 6A, 6B, and 6C are PAGE slides showing the inhibition of downstream signaling from Raf kinase in A375M cells (FIG. 6A), SK-MEL2 cells (FIG. 6B), and CHL-1 cells (FIG. 6C) after 4 hours of incubation in culture with a range of concentrations of the compound of Example 1, as described in Example 83.
Figure 6B:
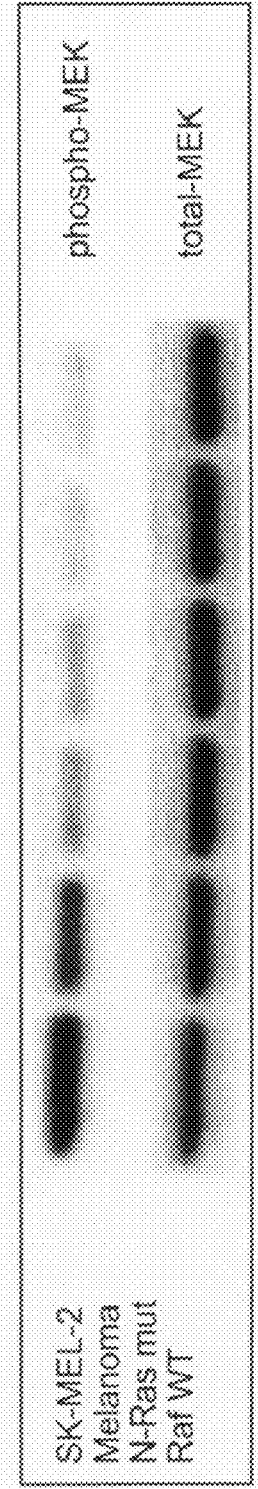
Figure 6C:
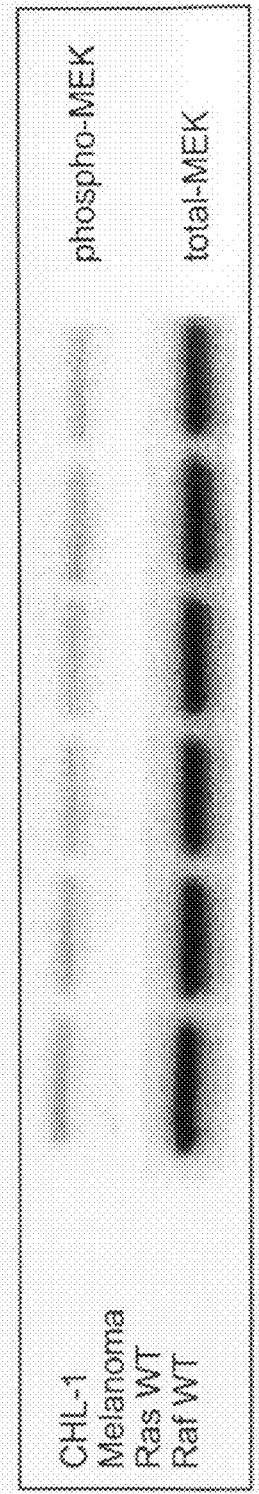

Results:

The results are shown in FIGS. 6A, 6B and 6C. As shown in FIG. 6A, the compound of Example 1 is a potent inhibitor of Raf downstream signaling in A375M cells (FIG. 6A), SKMEL-2 cells (FIG. 6B) and in CHL-1 cells (FIG. 6C) in a concentration range of from 0.1 μM to 10 μM.

3. Inhibition of Anchorage Independent Cell Growth

In order to verify that inhibition of Raf translates into anti-proliferative activity, the compound of Example 1 was tested against a variety of cell lines and human tumor isolates grown in soft-agar, as listed below in TABLE 6.

Soft Agar Proliferation Assay: For each cell line listed below in TABLE 6, 500 cells per 100 μl were seeded in Corning 96 well flat bottom Ultra Low Attachment Micro plates (Corning #3474). 1% seakem GTG agarose was added (50 μl/well) to complete medium, allowed to solidify, and then 100 μl of complete medium was added to each well. Serial dilutions of the compound of Example 1: {1-Methyl-5-[2-(5-trifluoromethyl-1H-imidazol-2-yl)-pyridin-4-yloxy]-1H-benzo-imidazol-2-yl}-(4-trifluoromethyl-phenyl)-amine were made in a final concentration of 5% DMSO in serum-free medium, and 25 μl of the diluted compound was added to each well (final DMSO concentration of 0.5%). A control well contained 0.5% DMSO with no compound was also included in the assay. After 7 days of incubation of the cells with the compound, 25 μl of Alamar Blue (Trek Diagnostic Systems #00-100) was added to each well and incubated at 37° C. for 4 hours. The plates were read with a fluorescence plate reader, excitation 530 nm, emission 590 nm. $EC_{50}$ values were determined by fitting the data into a four-parameter curve.

The compound of Example 1 was also tested against a panel of human tumor isolates grown in soft agar (Oncotest, GmbH, Freiburg, Germany). The tumors were isolated from patients and then passaged as tumor pieces in immuno-compromised mice and assayed using the methods described above.

Results: The Compound of Example 1 has a potent anti-proliferative effect on cell lines and human tumor isolates expressing mutant B-Raf, mutant K-Ras and mutant N-Ras, as shown below in TABLE 6.

TABLE 6

Soft Agar Proliferation Assay: Inhibition with the Compound of Example 1

| Cell line/Tumor Isolates | Type | Mutation | Compound of Example 1 $EC_{50}$ |
|---|---|---|---|
| WM1799 (cell line) | Melanoma | B-Raf (V600E) | <0.0098 μM |
| WM983 (cell line) | Melanoma | B-Raf (V600E) | 0.016 μM |
| A375M (cell line) | Melanoma | B-Raf (V600E) | 0.032 μM |
| SK-MEL28 (cell line) | Melanoma | B-Raf (V600E) | 0.07 μM |
| HT-29 (cell line) | Colorectal Carcinoma | B-Raf (V600E) | 0.026 μM |

TABLE 6-continued

Soft Agar Proliferation Assay: Inhibition with the Compound of Example 1

| Cell line/Tumor Isolates | Type | Mutation | Compound of Example 1 $EC_{50}$ |
|---|---|---|---|
| Colo205 (cell line) | Colorectal Carcinoma | B-Raf (V600E) | 0.13 μM |
| HCT-116 (cell line) Carcinoma | Colorectal | mutant K-Ras | 0.07 μM |
| LoVo (cell line) Carcinoma | Colorectal | mutant K-Ras | 0.016 μM |
| human tumor isolate #1 | Melanoma | B-Raf (V600E) | 0.055 μM |
| human tumor isolate #2 | Melanoma | B-Raf (V600E) | 0.20 μM |
| human tumor isolate #3 | Melanoma | N-Ras (Q61K) | 0.57 μM |
| human tumor isolate #4 | Pancreatic tumor | K-Ras | 1.27 μM |
| human tumor isolate #5 | Colorectal tumor | K-Ras | 1.20 μM |
| human tumor isolate #6 | Renal cell carcinoma | not determined | >1 μM |
| human tumor isolated #7 | Renal cell carcinoma | not determined | >1 μM |

The inhibitory activity of the compound of Example 1 on the broad panel of cell lines and human tumor isolates shown above in TABLE 6 demonstrates the potent anti-proliferative activity of the compound in tumor cells expressing mutant B-Raf. The compound displayed potent inhibition against the mutant B-Raf melanoma cells in the range of <0.0098 to 0.07 μM. The compound displayed a similar degree of inhibition against the mutant B-Raf colorectal cell lines in the range of 0.026 μM to 0.13 μM. The compound also demonstrated potent anti-proliferative activity in the two colorectal carcinoma tumor cells tested that express mutant K-Ras (0.07 μM to 0.016 μM), confirming that inhibition of B-Raf/c-Raf in the context of an upstream K-Ras mutation leads to anti-proliferative activity.

Consistent with the results from the cell lines described above, the compound of Example 1 on the human tumor isolates demonstrated the most potent inhibition against the mutant B-Raf melanomas ($EC_{50}$=0.055 μM and 0.20 μM), followed by the N-Ras mutant melanoma ($EC_{50}$=0.57 μM). One pancreatic tumor and one colorectal tumor had an $EC_{50}$ in the 1 μM range. The remaining tumors gave $EC_{50}$ values greater than 1 μM. The human tumors isolated from patients are believed to represent a more accurate model of disease than the cell lines, because the tumors are isolated from patients and passaged as tumor pieces in immuno-compromised mice. Therefore, they are not selected for growth on plastic and they maintain some of the primary tumor architecture.

It is interesting to note that the compound of Example 1 has an inhibitory activity in the range of greater than 1 μM in the renal cell carcinoma tumor isolates. Although the genotype was not determined on these particular tumors, it is known that renal cell carcinoma tumors do not typically express mutant Ras or mutant B-Raf. Therefore, the compound of Example 1 appears to specifically inhibit the signaling molecules of the MAPK pathway, in particular Raf and Ras kinase molecules.

Example 84

Treatment with the Compound of Example 1 Causes Tumor Regression in the A375M (B-Raf V600E) Human Melanoma Xenograft Model Methods: 3×10$^6$ A375M human melanoma cells were implanted subcutaneously into the right flank of 10-12 week old female Nu/Nu mice weighing approximately 24 g. When the average tumor volume reached approximately 150 mm$^3$ (17 days post-implant), the mice were randomized by tumor volume into four groups of nine mice each and treatment with the compound of Example 1 was started. The mice were dosed by oral gavage every day for 14 days with either vehicle alone, or with 10 mg/kg, 30 mg/kg or 100 mg/kg of the compound of Example 1, all in a volume of 0.1 mL. The compound of Example 1: {1-Methyl-5-[2-(5-trifluoromethyl-1H-imidazol-2-yl)-pyridin-4-yl-oxy]-1H-benzoimidazol-2-yl}-(4-trifluoromethyl-phenyl)-amine was formulated in 100% PEG. The tumor volume was measured twice per week using digital calipers.

Western Blot Analysis

At 8 and 24 hours post 14th dose, the mice were euthanized, and tumors were harvested and flash-frozen. The frozen tumors were thawed on ice, weighed and then homogenized in RIPA buffer with Roche Complete, Mini EDTA-free protease inhibitor cocktail tablets (2 tablets per 25 mL of buffer), 1 mM phenylmethylsulfonylfluoride (PMSF) and 1× Sigma Phosphatase Inhibitor Cocktail II, using the Roche Magna-lyser (2×1 minute cycles at 6500 rpm at 4° C.). For every 100 mg of tumor tissue, 1 mL of RIPA lysis buffer was added. The homogenates were centrifuged at 14K RPM for 20 minutes in a microfuge at 4° C., followed by further homogenization using Qiagen Qiashredders (9K RPM for 2 minutes at 4° C.). The protein concentration was determined using the Pierce BCA protein assay and then 20 μg of each sample was loaded per well in a 4-20% Tris-Glycine SDS-polyacrylamide gel. Following PAGE, protein was transferred to nitrocellulose membranes, blocked (5% non-fat milk powder in TBST) for 1 hour at room temperature and then probed overnight at 4° C. using a 1:1000 dilution (in blocking buffer) of rabbit polyclonal anti-phospho-ERK1/2 antibody (Cell Signalling #9101), rabbit polyclonal anti-phospho-MEK antibody (Cell Signaling #9121), rabbit polyclonal anti-ERK1/2 antibody (Cell Signalling #9102) or rabbit polyclonal anti-MEK antibody (Cell Signalling #9122). Analysis of the modulation of downstream markers was done using a 1:1000 dilution of anti-Bim antibody (Chemicon, # AB17003), anti-Cyclin D1 antibody clone 5D4 (Upstate, #05-263), anti-p27Kip-1 (182-198) antibody (Calbiochem, #506127), anti-phospho-AKT (S473) antibody (Cell Signaling, #9271), anti-phospho-Akt (T308) antibody (Cell Signaling #9275), and anti-phospho-total Akt antibody (Cell Signaling #9272).

The membranes were then washed 5-times (5 minutes each) with TBST at room temperature and an HRP-labeled goat-anti-rabbit antibody was added at 1:5000 dilution in all blots (in blocking buffer) and incubated at room temperature for 1 hour. The membranes were then washed 5-times (5 minutes each) with TBST, and the membranes were incubated with Pierce Super-Signal for 4 mins, followed by exposure onto film for range of time exposures from 1 sec to 20 minutes.

Results:

FIG. 7A is a graph showing a dose response in the mean reduction in tumor volume of A375M (B-Raf V600E) human melanoma tumors in mice when treated with an oral dose of 10 mg/kg, 30 mg/kg or 100 mg/kg of the compound of Example 1. As shown in FIG. 7A, the compound of Example 1 has potent anti-tumor activity in a oral dose-dependent profile. At an oral dose of 100 mg/kg of the compound, tumor regressions were observed in 9/9 of the mice tested.

Figure 7C:
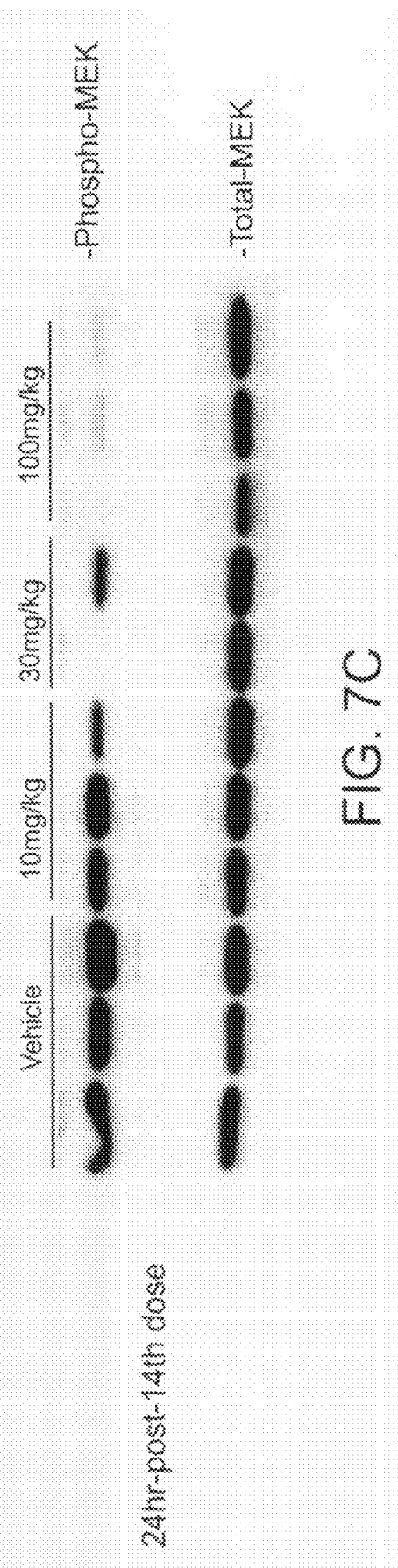
FIG. 7C is a PAGE slide showing the inhibition of downstream signaling from Raf kinase in A375M tumor cells in mice 24 hours after the 14th treatment with the compound of Example 1, as described in Example 84.

The results of the Western blot analysis for the 8 hour, and 24 hour post-14th dose of the 10 mg/kg, 30 mg/kg and 100 mg/kg dose of the compound of Example 1 are shown in FIG. 7B and FIG. 7C, respectively. The Western blot data shows that the compound inhibits MEK phosphorylation at the 100 mg/kg dose (which induces tumor regression), and the MEK inhibition is sustained greater than 24 hours after the last dose, as shown in FIG. 7C.

As shown in FIG. 7D, analysis of downstream biomarker modulation in tumor lysates 24 hrs post the 14th dose showed an increase in BIM (marker of apoptosis) and p27Kip (marker of cell cycle arrest), and a decrease in Cyclin D (cell cycle inhibition). These results confirm that the compound of Example 1 inhibits Raf signaling in the MAPK pathway.

Example 85

Treatment with the Compound of Example 1 Inhibits Melanoma Tumor Growth

The compound of Example 1 was tested for inhibitory activity in a melanoma tumor model MEXF276 (mutant B-Raf V600E) and melanoma tumor model MEXF1341 wild-type B-Raf, mutant N-Ras (Q61K).

Methods: Serially passaged human melanoma MEXF276 (mutant B-Raf V600E) tumor cells were implanted subcutaneously into the hind flank of 10-12 week old female Nu/Nu mice. When the average tumor volume reached approximately 65 $mm^3$, the mice were randomized by tumor volume and treatment with the compound of Example 1 {1-Methyl-5-[2-(5-trifluoromethyl-1H-imidazol-2-yl)-pyridin-4-yloxy]-1H-benzoimidazol-2-yl}-(4-trifluoromethyl-phenyl)-amine was started. Because the MEXF276 model is known to be somewhat cachectic, with some toxicity expected in the non-treated control mice, intermittent dosing regimens were used in order to prevent severe body weight loss in the drug treated groups, as follows. The mice were dosed by oral gavage with either vehicle alone, or with the following dosing regimen of the compound of Example 1: 10 mg/kg on days 0, 2, 4, 6, 14, 16, and 20; with 30 mg/kg on days 0, 2, 14, 16, and 20; and with 100 mg/kg on days 0, 2, 14, 16, and 20.

For the MEXF1341 model, serially passaged human melanoma MEXF1341 tumor cells were implanted subcutaneously into the hind flank of female Nu/Nu mice. When the average tumor volume reached approximately 78 $mm^3$ the mice were randomized by tumor volume and treatment with the compound of Example 1 was started. The mice were dosed by oral gavage with either vehicle alone, or with the following dosing regimen of the compound of Example 1: 10 mg/kg on days 0, 2, 4, 6, 10, 12, 18, and 20; 30 mg/kg on days 0, 2, 4, 6, 10, 12, 18, and 20; and 100 mg/kg on days 0, 2, 4, 6, 10, 12, and 20.

At 4 hours post final dose, the mice from the MEXF276 and MEXF1341 models were euthanized, and the tumors were harvested and flash-frozen. Lysates from these tumors were subsequently analysed by Western blot for target modulation (PMEK) and modulation of downstream markers (BIM, p27Kip and pAKT) as described above in Example 84.

Results:

FIG. 8A is a graph showing the mean reduction in tumor volume of MEXF276 (B-Raf V600E) melanoma cancer tumors in mice when treated with the compound of Example 1. The results shown in FIG. 8A indicate that the compound of Example 1 shows significant tumor growth inhibition in MEXF276 isolates at 10 mg/kg, and greater than or equal to 50% tumor regression in 8/8 mice at 30 mg/kg and 100 mg/kg. Analysis of the pMEK phosphorylation (FIG. 8B) and downstream and downstream biomarker modulation in tumor lysates (FIG. 8C) confirm that mutant B-Raf-activity is inhibited in the MEXF276 tumors, as shown by the decrease in phospho-MEK in FIG. 8B. As shown in FIG. 8C, an increase in BIM (marker for apoptosis) and p27Kip (cell cycle arrest), and a decrease phospho-AKT (survival pathway signaling) was observed, confirming inhibition of Raf kinase activity in the MAPK pathway.

Figure 9A:
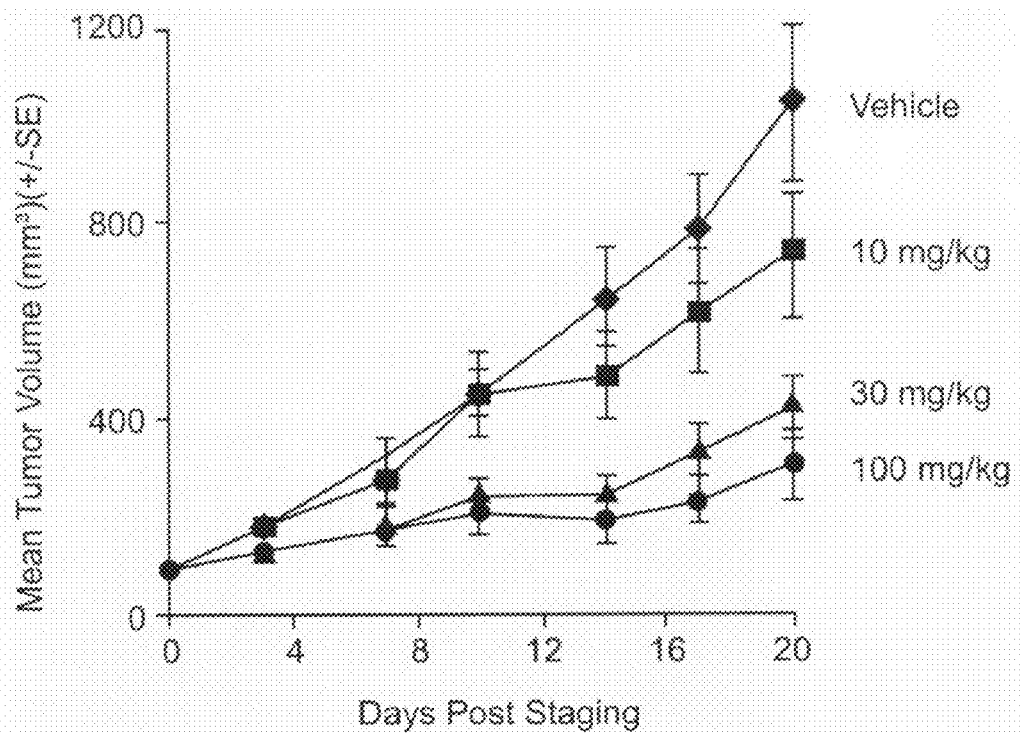
FIG. 9A is a graph showing the mean inhibition of tumor growth of MEXF1341 (N-Ras Q61K) melanoma cancer tumors in mice when treated with the compound of Example 1, as described in Example 85.
Figure 9B:
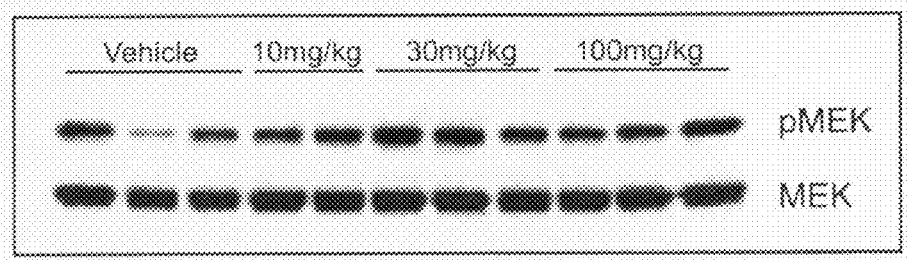
FIG. 9B is a PAGE slide showing the downstream signaling from Raf kinase in MEXF1341 tumor cells in mice 4 hours after the 20th treatment with the compound of Example 1, as described in Example 85.

FIG. 9A is a graph showing the mean inhibition of tumor growth of MEXF1341 (N-Ras Q61K) melanoma cancer tumors in mice when treated with the compound of Example 1. The results shown in FIG. 9A indicate that the compound of Example 1 caused significant tumor growth inhibition (up to 70% inhibition) in the MEXF1341 mutant N-Ras (N-Ras Q61K) melanoma tumor model at the 30 mg/kg and 100 mg/kg doses, but did not induce tumor regression. As shown in FIG. 9B, analysis of the phospho-MEK post day 20 after treatment with 100 mg/kg of the compound did not show an observable decrease in phospho-MEK, in contrast to the results obtained with the MEXF276 (mutant B-Raf) model. In addition, while there was some evidence the signaling molecules in the MAPK pathway downstream of Raf in the MEXF1341 model were affected, the effect was less dramatic than observed in the MEXF276 model. For example, as shown in FIG. 9C, the p27Kip levels (cell cycle arrest) increased in the 30 mg/kg and 100 mg/kg groups indicating growth arrest, and a slight increase in the apoptotic marker BIM was observed. Therefore, it appears that the compound of Example 1 has potent activity in the MEXF276 (mutant B-Raf) xenograft model, causing tumor regression, and significant, but less potent activity in the MEXF1341 (wild-type B-Raf, mutant N-Ras) xenograft model, causing tumor growth inhibition.

Example 86

Treatment with the Compound of Example 1 Inhibits Human Colorectal Carcinoma Tumor Growth The compound of Example 1 was tested for inhibitory activity in a colorectal carcinoma xenograft models HCT-116 (mutant K-Ras G13D), HT-29 (B-Raf V600E) and acute leukemia xenograft model MV4-11 (FLT3 ITD).

Methods: $5 \times 10^6$ HCT-116 (mutant K-Ras G13D) human colorectal carcinoma cells were implanted subcutaneously into the hind flank of 10-12 week old female Nu/Nu mice weighing approximately 24 g. When the average tumor volume reached approximately 212 $mm^3$ the mice were dosed by oral gavage with either vehicle alone, or with the following dosing regimen of the compound of Example 1: 10 mg/kg, 30 mg/kg and 100 mg/kg by oral gavage on day 1 and every 2 days (q2d) for a total of 28 days. Satellite mice were euthanized and tumors were harvested at 4 hours, 8 hours and 24 hours after the 3rd dose. Lysates from these tumors were subsequently analysed by Western blot for target modulation (pMEK) as described above in Example 84.

A second human colorectal carcinoma model, HT-29 (B-Raf V600E), was tested as follows. 2×10⁶ HT-29 cells were implanted subcutaneously into the hind flank of 10-12 week old female Nu/Nu mice weighing approximately 24 g. When the average tumor volume reached approximately 167 mm³ the mice were dosed by oral gavage with either vehicle alone, or with the following dosing regimen of the compound of Example 1: 10 mg/kg, 30 mg/kg and 100 mg/kg by oral gavage on day 1 and every 2 days (q2d) for a total of 28 days.

A human acute monocytic leukemia xenograft model, MV4-11 (FLT3 ITD), was tested as follows: 5×10⁶ MV4-11 cells were implanted subcutaneously into the hind flank of 10-12 week old female Nu/Nu mice weighing approximately 24 g. When the average tumor volume reached approximately 190 mm³ the mice were dosed by oral gavage with either vehicle alone, or with the following dosing regimen of the compound of Example 1: 10 mg/kg, 30 mg/kg and 100 mg/kg by oral gavage on day 1 and every 2 days (q2d) for a total of 16 days. Satellite mice were euthanized and tumors were harvested at 4 hours after the 3rd dose. Lysates from these tumors were subsequently analysed by Western blot for target modulation (pMEK) as described above in Example 84.

Figure 10D:
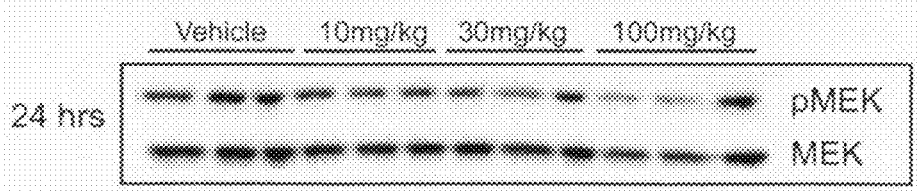
FIG. 10D is a PAGE slide showing the inhibition of downstream signaling from Raf kinase in HCT-116 tumor cells in mice 24 hours after the 3rd treatment with the compound of Example 1, as described in Example 86.

Results:

The results for the HCT-116 study are shown in FIGS. 10A-D. FIG. 10A is a graph showing the mean reduction in tumor volume of HCT-116 (1-Ras G13D) colorectal carcinoma tumors in mice when treated with 100 mg/kg of the compound of Example 1. As shown in FIGS. 10B-10D, analysis of the phospho-MEK 4 hours (FIG. 10B), 8 hours (FIG. 10C) and 24 hours (FIG. 10D) post the 3rd dose showed an observable decrease in phospho-MEK.

Figure 11:
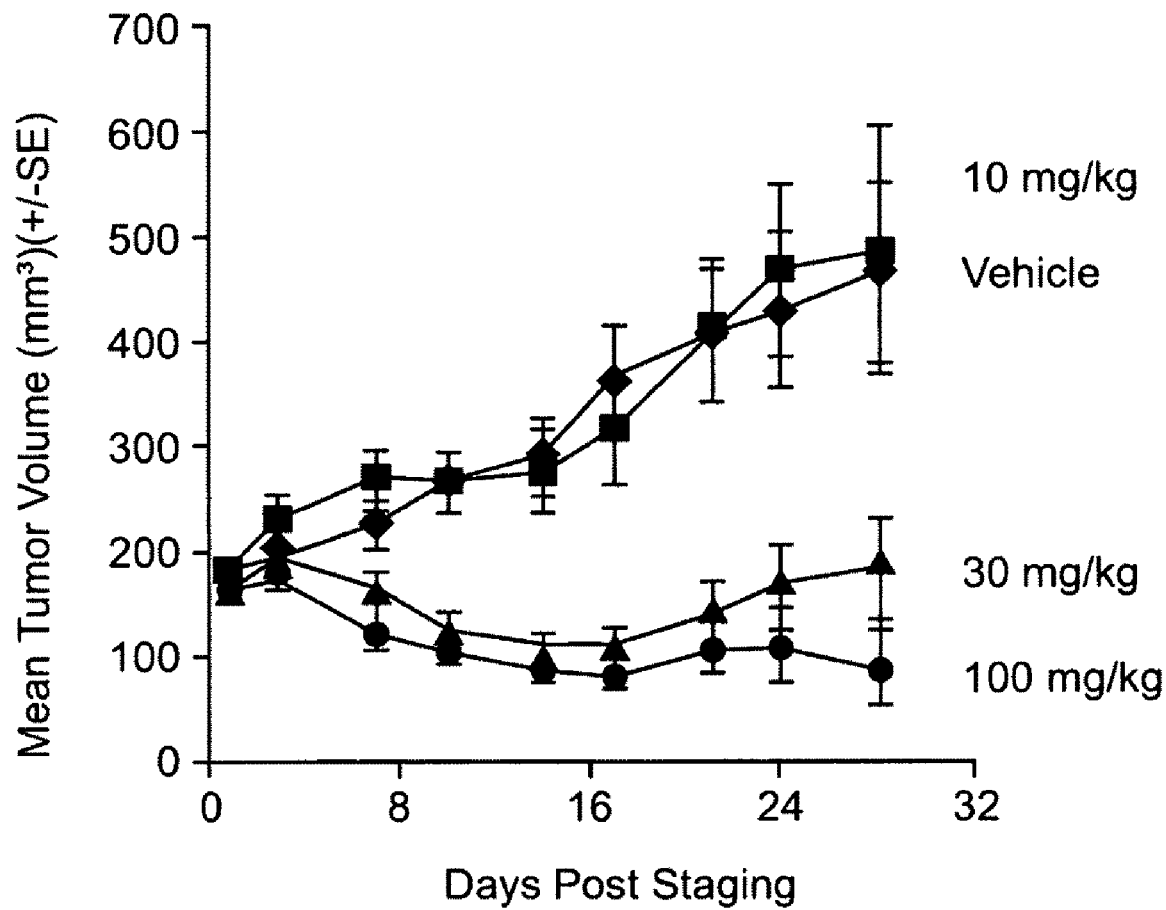
FIG. 11 is a graph showing the mean reduction in tumor volume of HT-29 (B-Raf V600E) colorectal carcinoma tumors in mice when treated with the compound of Example 1, as described in Example 86.

FIG. 11 is a graph showing the mean reduction in tumor volume of HT-29 (B-Raf V600E) colorectal carcinoma tumors in mice when treated with the compound of Example 1. As shown in FIG. 11, tumor regression was observed at 30 mg/kg and 100 mg/kg.

Figure 12A:
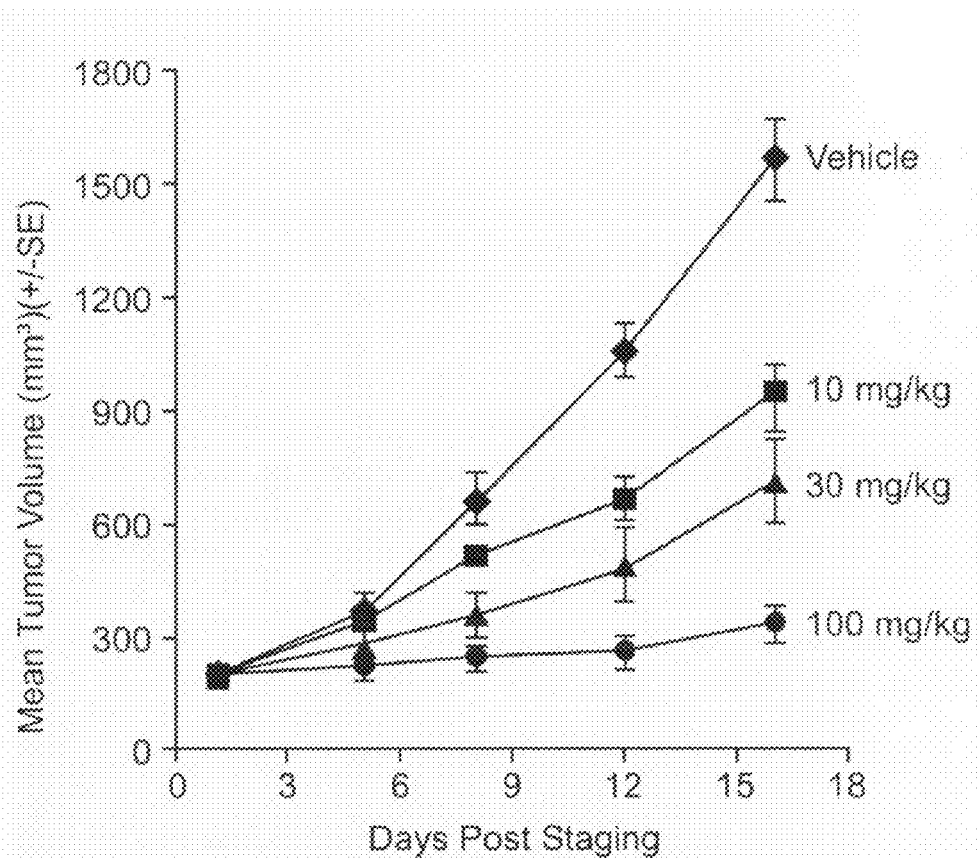
FIG. 12A is a graph showing the mean inhibition of tumor growth of MV4-11 (FLT3 ITD) acute monocytic leukemia cancer tumors in mice when treated with the compound of Example 1, as described in Example 86.
Figure 12B:
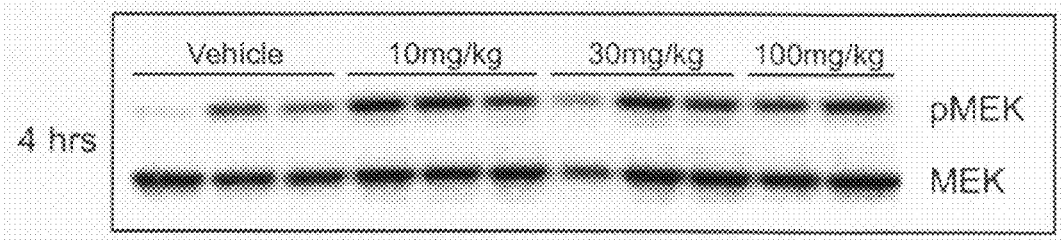
FIG. 12B is a PAGE slide showing the downstream signaling from Raf kinase in MV4-11 tumor cells in mice 4 hours after the 3rd treatment with the compound of Example 1, as described in Example 86.

The results for the MV4-11 study are shown in FIGS. 12A-B. FIG. 12A is a graph showing the mean inhibition of tumor growth of MV4-11 acute monocytic leukemia cancer tumors in mice when treated with the compound of Example 1. The MV4-11 tumor cells are driven by the mutant receptor tyrosine kinase (MV4; 11, FLT3 ITD). As shown, the compound of Example 1 caused significant tumor growth inhibition in the MV-11 model, however, there was no evidence of tumor regression (FIG. 12A), nor was there an observable inhibition of MEK signaling (FIG. 12B). While not wishing to be bound by theory, in the MV4-11 model it is likely that the efficacy of tumor growth inhibition is a result of the compound's anti-angiogenic activity, primarily through the inhibition of VEGFR-2, as described below in EXAMPLES 87-88.

A summary of the data obtained from the evaluation of the efficacy of the compound of Example 1 in the melanoma, colorectal carcinoma and leukemia xenograft models described above is provided below in TABLE 7.

TABLE 7

Summary of Activity of the compound of Example 1 in various Xenograft Models

| Xenograft Model | Genotype | Initial Tumor Volume | Dose (mg/kg) | Schedule | TGI/ Regression |
|---|---|---|---|---|---|
| A375M (melanoma) | B-Raf (V600E) | 100 mm³ | 10 | qdx14 | 53% TGI |
| | | | | q2dx14 | 33% TGI |
| | | | 30 | qdx14 | 78% TGI |
| | | | | q2dx14 | 81% TGI |
| | | | 100 | qd | regression |
| | | | | q2dx14 | regression |
| | | | | q3dx9 | regression |
| | | | | q4dx7 | 85% TGI |
| MEXF-276 (melanoma) | B-Raf (V600E) | 65 mm³ | 10 | Days 0, 2, 4, 6, 14, 16, 20 | 80% TGI |
| | | | 30 | Days 0, 2, 14, 16, 20 | regression |
| | | | 100 | Days 0, 2, 14, 16, 20 | regression |
| HT29 (colorectal) | B-Raf (V600E) | 167 mm³ | 10 | q2dx14 | 12% TGI |
| | | | 30 | q2dx14 | regression |
| | | | 100 | q2dx14 | regression |
| MEXF 1341 (melanoma) | N-Ras (wt/Q61K) | 78 mm³ | 10 | Days 0, 2, 4, 6, 10, 12, 18, 20 | 30% TGI |
| | | | 30 | Days 0, 2, 4, 6, 10, 12, 18, 20 | 60% TGI |
| | | | 100 | Days 0, 2, 4, 6, 10, 12, 20 | 71% TGI |
| HCT-116 (colorectal) | K-Ras (wt/G13D) | 212 mm³ | 10 | q2d x 14 | 33% TGI |
| | | | 30 | q2d x 14 | 81% TGI |
| | | | 100 | q2d x 14 | regression |
| MV4; 11 (AML) | FLT3 LTD | 190 mm³ | 10 | q2d x 7 | 41% TGI |
| | | | 30 | q2d x 7 | 55% TGI |
| | | | 100 | q2d x 7 | 79% TGI |

From the data summarized in TABLE 7, as shown in FIGS. 6-12, and as described in EXAMPLES 82-86, the compound of Example 1 is efficacious in every xenograft model tested in which B-Raf is mutated, causing regression of tumors and target modulation in all three of the models tested (A375M, MEXF276, and HT29).

Example 87

Tyrosine Kinase Inhibition Assays

1. Biochemical Assays:

The kinase activity of a number of protein tyrosine kinases was measured by providing ATP and an appropriate peptide or protein containing a tyrosine amino acid residue for phosphorylation, and assaying for the transfer of the phosphate moiety to the tyrosine residue. Recombinant proteins corresponding to the cytoplasmic domains of the VEGFR2, PDGFRβ, CSF-1R and c-Kit were obtained by purification from Sf9 insect cells infected with a corresponding human VEGFR2, PDGFRβ, CSF-1R and c-Kit recombinant baculovirus expression vector. For each assay, the compound of Example 1 {1-Methyl-5-[2-(5-trifluoromethyl-1H-imidazol-2-yl)-pyridin-4-yloxy]-1H-benzoimidazol-2-yl}-(4-trifluoromethyl-phenyl)-amine, was serially diluted in DMSO and then mixed with an appropriate kinase reaction buffer plus ATP (the ATP concentration used was at or just below the respective Km value). The kinase protein and an appropriate biotinylated peptide substrate were added to give a final volume of 50-100 µL. Reactions were incubated for 1-3 hours at room temperature and then stopped by addition of 25-50 µL of 45 mM EDTA, 50 mM Hepes pH 7.5. The stopped reaction mixture (75 µL) was transferred to a streptavidin-coated microtiter plate (Boehringer Mannheim) and incubated for 1 hour. Phosphorylated peptide product was measured with the DELFIA time-resolved fluorescence system (Wallac or PE Biosciences), using a Europium labeled anti-phosphotyrosine antibody PT66 with the modification that the DELFIA assay buffer was supplemented with 1 mM $MgCl_2$ for the antibody dilution. Time resolved fluorescence was read on a Wallac 1232 DELFIA fluorometer or a PE Victor II multiple signal reader. The concentration of each compound for 50% inhibition ($IC_{50}$) was calculated employing non-linear regression using XL Fit data analysis software.

VEGFR2 kinase (0.05 µg/mL) was assayed in 50 mM Hepes pH 7.0, 2 mM $MgCl_2$, 100M $MnCl_2$, 1 mM NaF, 1 mM dithiothreitol (DTT), 1 mg/mL bovine serum albumin (BSA), 1 to 30 µM ATP, and 0.25 µM biotinylated peptide substrate "GGGGQDGKDYIVLPI" (SEQ ID NO:1).

For the PDGFR kinase assay, 120 µg/mL enzyme with the same buffer conditions as above was used except for changing ATP and peptide substrate concentrations to 1.4 µM ATP, and 0.25 µM biotinylated peptide substrate "GGGGQDGKDYIVLPI" (SEQ ID NO:1).

The kinase activity of CSF-1R was assayed in assay buffer (50 mM HEPES pH 7.0, 5 mM $MgCl_2$, 10 mM $MnCl_2$, 0.1% BSA, 1 mM DTT, 0.01% Tween, final pH 7.5), 1 µM ATP and 50 nM biotinylated peptide substrate "EEEEAYGWLNF" (SEQ ID NO:2).

The kinase activity of c-Kit was measured by providing ATP and the recombinant protein corresponding to the cytoplasmic domain of the c-Kit receptor (obtained from Proquinase). The c-Kit kinase protein (2 nM) and the biotinylated peptide substrate (1 µM) "GGLFDDPSWNVQNL" (SEQ ID NO: 3), were added in reaction buffer plus ATP (8 µM) to give a final volume of 100 µL. The reaction buffer for c-Kit was 50 mM HEPES pH 7.5, 1 mM NaF, 2 mM $MgCl_2$, 10 mM $MnCl_2$ and 1 mg/mL BSA. The reaction was incubated for 2 hours at room temperature and stopped by addition of 50 µL of 45 mM EDTA, 50 mM HEPES, pH 7.5. The stopped reaction mixture (75 µL) was transferred to a streptavidin-coated mictrotiter plate (Boehringer Mannheim) and incubated for 1 hour. Phosphorylated peptide product was measured with the DELPHIA time-resolved fluorescence system (Wallac or PE Biosciences), using a Europium-labeled anti-phosphotyrosine antibody, PT66, with the modification that the DELFIA assay buffer was supplemented with 1 mM $MgCl_2$ for the antibody detection. Time resolved fluorescence values were determined on a Wallac 1232 DELFIA fluorometer or a PE Victor II multiple signal reader. The concentration of the compound of Example 1 for 50% inhibition (ICSO) was calculated employing non-linear regression using XL Fit data analysis software.

Results: As shown below in TABLE 8, the compound of Example 1 is a potent inhibitor of VEGFR-2, c-Kit, PDGFR-β and CSF-1R.

TABLE 8

Inhibition of tyrosine kinases with the compound of Example 1

| Target | Compound of Example 1 Biochemical $IC_{50}$ | Compound of Example 1 Cell-based EC50 |
|---|---|---|
| VEGFR-2 | 0.07 µM | 0.03 µM |
| c-Kit | 0.02 µM | 1.1 µM |
| PDGFR-β | 0.0032 µM | 0.7 µM |
| CSF-1R | 0.20 µM | ND |

Cell-based assays were also used to measure the activity of the compound of Example 1 against the target molecules shown in TABLE 8 as follows.

Target modulation in HMVEC cells after treatment with the compound of Example 1 showed inhibition of VEGF mediated VEGFR-2 phosphorylation with an $EC_{50}$ of 0.03 µM, as measured by a decrease in phospho-VEGFR by Western blot (not shown).

Analysis of inhibition of c-Kit in Mo7e cells after treatment with compound of Example 1 showed inhibition of c-Kit phosphorylation with an $EC_{50}$ Of 1.1 µM as measured by a decrease in phospho-c-Kit by ELISA.

Analysis of inhibition of PDGFR-β in MG63 cells after treatment with compound of Example 1 showed inhibition of phospho-PDGFR-β with an $EC_{50}$ of 0.7 µM as measured by a decrease in phospho-PDGFR-β by ELISA.

Example 88

Inhibition of Angiogenesis

To further investigate the effect of the compound of Example 1 against VEGFR-2, the compound was evaluated in a CHO-VEGF Matrigel angiogenesis model.

Methods: 110 Nu/Nu mice (n=10/group) were acclimated one week prior to the start of the study. On day 1, $5 \times 10^6$ VEGF-CHO cells in 0.5 mL Matrigel were subcutaneously injected over the upper abdomen of the mice. On day 1, mice were given oral doses of either vehicle, 10 mg/kg, 30 mg/kg or 100 mg/kg of the compound of Example 1 on a dosing schedule of qdx5. After five days the Matrigel plug was removed from the mice and the hemoglobin concentration therein was quantitated.

Results:

FIG. 13 is a graph showing the inhibition of VEGF-mediated angiogenesis in a CHO-VEGF Matrigel model after treatment with 10 mg/kg, 30 mg/kg, and 100 mg/kg of the compound of Example 1. As shown in FIG. 13, the dosing of the compound over 5 days significantly inhibited VEGF-mediated angiogenesis.

Example 89

Dosing Schedule Effects

Dose scheduling studies of the compound of Example 1 were done in the A375M human melanoma xenograft model to evaluate the relationship between the mutant B-Raf inhibition, tumor response, and compound concentration in plasma.

Clear dose-response relationships have been established in the A375M model with the compound of Example 1, as shown in FIG. 7A. The data in FIG. 7A indicate that the compound of Example 1 induces tumor regression at 100 mg/kg when given daily, and tumor regression is associated with sustained inhibition of mutant B-Raf (as shown by a decrease in phospho-MEK in FIG. 7B). However, on this dosing schedule, the compound of Example 1 was not well tolerated in mice at the 30 mg/kg and the 100 mg/kg dose levels, since the mice lost an average of 10% of their starting body weight by day 14. Therefore, the most efficacious dosage of 100 mg/kg was further evaluated as described below.

Methods:

As in Example 84, $3 \times 10^6$ A375M human melanoma cells were implanted subcutaneously into the right flank of 10-12 week old female Nu/Nu mice weighing approximately 24 g. When the average tumor volume reached approximately 200 mm$^3$, the mice were randomized by tumor volume into four groups of nine mice each and treatment with the compound of Example 1 was started. The mice were dosed by oral gavage for 32 days with either vehicle alone, or with the compound of Example 1 in the following dosing regimen: 100 mg/kg on a q2d, q3d or q4d schedule over 28 days.

In this study, satellite groups of tumor-bearing mice were dosed in order to monitor target modulation in tumors. Tumors and plasma were harvested from the mice at various time points following 5 doses on the q2d group and 3 doses on the q4d group. Tumors were processed for Western blot analysis of phospho-MEK levels as described in Example 84, and plasma was isolated for measurement of drug levels.

Figure 14A:
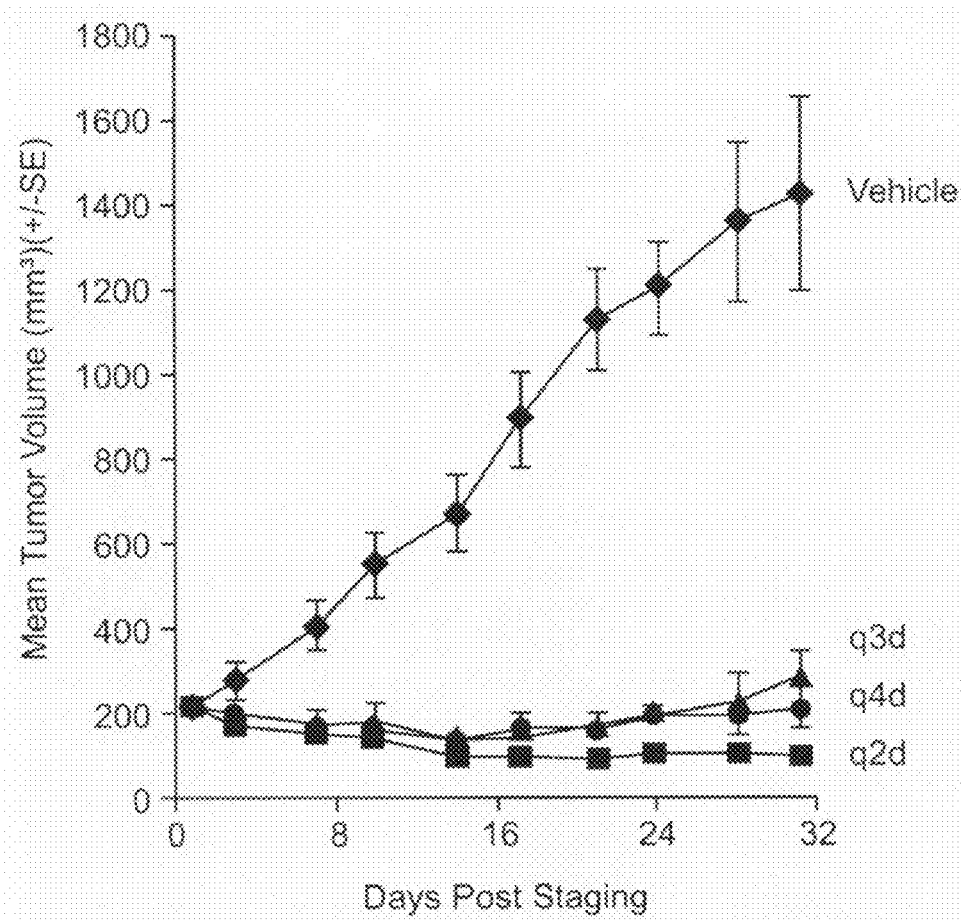
FIG. 14A is a graph showing the mean reduction in tumor volume of A375M melanoma tumors in mice when treated with 100 mg/kg of the compound of Example 1 with a q2d, q3d, or q4d dosing regimen as described in Example 89.

Results:

FIG. 14A is a graph showing the mean reduction in tumor volume of A375M melanoma tumors in mice when treated with 100 mg/kg of the compound of Example 1 with a q2d, q3d, or q4d dosing regimen. As shown in FIG. 14A, the compound of Example 1 dosed orally at 100 mg/kg on a q2d, q3d or q4d schedule resulted in significant efficacy. The Western blot analysis shown in FIG. 14B indicates that the tumors in the compound treated mice have decreased phospho-MEK levels relative to vehicle treated controls up to 48 hours post-dose in the q2d samples. In the q4d samples, by 72 hours only one out of three tumors had decreased levels of phospho-MEK and by 96 hours all of the compound treated tumors had phospho-MEK levels comparable to vehicle treated tumors. These results are consistent with the results obtained on the q2d schedule, shown in FIG. 7B.

As shown below in TABLE 9, the q3d and q4d schedules were better tolerated in the test mice, as measured by weight loss.

TABLE 9

A375M xenograft dosing study with 100 mg/mL of the compound of Example 1

| Dosing Schedule: (100 mg/kg of compound of Example 1 per dose) | Mean body weight loss on day 28 | TGI/Regression |
|---|---|---|
| q2d | 12% | Tumor regression by at least 50% in 10/10 tumors |
| q3d | 8% | Tumor regression by at least 50% in 7/10 tumors |
| q4d | 7% | Regression by at least 50% in 3/10 tumors |

In conclusion, when the target modulation data and efficacy data are considered together, it appears that the q2d or q3d schedule results in the most efficacious tumor regression with maximum host tolerance.

Example 90

Target Plasma Concentration Studies

Figure 14B:
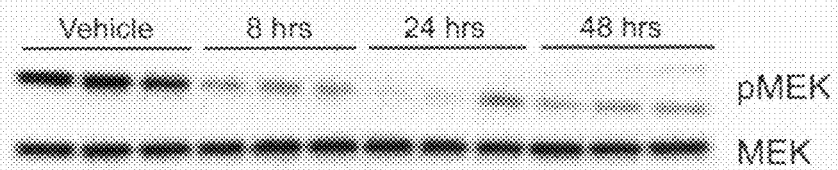
FIG. 14B is a PAGE slide showing the inhibition of downstream signaling from Raf kinase in A375M tumor cells in mice 8 hours, 24 hours, and 48 hours after the 5th treatment with the compound of Example 1 in the q2d dosing regimen, as described in Example 89.
Figure 14C:
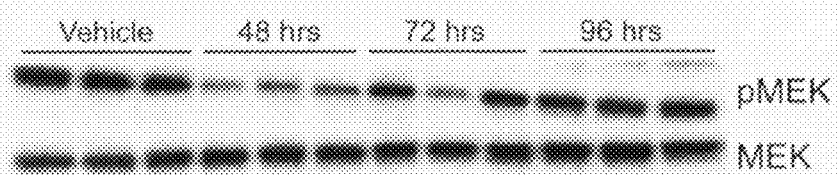
FIG. 14C is a PAGE slide showing the inhibition of downstream signaling from Raf kinase in A375M tumor cells in mice 48 hours, 72 hours, and 96 hours after the 3rd treatment with the compound of Example 1 in the q4d dosing regimen, as described in Example 89.
Figure 15:
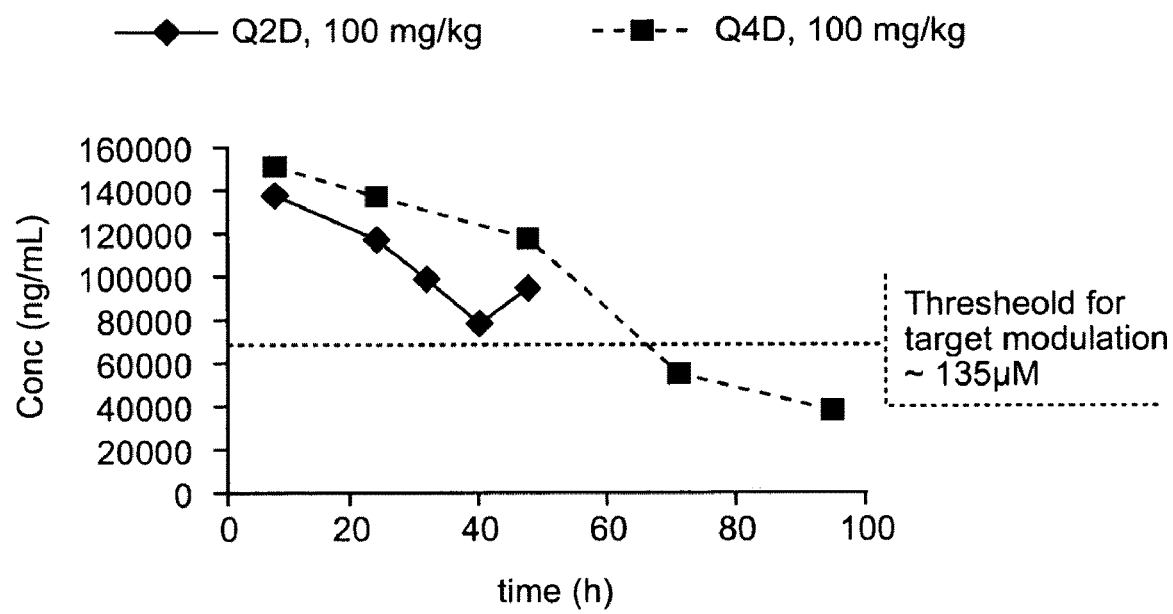
FIG. 15 is a graph showing the relationship between treatment with A375M tumor cells with various concentrations of the compound of Example 1, the serum concentration of the compound over time, and the threshold concentration for target modulation, as described in Example 90.

As described above in Example 89, serum samples were taken for mice treated with the compound of Example 1. The drug concentrations were determined from the serum samples, and the results are shown as compound concentration versus time plots in FIG. 15. A threshold drug concentration for target modulation can be estimated from FIG. 15 by considering the target modulation data shown in FIG. 14A and FIG. 14B. As shown in FIG. 14B, at all time points up to 48 hours post-dose, phospho-MEK levels were reduced in compound treated tumors relative to vehicle treated tumors, therefore the corresponding drug concentrations must be above this threshold. As shown in FIG. 14C, at 72 and 96 hours post-dose, there was no target modulation, and therefore the corresponding drug concentrations must be below this threshold. In conclusion, the threshold of the compound is estimated to be between about 50,000 and 80,000 ng/mL, such as approximately 70,000 ng/mL (135 µM).

It is interesting to note that the target plasma concentration in the mouse xenograft studies described above is approximately 1000-fold higher than the $EC_{50}$ for target modulation in A375M cells (0.16 µM) in vitro (see TABLE 5). This difference may be largely explained by plasma protein binding because the compound of Example 1 is greater than 99.9% protein bound in plasma. Taking this into consideration, a rough estimation of free drug concentration is approximately 0.135 µM, which is close to the in vitro $EC_{50}$ of 0.16 µM determined for target modulation in A375M cells.

In order to further explore the effect of plasma protein binding on the activity of the compound of Example 1, a series of in vitro experiments were performed in which the compound was pre-incubated in 50% serum from mouse, rat, dog, monkey or human, and then applied to A375M cells or Mo7e cells. Phospho-MEK and phospho-ERK levels were measured in A375M cells (to assay for mutant B-Raf inhibition) following overnight incubation. Phospho-c-Kit levels were measured in Mo7e cells (to assay for c-Kit inhibition) following 4 hours of incubation. The results of these assays are summarized below in TABLE 10.

TABLE 10

Effect of serum from various species on the activity of the compound of Example 1

| Species | Phospho-MEK $EC_{50}$ (μM) | Phospho-ERK $EC_{50}$ (μM) | Phospho-c-c-Kit $EC_{50}$ (μM) |
|---|---|---|---|
| Mouse | 153 ± 15.5 | 160 ± 27 | 126 ± 22 |
| Rat | 24 ± 5.7 | 37 ± 7.0 | 29 ± 6.4 |
| Dog | 18 ± 2.4 | 20 ± 2.8 | nd |
| Monkey | 9 ± 3.3 | 13 ± 0.9 | nd |
| Human | 15 ± 1.5 | 20 ± 5.0 | 16 ± 1.5 |

The data in TABLE 10 can be used to evaluate the relative binding of the compound of Example 1 to plasma proteins from different species and as a basis for a correction factor to extrapolate the target plasma concentration determined in mouse to other species. For example, based on these data one would estimate that the target plasma concentration in rat is approximately 5-fold lower than in mouse, and the target plasma concentration in human is approximately 10-fold lower than in mouse.

While the preferred embodiment of the invention has been illustrated and described, it will be appreciated that various changes can be made therein without departing from the spirit and scope of the invention.

---

SEQUENCE LISTING

<160> NUMBER OF SEQ ID NOS: 3

<210> SEQ ID NO 1
<211> LENGTH: 15
<212> TYPE: PRT
<213> ORGANISM: Artificial Sequence
<220> FEATURE:
<223> OTHER INFORMATION: Biotinylated Peptide Substrate

<400> SEQUENCE: 1

Gly Gly Gly Gly Gln Asp Gly Lys Asp Tyr Ile Val Leu Pro Ile
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: Biotinylated Peptide Substrate

<400> SEQUENCE: 2

Glu Glu Glu Glu Ala Tyr Gly Trp Leu Asn Phe
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Biotinylated Peptide Substrate

<400> SEQUENCE: 3

Gly Gly Leu Phe Asp Asp Pro Ser Trp Asn Val Gln Asn Leu
1               5                   10

What is clamed is:

1. A method for treating colorectal cancer in a human or animal subject, the method comprising administering to the human or animal subject a compound that is {1-methyl-5-[2-(5-trifluoromethyl-1H-imidazol-2-yl)-pyridin-4-yloxy]-1H-benzoimidazol-2-yl}-(4-trifluoromethylphenyl)-amine:

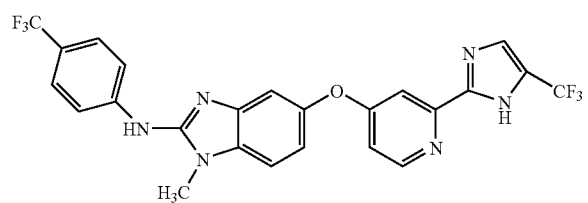

or a tautomer thereof:

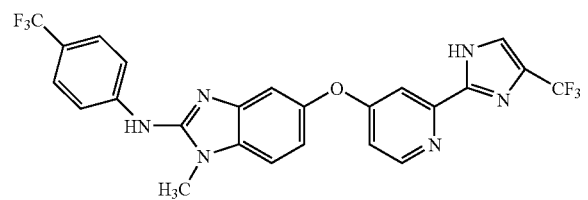

or a pharmaceutically acceptable salt thereof or a pharmaceutically acceptable salt of the tautomer.

2. A method for treating acute monocytic leukemia in a human or animal subject, the method comprising administering to the human or animal subject a compound that is {1-methyl-5-[2-(5-trifluoromethyl-1H-imidazol-2-yl)-pyridin-4-yloxy]-1H-benzoimidazol-2-yl }-(4-trifluoromethylphenyl)-amine:

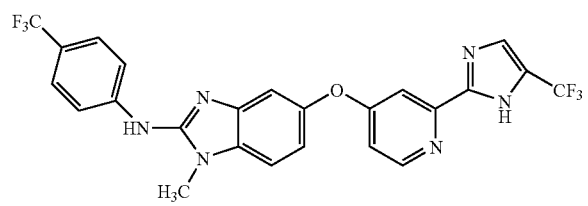

or a tautomer thereof:

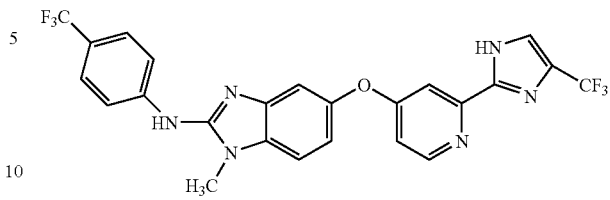

or a pharmaceutically acceptable salt thereof or a pharmaceutically acceptable salt of the tautomer.

3. A method for treating melanoma in a human or animal subject, the method comprising administering to the human or animal subject a compound that is {1-methyl-5-[2-(5-trifluoromethyl-1H-imidazol-2-yl)-pyridin-4-yloxy]-1H-benzoimidazol-2-yl}-(4-trifluoromethylphenyl) -amine:

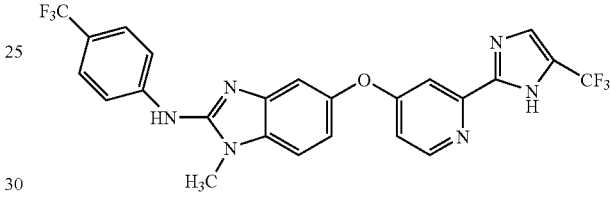

or a tautomer thereof:

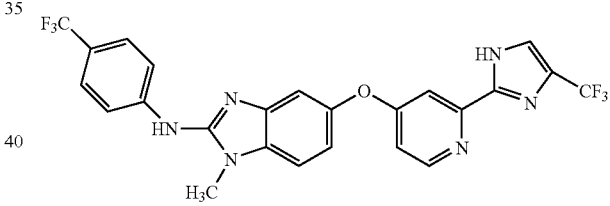

or a pharmaceutically acceptable salt thereof or a pharmaceutically acceptable salt of the tautomer.

* * * * *